United States Patent
Taylor et al.

(10) Patent No.: US 6,974,560 B2
(45) Date of Patent: *Dec. 13, 2005

(54) ELECTRO-KINETIC AIR TRANSPORTER AND CONDITIONER DEVICE WITH ENHANCED ANTI-MICROORGANISM CAPABILITY

(75) Inventors: Charles E. Taylor, Sebastopol, CA (US); Shek Fai Lau, Foster City, CA (US); Andrew J. Parker, Novato, CA (US); Tristan M. Christianson, San Francisco, CA (US); Gregory S. Snyder, Novato, CA (US); Edward C. McKinney, Jr., San Rafael, CA (US)

(73) Assignee: Sharper Image Corporation, San Francisco, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 10/074,096

(22) Filed: Feb. 12, 2002

(65) Prior Publication Data

US 2003/0206839 A1 Nov. 6, 2003

Related U.S. Application Data

(63) Continuation-in-part of application No. 09/774,198, filed on Jan. 29, 2001, now Pat. No. 6,544,485, and a continuation-in-part of application No. 09/924,624, filed on Aug. 8, 2001, which is a continuation of application No. 09/564,960, filed on May 4, 2000, now Pat. No. 6,350,417, which is a continuation-in-part of application No. 09/186,471, filed on Nov. 5, 1998, now Pat. No. 6,176,977, said application No. 10/074,096, and a continuation-in-part of application No. 09/730,499, filed on Dec. 5, 2000, now Pat. No. 6,713,026, which is a continuation of application No. 09/186,471, filed on Nov. 5, 1998, now Pat. No. 6,176,977.

(60) Provisional application No. 60/341,179, filed on Dec. 13, 2001, and provisional application No. 60/306,479, filed on Jul. 18, 2001.

(51) Int. Cl.$^7$ .............................................. B01J 19/08
(52) U.S. Cl. .......................... 422/186.04; 422/186.07; 422/186.3
(58) Field of Search ...................... 422/186.04, 186.07, 422/186.3

(56) References Cited

U.S. PATENT DOCUMENTS

| | | | |
|---|---|---|---|
| 653,421 A | 7/1900 | Lorey | 210/330 |
| 995,958 A | 6/1911 | Goldberg | 472/186.18 |

(Continued)

FOREIGN PATENT DOCUMENTS

| | | |
|---|---|---|
| CN | 2111112 U | 7/1972 |
| CN | 87210843 U | 7/1988 |

(Continued)

OTHER PUBLICATIONS

U.S. Appl. No. 60/104,573, filed Oct. 16, 1998, Krichtafovitch.

(Continued)

*Primary Examiner*—Rodney G. McDonald
(74) *Attorney, Agent, or Firm*—Bell, Boyd & Lloyd LLC

(57) ABSTRACT

An electro-kinetic air conditioner for removing particulates from the air creates an airflow using no moving parts. The airflow is subjected to UV radiation from a germicidal lamp within the device. The conditioner includes an ion generator that has an electrode assembly including a first array of emitter electrodes, a second array of collector electrodes, and a high voltage generator. The device can also include a third or leading or focus electrode located upstream of the first array of emitter electrodes, and/or a trailing electrode located downstream of the second array of collector electrodes, and/or an interstitial electrode located between collector electrodes, and/or an enhanced emitter electrode with an enhanced length in order to increase emissivity.

42 Claims, 39 Drawing Sheets

U.S. PATENT DOCUMENTS

| | | | |
|---|---|---|---|
| 1,791,338 A | 2/1931 | Wintermute | 96/51 |
| 1,869,335 A | 7/1932 | Day | 95/77 |
| 2,327,588 A | 8/1943 | Bennett | 315/326 |
| 2,359,057 A | 9/1944 | Skinner | 96/224 |
| 2,509,548 A | 5/1950 | White | 96/82 |
| 2,949,550 A | 8/1960 | Brown | 310/5 |
| 3,018,394 A | 1/1962 | Brown | 310/308 |
| 3,026,964 A | 3/1962 | Penney | 96/74 |
| 3,374,941 A * | 3/1968 | Okress | 315/111.91 |
| 3,518,462 A | 6/1970 | Brown | 310/10 |
| 3,540,191 A | 11/1970 | Herman | 96/51 |
| 3,581,470 A | 6/1971 | Aitkenhead et al. | 96/79 |
| 3,638,058 A | 1/1972 | Fritzius | 313/359.1 |
| 3,744,216 A | 7/1973 | Halloran | 96/16 |
| 3,981,695 A | 9/1976 | Fuchs | 96/77 |
| 3,984,215 A | 10/1976 | Zucker | 95/81 |
| 4,052,177 A | 10/1977 | Kide | 55/139 |
| 4,092,134 A | 5/1978 | Kikuchi | 96/51 |
| 4,102,654 A | 7/1978 | Pellin | 96/16 |
| 4,138,233 A | 2/1979 | Masuda | 55/139 |
| 4,209,306 A | 6/1980 | Feldman et al. | 55/2 |
| 4,227,894 A | 10/1980 | Proynoff | 96/58 |
| 4,231,766 A | 11/1980 | Spurgin | 55/138 |
| 4,232,355 A | 11/1980 | Finger et al. | 361/235 |
| 4,244,710 A | 1/1981 | Burger | 95/69 |
| 4,244,712 A | 1/1981 | Tongret | 55/124 |
| 4,253,852 A | 3/1981 | Adams | 96/58 |
| 4,259,452 A | 3/1981 | Yukuta et al. | 521/52 |
| 4,266,948 A | 5/1981 | Teague et al. | 55/126 |
| 4,282,014 A | 8/1981 | Winkler et al. | 55/105 |
| 4,284,420 A | 8/1981 | Borysiak | 55/114 |
| 4,318,718 A | 3/1982 | Utsumi et al. | 96/51 |
| 4,342,571 A | 8/1982 | Hayashi | 55/137 |
| 4,357,150 A | 11/1982 | Masuda et al. | 95/63 |
| 4,386,395 A | 5/1983 | Francis, Jr. | 363/27 |
| 4,413,225 A | 11/1983 | Donig et al. | 323/246 |
| 4,445,911 A | 5/1984 | Lind | 55/2 |
| 4,477,263 A | 10/1984 | Shaver et al. | 95/7 |
| 4,496,375 A | 1/1985 | Le Vantine | 96/66 |
| 4,502,002 A | 2/1985 | Ando | 323/237 |
| 4,509,958 A | 4/1985 | Masuda et al. | 96/60 |
| 4,516,991 A | 5/1985 | Kawashima | 96/55 |
| 4,536,698 A | 8/1985 | Shevalenko et al. | 323/237 |
| 4,587,475 A | 5/1986 | Finney, Jr. et al. | 323/241 |
| 4,600,411 A | 7/1986 | Santamaria | 55/139 |
| 4,601,733 A | 7/1986 | Ordines et al. | 55/139 |
| 4,626,261 A | 12/1986 | Jorgensen | 55/2 |
| 4,643,745 A | 2/1987 | Sakakibara et al. | 96/76 |
| 4,659,342 A | 4/1987 | Lind | 95/5 |
| 4,674,003 A | 6/1987 | Zylka | 361/235 |
| 4,686,370 A | 8/1987 | Blach | 250/423 R |
| 4,689,056 A | 8/1987 | Noguchi et al. | 96/79 |
| 4,694,376 A | 9/1987 | Gesslauer | 361/235 |
| 4,713,093 A | 12/1987 | Hansson | 55/139 |
| 4,713,724 A | 12/1987 | Voelkel | 361/231 |
| 4,726,812 A | 2/1988 | Hirth | 95/80 |
| 4,726,814 A | 2/1988 | Weitman | 95/73 |
| 4,772,297 A | 9/1988 | Anzai | 96/19 |
| 4,779,182 A | 10/1988 | Mickal et al. | 363/37 |
| 4,781,736 A | 11/1988 | Cheney et al. | 96/60 |
| 4,786,844 A | 11/1988 | Farrell et al. | 315/111.21 |
| 4,789,801 A | 12/1988 | Lee | 310/308 |
| 4,808,200 A | 2/1989 | Dallhammer et al. | 55/105 |
| 4,811,159 A | 3/1989 | Foster, Jr. | 361/212 |
| 4,940,470 A | 7/1990 | Jaisinghani et al. | 55/2 |
| 4,941,068 A | 7/1990 | Hofmann | 361/231 |
| 4,955,991 A | 9/1990 | Torok et al. | 96/50 |
| 4,967,119 A | 10/1990 | Torok et al. | 315/111.91 |
| 4,976,752 A | 12/1990 | Torok et al. | 96/43 |
| D315,598 S | 3/1991 | Yamamoto et al. | D23/381 |
| 5,006,761 A | 4/1991 | Torok et al. | 315/111.91 |
| 5,010,869 A | 4/1991 | Lee | 123/539 |
| 5,012,093 A | 4/1991 | Shimizu | 399/100 |
| 5,012,159 A | 4/1991 | Torok et al. | 315/111.91 |
| 5,024,685 A | 6/1991 | Torok et al. | 96/43 |
| 5,053,912 A | 10/1991 | Loreth et al. | 361/230 |
| 5,077,500 A | 12/1991 | Torok et al. | 315/111.91 |
| RE33,927 E | 5/1992 | Fuzimura | 95/74 |
| 5,141,529 A | 8/1992 | Oakley et al. | 95/57 |
| D329,284 S | 9/1992 | Patton | D23/378 |
| D332,655 S | 1/1993 | Lytle et al. | D23/378 |
| 5,180,404 A | 1/1993 | Loreth et al. | 96/56 |
| 5,183,480 A | 2/1993 | Raterman et al. | 96/62 |
| 5,196,171 A | 3/1993 | Peltier | 422/121 |
| 5,215,558 A | 6/1993 | Moon | 96/62 |
| 5,217,504 A | 6/1993 | Johansson | 55/2 |
| 5,248,324 A | 9/1993 | Hara | 96/37 |
| 5,266,004 A | 11/1993 | Tsumurai et al. | 416/100 |
| 5,290,343 A | 3/1994 | Morita et al. | 96/39 |
| 5,296,019 A | 3/1994 | Oakley et al. | 96/95 |
| 5,302,190 A | 4/1994 | Williams | 95/57 |
| 5,315,838 A | 5/1994 | Thompson | 62/129 |
| 5,316,741 A | 5/1994 | Sewell et al. | 422/186.21 |
| 5,378,978 A | 1/1995 | Gallo et al. | 323/241 |
| 5,435,817 A | 7/1995 | Davis et al. | 55/337 |
| 5,437,713 A | 8/1995 | Chang | 96/51 |
| 5,484,472 A | 1/1996 | Weinberg | 96/26 |
| 5,532,798 A | 7/1996 | Nakagami et al. | 399/170 |
| 5,535,089 A | 7/1996 | Ford et al. | 361/231 |
| D375,546 S | 11/1996 | Lee | D23/364 |
| 5,578,112 A | 11/1996 | Krause | 96/24 |
| D377,523 S | 1/1997 | Marvin et al. | D23/364 |
| 5,601,636 A | 2/1997 | Glucksman | 96/63 |
| 5,641,342 A | 6/1997 | Smith et al. | 96/77 |
| 5,656,063 A | 8/1997 | Hsu | 95/58 |
| 5,667,564 A | 9/1997 | Weinberg | 96/58 |
| 5,669,963 A | 9/1997 | Horton et al. | 96/77 |
| 5,698,164 A | 12/1997 | Kishioka et al. | 422/121 |
| 5,702,507 A | 12/1997 | Wang | 96/55 |
| D389,567 S | 1/1998 | Gudefin | D23/378 |
| 5,766,318 A | 6/1998 | Loreth et al. | 96/69 |
| 5,779,769 A | 7/1998 | Jiang | 96/55 |
| 5,814,135 A | 9/1998 | Weinberg | 96/58 |
| 5,879,435 A | 3/1999 | Satyapal et al. | 96/16 |
| 5,893,977 A | 4/1999 | Pucci | 210/739 |
| 5,911,957 A | 6/1999 | Khatchatrian et al. | 422/186.07 |
| 5,972,076 A | 10/1999 | Nichols et al. | 95/81 |
| 5,975,090 A | 11/1999 | Taylor et al. | 132/116 |
| 5,980,614 A | 11/1999 | Loreth et al. | 96/63 |
| 5,993,521 A | 11/1999 | Loreth et al. | 96/69 |
| 5,997,619 A | 12/1999 | Knuth et al. | 96/224 |
| 6,019,815 A | 2/2000 | Satyapal et al. | 95/74 |
| 6,042,637 A | 3/2000 | Weinberg | 96/58 |
| 6,063,168 A | 5/2000 | Nichols et al. | 96/80 |
| 6,086,657 A | 7/2000 | Freije | 95/2 |
| 6,117,216 A | 9/2000 | Loreth | 96/62 |
| 6,118,645 A | 9/2000 | Partridge | 361/231 |
| 6,126,722 A | 10/2000 | Mitchell et al. | 95/57 |
| 6,126,727 A | 10/2000 | Lo | 96/39 |
| 6,149,717 A * | 11/2000 | Satyapal et al. | 96/16 |
| 6,149,815 A | 11/2000 | Sauter | 210/635 |
| 6,152,146 A | 11/2000 | Taylor et al. | 132/116 |
| 6,163,098 A | 12/2000 | Taylor et al. | 310/308 |
| 6,176,977 B1 | 1/2001 | Taylor et al. | 204/176 |
| 6,182,461 B1 | 2/2001 | Washburn et al. | 62/264 |
| 6,182,671 B1 | 2/2001 | Taylor et al. | 132/116 |
| 6,193,852 B1 | 2/2001 | Caracciolo et al. | 204/176 |
| 6,203,600 B1 | 3/2001 | Loreth | 96/40 |
| 6,212,883 B1 | 4/2001 | Kang | 60/275 |
| 6,228,149 B1 | 5/2001 | Alenichev et al. | 95/78 |
| 6,252,012 B1 | 6/2001 | Egitto et al. | 525/431 |

| | | | |
|---|---|---|---|
| 6,270,733 B1 | 8/2001 | Rodden | 422/186.07 |
| 6,277,248 B1 | 8/2001 | Ishioka et al. | 204/176 |
| 6,282,106 B2 | 8/2001 | Grass | 363/37 |
| D449,097 S | 10/2001 | Smith et al. | D23/364 |
| D449,679 S | 10/2001 | Smith et al. | D23/365 |
| 6,302,944 B1 | 10/2001 | Hoenig | 96/16 |
| 6,309,514 B1 | 10/2001 | Conrad et al. | 204/164 |
| 6,312,507 B1 | 11/2001 | Taylor et al. | 96/19 |
| 6,315,821 B1 | 11/2001 | Pillion et al. | 96/416 |
| 6,328,791 B1 | 12/2001 | Pillion et al. | 96/418 |
| 6,348,103 B1 | 2/2002 | Ahlborn et al. | 134/6 |
| 6,350,417 B1 | 2/2002 | Lau et al. | 422/186.04 |
| 6,362,604 B1 | 3/2002 | Cravey | 323/241 |
| 6,372,097 B1 | 4/2002 | Chen | 204/176 |
| 6,373,723 B1 | 4/2002 | Wallgren et al. | 363/16 |
| 6,379,427 B1 | 4/2002 | Siess | 95/57 |
| 6,391,259 B1 | 5/2002 | Malkin et al. | 422/28 |
| 6,398,852 B1 | 6/2002 | Loreth | 96/63 |
| 6,447,587 B1 | 9/2002 | Pillion et al. | 96/418 |
| 6,464,754 B1 | 10/2002 | Ford | 95/26 |
| 6,471,753 B1 | 10/2002 | Ahn et al. | 96/27 |
| 6,494,940 B1 * | 12/2002 | Hak | 96/224 |
| 6,504,308 B1 | 1/2003 | Krichtafovitch et al. | 315/111.91 |
| 6,508,982 B1 | 1/2003 | Shoji | 422/22 |
| 6,603,268 B2 | 8/2003 | Lee | 315/111.01 |
| 6,613,277 B1 | 9/2003 | Monagan | 422/24 |
| 6,635,105 B2 | 10/2003 | Ahlborn et al. | 96/28 |
| 2001/0048906 A1 | 12/2001 | Lau et al. | |
| 2002/0069760 A1 | 6/2002 | Pruette et al. | |
| 2002/0144601 A1 | 10/2002 | Palestro et al. | |
| 2002/0152890 A1 | 10/2002 | Leiser | |
| 2002/0170435 A1 | 11/2002 | Joannou | |
| 2002/0190658 A1 | 12/2002 | Lee | |
| 2002/0195951 A1 | 12/2002 | Lee | |
| 2003/0005824 A1 | 1/2003 | Katou et al. | |
| 2004/0052700 A1 | 3/2004 | Kotlyar et al. | |
| 2004/0065202 A1 | 4/2004 | Gatchell et al. | |
| 2004/0136863 A1 | 7/2004 | Yates et al. | 422/4 |
| 2004/0166037 A1 | 8/2004 | Youdell et al. | 422/186.3 |

FOREIGN PATENT DOCUMENTS

| | | |
|---|---|---|
| CN | 2138764 Y | 7/1993 |
| CN | 2153231 Y | 1/1994 |
| DE | 2206057 | 8/1973 |
| EP | 0433152 A1 | 12/1990 |
| EP | 0332624 B1 | 1/1992 |
| FR | 2690509 | 10/1993 |
| GB | 643363 | 9/1950 |
| JP | S51-90077 | 8/1976 |
| JP | S62-20653 | 2/1987 |
| JP | 10137007 | 5/1998 |
| JP | 11104223 | 4/1999 |
| JP | 2000236914 | 9/2000 |
| WO | WO92/05875 A1 | 4/1992 |
| WO | WO96/04703 A1 | 2/1996 |
| WO | WO99/07474 A1 | 2/1999 |
| WO | WO00/10713 A1 | 3/2000 |
| WO | WO 01/47803 A1 | 7/2001 |
| WO | WO 01/48781 A1 | 7/2001 |
| WO | WO01/64349 A1 | 9/2001 |
| WO | WO01/85348 A2 | 11/2001 |
| WO | WO02/20162 A2 | 3/2002 |
| WO | WO02/20163 A2 | 3/2002 |
| WO | WO02/30574 A1 | 4/2002 |
| WO | WO02/32578 A1 | 4/2002 |
| WO | WO02/42003 A1 | 5/2002 |
| WO | WO02/066167 A1 | 8/2002 |
| WO | WO03/009944 A1 | 2/2003 |
| WO | WO03/013620 A1 | 2/2003 |
| WO | WO03/013734 A1 | 2/2003 |

OTHER PUBLICATIONS

Trion Console 250 Electronic Air Cleaner, Model Series 442857 and 445600, Manual for Installation–Operation–Maintenance, Trion Inc., 7 pp., believed to be at least one year prior to Nov. 5, 1998.

Trion 350 Air Purifier, Model 450111–010, http://www.feddersoutlet.com/trion350.html, 12 pp., believed to be at least one year prior to Nov. 5, 1998.

Trion 150 Air Purifier, Model 45000–002, http://www.feddersoutlet.com/trion150.html, 11 pp., believed to be at least one year prior to Nov. 5, 1998.

Trion 120 Air Purifier, Model 442501–025, http://www.feddersoutled.com/trion120.html, 16 pp., believed to be at least one year prior to Nov. 5, 1998.

Friedrich C–90A Electronic Air Cleaner, Service Information, Friedrich Air Conditioning Co., 12 pp., 1985.

LakeAir Excel and Maxum Portable Electronic Air Cleaners, Operating and Service Manual, LakeAir International, Inc., 11 pp., 1971.

Blueair AV 402 Air Purifier, http://www.air–purifiers–usa.biz/Blueair_AV402.htm, 4 pp., 1996.

Blueair AV 501 Air Purifier, http://www.air–purifiers–usa.biz/Blueair_AV501.htm, 15 pp., 1997.

U.S. Appl. No. 10/278,193, filed Oct. 21, 2002, Reeves.
U.S. Appl. No. 10/405,193, filed Apr. 1, 2003, Taylor.
U.S. Appl. No. 09/197,131, filed Nov. 20, 1998, Taylor et al.
U.S. Appl. No. 10/023,197, filed Dec. 13, 2001, Taylor et al.
U.S. Appl. No. 10/023,460, filed Dec. 13, 2001, Taylor et al.
U.S. Appl. No. 10/074,209, filed Feb. 12, 2002, Taylor et al.
U.S. Appl. No. 10/074,207, filed Feb. 12, 2002, Taylor et al.
U.S. Appl. No. 10/074,208, filed Feb. 12, 2002, Taylor.
U.S. Appl. No. 10/074,339, filed Feb. 12, 2002, Taylor et al.
U.S. Appl. No. 10/074,827, filed Feb. 12, 2002, McKinney, Jr., et al.
U.S. Appl. No. 10/074,549, filed Feb. 12, 2002, Sinaiko et al.
U.S. Appl. No. 10/074,103, filed Feb. 12, 2002, Sinaiko et al.
U.S. Appl. No. 10/074,096, filed Feb. 12, 2002, Taylor et al.
"Zenion Elf Device", drawing, prior art, 1 page.
Electrical Schematic and promotional material available from Zenion Industries, 7 pages, Aug. 1990.
Promotional material available from Zenion Industries for the Plasma–Pure 100/200/300, 2 pages, Aug. 1990.
Promotional material available from Zenion Industries for the Plasma–Tron, 2 pages, Aug. 1990.
U.S. Appl. No. 09/669,253, filed Sep. 25, 2000, Taylor et al.
U.S. Appl. No. 09/669,268, filed Sep. 25, 2002, Taylor et al.
U.S. Appl. No. 09/730,499, filed Dec. 5, 2000, Taylor et al.
U.S. Appl. No. 09/742,814, filed Dec. 19, 2000, Taylor et al.
U.S. Appl. No. 09/924,624, filed Aug. 8, 2001, Taylor et al.
U.S. Appl. No. 09/924,600, filed Aug. 8, 2001, Taylor et al.
U.S. Appl. No. 60/341,179, filed Dec. 13, 2001, Taylor et al.
U.S. Appl. No. 60/340,702, filed Dec. 13, 2001, Taylor et al.
U.S. Appl. No. 60/341,377, filed Dec. 13, 2001, Taylor et al.
U.S. Appl. No. 60/341,518, filed Dec. 13, 2001, Taylor.
U.S. Appl. No. 60/340,288, filed Dec. 13, 2001, Taylor.
U.S. Appl. No. 60/341,176, filed Dec. 13, 2001, Taylor.
U.S. Appl. No. 60/340,462, filed Dec. 13, 2001, Taylor.
U.S. Appl. No. 60/341,090, filed Dec. 13, 2001, Taylor.

U.S. Appl. No. 60/341,433, filed Dec. 13, 2001, Taylor.
U.S. Appl. No. 60/341,592, filed Dec. 13, 2001, Taylor.
U.S. Appl. No. 60/341,320, filed Dec. 13, 2001, Taylor.
U.S. Appl. No. 10/074,082, filed Feb. 12, 2002, Taylor et al.
U.S. Appl. No. 10/156,158, filed May 28, 2002, Taylor et al.
U.S. Appl. No. 60/391,070, filed Jun. 6, 2002, Reeves.
U.S. Appl. No. 10/188,668, filed Jul. 2, 2002, Taylor et al.

LENTEK Silā™ Plug–In Air Purifier/Deodorizer product box copyrighted 1999.

* cited by examiner

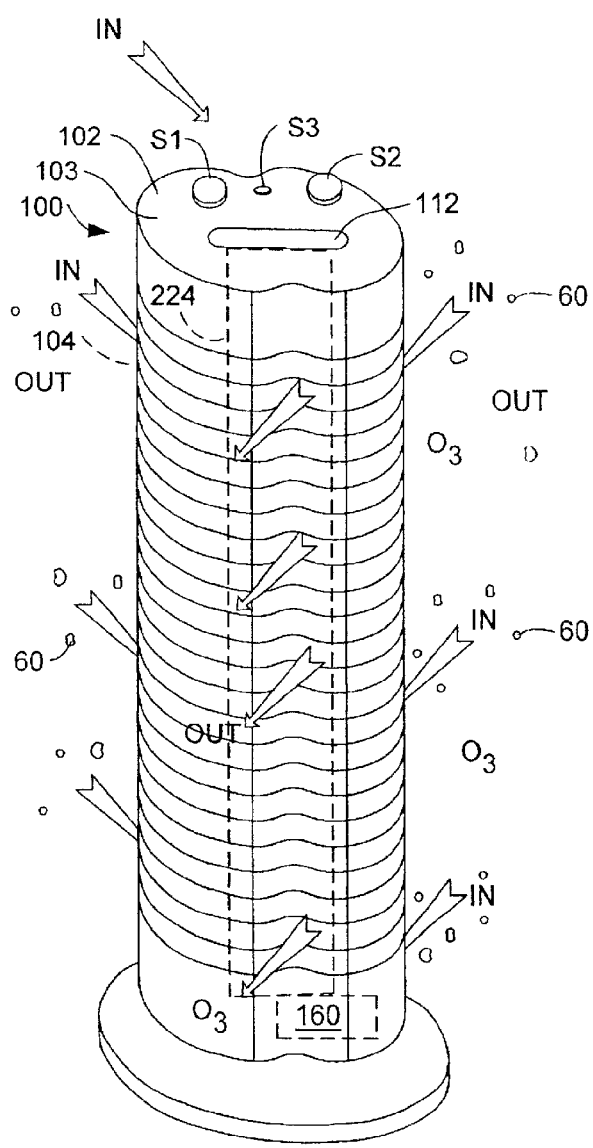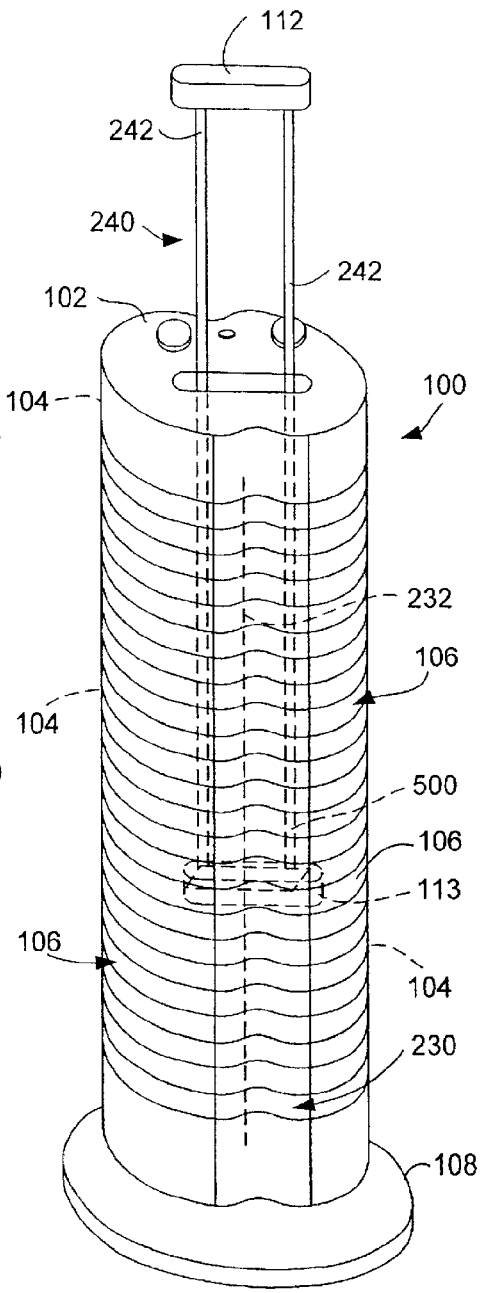
FIG. - 2A
FIG. - 2B

ELECTRO-KINETIC AIR TRANSPORTER AND CONDITIONER DEVICE WITH ENHANCED ANTI-MICROORGANISM CAPABILITY

CLAIM OF PRIORITY

This application claims priority from provisional application entitled "ELECTRO-KINETIC AIR TRANSPORTER AND CONDITIONER DEVICE WITH ENHANCED ANTI-MICROORGANISM CAPABILITY," application Ser. No. 60/341,179, filed Dec. 13, 2001 under 35 U.S.C. 119(e), which application is incorporated herein by reference. This application claims priority from provisional application entitled "FOCUS ELECTRODE, ELECTRO-KINETIC AIR TRANSPORTER-CONDITIONER DEVICES," application Ser. No. 60/306, 479, filed Jul. 18, 2001 under 35 U.S.C. 119(e), which application is incorporated herein by reference. This application claims priority from and is a continuation-in-part of patent application "ELECTRO-KINETIC DEVICE WITH ENHANCED ANTI-MICROORGANISM CAPABILITY", application Ser. No. 09/774,198, filed Jan. 29, 2001, now U.S. Pat. No. 6,544,485 and incorporated herein by reference. This application claims priority from and is a continuation-in-part of U.S. patent application Ser. No. 09/924,624 filed Aug. 8, 2001 which is a continuation of U.S. patent Ser. No. 09/564,960 filed May 4, 2000, now U.S. Pat. No. 6,350,417, which is a continuation-in-part of U.S. patent application Ser. No. 09/186,471 filed Nov. 5, 1998, now U.S. Pat. No. 6,176,977. This application claims priority from and is a continuation-in-part of U.S. Patent Application Ser. No. 09/730,499, filed Dec. 5, 2000 which is a continuation of U.S. Patent Application Ser. No. 09/186, 471, filed Nov. 5, 1998, now U.S. Pat. No. 6,176,977. All of the above are incorporated herein by reference.

13. U.S. patent application Ser. No. 10/074,082, filed herewith on Feb. 12, 2002, entitled "ELECTRO-KINETIC AIR TRANSPORTER-CONDITIONER DEVICES WITH AN UPSTREAM FOCUS ELECTRODE"; SHPR-01041USL 14. U.S. patent application Ser. No. 10/074,209, filed herewith on Feb. 12, 2002, entitled "ELECTRO-KINETIC AIR TRANSPORTER-CONDITIONER DEVICES WITH TRAILING ELECTRODE"; SHPR-01041USM 15. U.S. patent application Ser. No. 10/074,207, now abandoned filed on Feb. 12, 2002, entitled "ELECTRO-KINETIC AIR TRANSPORTER-CONDITIONER DEVICES WITH INTERSTITIAL ELECTRODE"; SHPR-01041USN 16. U.S. patent application Ser. No. 10/074,208, filed herewith on Feb. 12, 2002, entitled "ELECTRO-KINETIC AIR TRANSPORTER-CONDITIONER DEVICES WITH ENHANCED COLLECTOR ELECTRODE"; SHPR-01041USO 17. U.S. patent application Ser. No. 10/074,339, filed herewith on Feb. 12, 2002, entitled "ELECTRO-KINETIC AIR TRANSPORTER CONDITIONER DEVICES WITH ENHANCED EMITTER ELECTRODE"; SHPR-01041USP 18. U.S. patent application Ser. No. 10/074,347, filed herewith on Feb. 12, 2002, entitled "ELECTRO-KINETIC AIR TRANSPORTER AND CONDITIONER DEVICE WITH ENHANCED HOUSING CONFIGURATION AND ENHANCED ANTI-MICROORGANISM CAPABILITY"; SHPR-01028US5

19. U.S. patent application Ser. No. 10/074,379, filed herewith on Feb. 12, 2002, entitled"ELECTRO-KINETIC AIR TRANSPORTER AND CONDITIONER DEVICE WITH ENHANCED MAINTENANCE FEATURES AND ENHANCED ANTI-MICROORGANISM CAPABILITY"; SHPR-01028US6

20. U.S. patent application Ser. No. 10/074,827, filed herewith on Feb. 12, 2002, entitled "ELECTRO-KINETIC AIR TRANSPORTER-CONDITIONER WITH NON-EQUIDISTANT COLLECTOR ELECTRODES"; SHPR-01041USQ 21. U.S. patent application Ser. No. 10/074,549, filed herewith on Feb. 12, 2002, entitled "DUAL INPUT AND OUTLET ELECTROSTATIC AIR TRANSPORTER-CONDITIONER"; SHPR-01041USR and 22. U.S. patent application Ser. No. 10/074,103, filed herewith on Feb. 12, 2002, entitled "ELECTRO-KINETIC AIR TRANSPORTER-CONDITIONER DEVICES WITH A ENHANCED COLLECTOR ELECTRODE FOR COLLECTION OF MORE PARTICULATE MATTER"SHPR-01041USS All of the above are incorporated herein by reference.

FIELD OF THE INVENTION

The present invention relates generally to a device that transports and conditions air. More specifically, an embodiment of the present invention provides such a device with the enhanced ability to reduce the number of microorganisms within the air, which microorganisms can include germs, bacteria, and viruses.

BACKGROUND OF THE INVENTION

U.S. Pat. No. 4,789,801 issued to Lee, and incorporated herein by reference, describes various devices to generate a stream of ionized air using an electro-kinetic technique. In overview, electro-kinetic techniques use high electric fields to ionize air molecules, a process that produces ozone ($O_3$) as a byproduct. Ozone is an unstable molecule of oxygen that is commonly produced as a byproduct of high voltage arcing. In appropriate concentrations, ozone can be a desirable and useful substance. But ozone by itself may not be effective to kill microorganisms such as germs, bacteria, and viruses in the environment surrounding the device.

FIG. 1 depicts a generic electro-kinetic device 10 to condition air. Device 10 includes a housing 20 that typically has at least one air input 30 and at least one air output 40. Within housing 20 there is disposed an electrode assembly or system 50 comprising a first electrode array 60 having at least one electrode 70 and comprising a second electrode array 80 having at least one electrode 90. System 10 further includes a high voltage generator 95 coupled between the first and second electrode arrays. As a result, ozone and ionized particles of air are generated within device 10, and there is an electro-kinetic flow of air in the direction from the first electrode array 60 towards the second electrode array 80. In FIG. 1, the large arrow denoted IN represents ambient air that can enter input port 30. The small "x"'s denote particulate matter that may be present in the incoming ambient air. The air movement is in the direction of the large arrows, and the output airflow, denoted OUT, exits device 10 via outlet 40. An advantage of electro-kinetic devices such as device 10 is that an airflow is created without using fans or other moving parts. Thus, device 10 in FIG. 1 can function somewhat as a fan to create an output airflow, but without requiring moving parts.

Preferably particulate matter "x" in the ambient air can be electrostatically attracted to the second electrode array 80, with the result that the outflow (OUT) of air from device 10 not only contains ozone and ionized air, but can be cleaner than the ambient air. In such devices, it can become necessary to occasionally clean the second electrode array electrodes 80 to remove particulate matter and other debris from the surface of electrodes 90. Accordingly, the outflow of air (OUT) is conditioned in that particulate matter is removed and the outflow includes appropriate amounts of ozone, and some ions.

An outflow of air containing ions and ozone may not, however, destroy or significantly reduce microorganisms such as germs, bacteria, fungi, viruses, and the like, collectively hereinafter "microorganisms." It is known in the art to destroy such microorganisms with, by way of example only, germicidal lamps. Such lamps can emit ultra-violet radiation having a wavelength of about 254 nm. For example, devices to condition air using mechanical fans, HEPA filters, and germicidal lamps are sold commercially by companies such as Austin Air, C.A.R.E. 2000, Amaircare, and others. Often these devices are somewhat cumbersome, and have the size and bulk of a small filing cabinet. Although such fan-powered devices can reduce or destroy microorganisms, the devices tend to be bulky, and are not necessarily silent in operation.

U.S. Pat. Nos. 5,879,435, 6,019,815, and 6,149,717, issued to Satyapal et al., and incorporated herein by reference, discloses an electronic air cleaner that contains an electrostatic precipitator cell and a germicidal lamp for use, among other uses, with a forced air furnace system. The electrostatic precipitator cell includes multiple collector plates for collecting particulate material from the airstream. The germicidal lamp is disposed within the air cleaner to irradiate the collector plates and to destroy microbial growth that might occur on the particulate material deposited on the collector plates. Particles that pass through the air cleaner due to the action of the fan of the forced air furnace, and that are not deposited on the collector plates, generally are not subjected to the germicidal radiation for a period of time long enough for the light to substantially reduce microorganisms within the airflow.

What is needed is a device to condition air in a room that can operate relatively silently to remove particulate matter in the air, that can preferably output appropriate amounts of ozone or no ozone, and that can kill or reduce microorganisms such as germs, fungi, bacteria, viruses, and the like contained within the airflow.

SUMMARY OF THE PRESENT INVENTION

Embodiments of the present invention provide devices that fulfill the above described needs. It is an aspect of the present invention to reduce the amount of microorganisms within the airflow. An embodiment of the present invention has an ion generator to create an airflow and collect particulates, and a germicidal lamp to kill microorganisms. The housing is shaped to slow the airflow rate as the airflow passes the germicidal lamp, allowing a longer dwell time of the air in front of the germicidal lamp.

An aspect of the invention includes the germicidal lamp located upstream of the ion generator. An embodiment of the invention locates the germicidal lamp within the housing to maximize the amount of air irradiated, and to minimize the disturbance the lamp housing will cause to the airflow rate of the device. Another embodiment maximizes the amount of germicidal light that will directly shine on the airflow, without having to be reflected.

Another aspect of the present invention ensures that there is no direct line-of-sight through the air inlet or the air outlet of the housing to the germicidal lamp. An embodiment of the present invention has vertical fins covering the air inlet and air outlet to prohibit an individual from directly staring at the germicidal radiation emitted by the lamp. Another embodiment includes a shell or lamp housing that substantially surrounds the germicidal lamp to direct the radiation away from the air inlet, and the air outlet.

Another feature of an embodiment of the invention includes the ease of removeability of electrodes from the ion generator and ease of replacement of the germicidal lamp. An embodiment of the invention includes a rear panel that can be removed to expose the germicidal lamp for replacing. Another embodiment of the invention has second electrodes and a germicidal lamp that can be removed through the top of the housing for cleaning and/or replacement.

Other features and advantages of the invention will appear from the following description in which the preferred embodiments have been set forth in detail, in conjunction with the accompanying drawings and claims.

BRIEF DESCRIPTION OF THE FIGURES

FIGS. 2A–2B; FIG. 2A is a perspective view of an embodiment of the housing for the present invention; FIG. 2B is a perspective view of the embodiment shown in FIG. 2A, illustrating the removable array of second electrodes;

FIG. 3A is a perspective view of an embodiment of the present invention without a base; FIG. 3B is a top view of the embodiment of the present invention illustrated in FIG. 3A; FIG. 3C is a partial perspective view of the embodiment shown in FIGS. 3A–3B, illustrating there movable second array of electrodes; FIG. 3D is a side view of the embodiment of the present invention of FIG. 3A including a base; FIG. 3E is a perspective view of the embodiment in FIG. 3D, illustrating a removable rear panel which exposes a germicidal lamp;

FIG. 5A is atop, partial cross-sectioned view of an embodiment of the present invention, illustrating one configuration of the germicidal lamp; FIG. 5B is a top, partial cross-sectioned view of another embodiment of the present invention, illustrating another configuration of the germicidal lamp;

FIG. 7A is a partial electrical block diagram of an embodiment of the circuit of the present invention; FIG. 7B is a partial electrical block diagram of the embodiment of the present invention for use with the circuit depicted in FIG. 7A;

FIG. 8A is a perspective view showing an embodiment of an electrode assembly, according to the present invention; FIG. 8B is a plan view of the embodiment illustrated in FIG. 8A; FIG. 8C is a perspective view showing another embodiment of an electrode assembly, according to the present invention; FIG. 8D is a plan view illustrating a modified version of the embodiment shown in FIG. 8C; FIG. 8E is a perspective view showing yet another embodiment of an electrode assembly according to the present invention; FIG. 8F is a plan view of the embodiment shown in FIG. 8E;

FIG. 9A is a perspective view of still another embodiment of the present invention; FIG. 9B is a plan view of a modified embodiment of that shown in FIG. 9A;

FIG. 10A is a perspective view of another embodiment of the present invention; FIG. 10B is a perspective view of a modified embodiment of that shown in FIG. 10A; FIG. 10C is a perspective view of a modified embodiment of that shown in FIG. 10B; FIG. 10D is a modified embodiment of that shown in FIG. 8D;

FIG. 11A is a perspective view of yet another embodiment of the present invention; FIG. 11B is a perspective view of a modified embodiment of that shown in FIG. 11A; FIG. 11C is a perspective view of a modified embodiment of that shown in FIG. 11B;

FIG. 12A is a perspective view of still another embodiment of the present invention; FIG. 12B is a perspective view of a modified embodiment of that shown in FIG. 9A; FIG. 12C is a perspective view of a modified embodiment of that shown in FIG. 12A;

FIG. 13A is a perspective view of another embodiment of the present invention; FIG. 13B is a plan view of the embodiment shown in FIG. 13A; FIG. 13C is a plan view of still another embodiment of the present invention;

FIG. 14A is a plan view of still another embodiment of the present invention; FIG. 14B is a plan view of a modified embodiment of that shown in FIG. 14A; FIG. 14C is a plan view of yet another embodiment of the present invention; FIG. 14D is a plan view of a modified embodiment of that shown in FIG. 14C; FIG. 14E is a plan view of another embodiment of the present invention; FIG. 14F is a plan view of a modified embodiment of that shown in FIG. 14E; FIG. 15A is perspective view of another embodiment of the present invention; FIG. 15B is a perspective view of still another embodiment of the present invention; FIG. 15C is a perspective view of yet another embodiment of the present invention.

DETAILED DESCRIPTION OF THE PREFERRED EMBODIMENT

Figure 1:
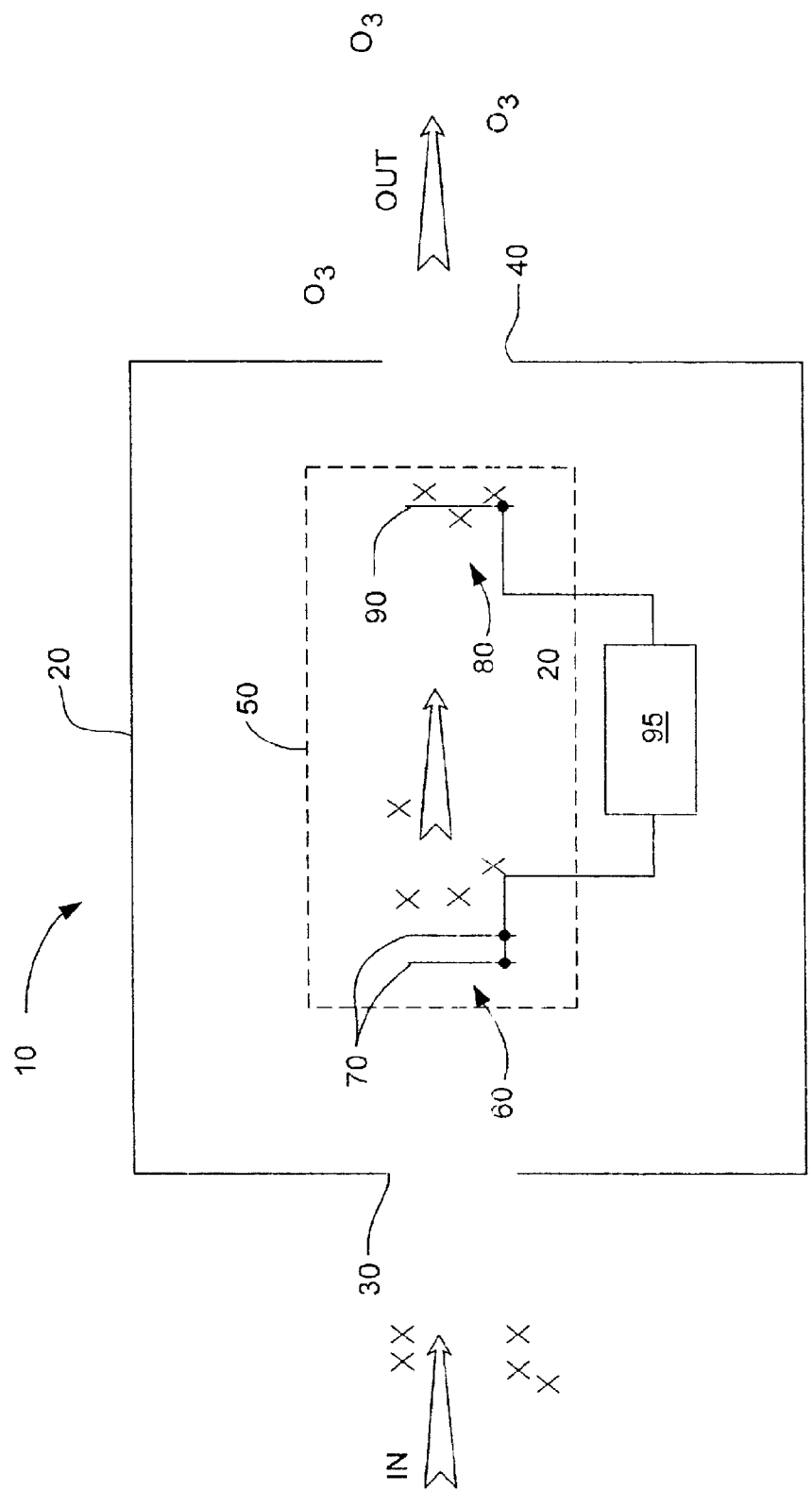
FIG. 1 depicts a generic electro-kinetic conditioner device that outputs ionized air and ozone, according to the prior art.

Overall Air Transporter-Conditioner System Configuration: FIGS. 2A–2B

FIGS. 2A–2B depicts a system which does not have incorporated therein a germicidal lamp. However, these embodiments do include other aspects such as the removable second electrodes which can be included in the other described embodiments.

FIGS. 2A and 2B depict an electro-kinetic air transporter-conditioner system 100 whose housing 102 includes preferably rear-located intake vents or louvers 104 and preferably front located exhaust vents 106, and a base pedestal 108. Preferably, the housing 102 is free standing and/or upstandingly vertical and/or elongated. Internal to the transporter housing 102 is an ion generating unit 160, preferably powered by an AC:DC power supply that is energizable or excitable using switch S1. Switch S1, along with the other below described user operated switches, are conveniently located at the top 103 of the unit 100. Ion generating unit 160 is self-contained in that other ambient air, nothing is required from beyond the transporter housing 102, save external operating potential, for operation of the present invention.

The upper surface 103 of the housing 102 includes a user-liftable handle member 112 to which is affixed a second array 240 of collector electrodes 242. The housing 102 also encloses a first array of emitter electrodes 230, or a single first emitter electrode shown here as a single wire or wire-shaped electrode 232. (The terms "wire" and "wire-shaped" shall be used interchangeably herein to mean an electrode either made from a wire or, if thicker or stiffer than a wire, having the appearance of a wire.) In the embodiment shown, handle member 112 lifts second array electrodes 240 upward causing the second electrode to telescope out of the top of the housing and, if desired, out of unit 100 for cleaning, while the first electrode array 230 remains within unit 100. As is evident from the figure, the second array of electrodes 240 can be lifted vertically out from the top 103 of unit 100 along the longitudinal axis or direction of the elongated housing 102. This arrangement with the second electrodes removable from the top 103 of the unit 100, makes it easy for the user to pull the second electrodes 242 out for cleaning. In FIG. 2B, the bottom ends of second electrodes 242 are connected to a member 113, to which is attached a mechanism 500, which includes a flexible member and a slot for capturing and cleaning the first electrode 232, whenever handle member 112 is moved upward or downward by a user. The first and second arrays of electrodes are coupled to the output terminals of ion generating unit 160.

The general shape of the embodiment of the invention shown in FIGS. 2A and 2B is that of a figure eight in cross-section, although other shapes are within the spirit and scope of the invention. The top-to-bottom height in one preferred embodiment is, 1 m, with a left-to-right width of preferably 15 cm, and a front-to-back depth of perhaps 10 cm, although other dimensions and shapes can of course be used. A louvered construction provides ample inlet and outlet venting in an ergonomical housing configuration. There need be no real distinction between vents 104 and 106, except their location relative to the second electrodes. These vents serve to ensure that an adequate flow of ambient air can be drawn into or made available to the unit 100, and that an adequate flow of ionized air that includes appropriate amounts of $O_3$ flows out from unit 100.

As will be described, when unit 100 is energized by depressing switch S1, high voltage or high potential output by an ion generator 160 produces ions at the first electrode 232, which ions are attracted to the second electrodes 242. The movement of the ions in an "IN" to "OUT" direction carries with the ions air molecules, thus electro-kinetically producing an outflow of ionized air. The "IN" rotation in FIGS. 2A and 2B denote the intake of ambient air with particulate matter 60. The "OUT" notation in the figures denotes the outflow of cleaned air substantially devoid of the particulate matter, which particulates matter adheres electrostatically to the surface of the second electrodes. In the process of generating the ionized airflow appropriate amounts of ozone ($O_3$) are beneficially produced. It may be desired to provide the inner surface of housing 102 with an electrostatic shield to reduce detectable electromagnetic radiation. For example, a metal shield could be disposed within the housing, or portions of the interior of the housing can be coated with a metallic paint to reduce such radiation.

Preferred Embodiments of Air-Transporter-Conditioner System with Germicidal Lamp FIGS. 3A–6 depict various embodiments of the device 200, with an improved ability to diminish or destroy microorganisms including bacteria, germs, and viruses. Specifically, FIGS. 3A–6 illustrate various preferred embodiments of the elongated and upstanding housing 210 with the operating controls located on the top surface 217 of the housing 210 for controlling the device 200.

FIGS. 3A–3E

Figure 3A:
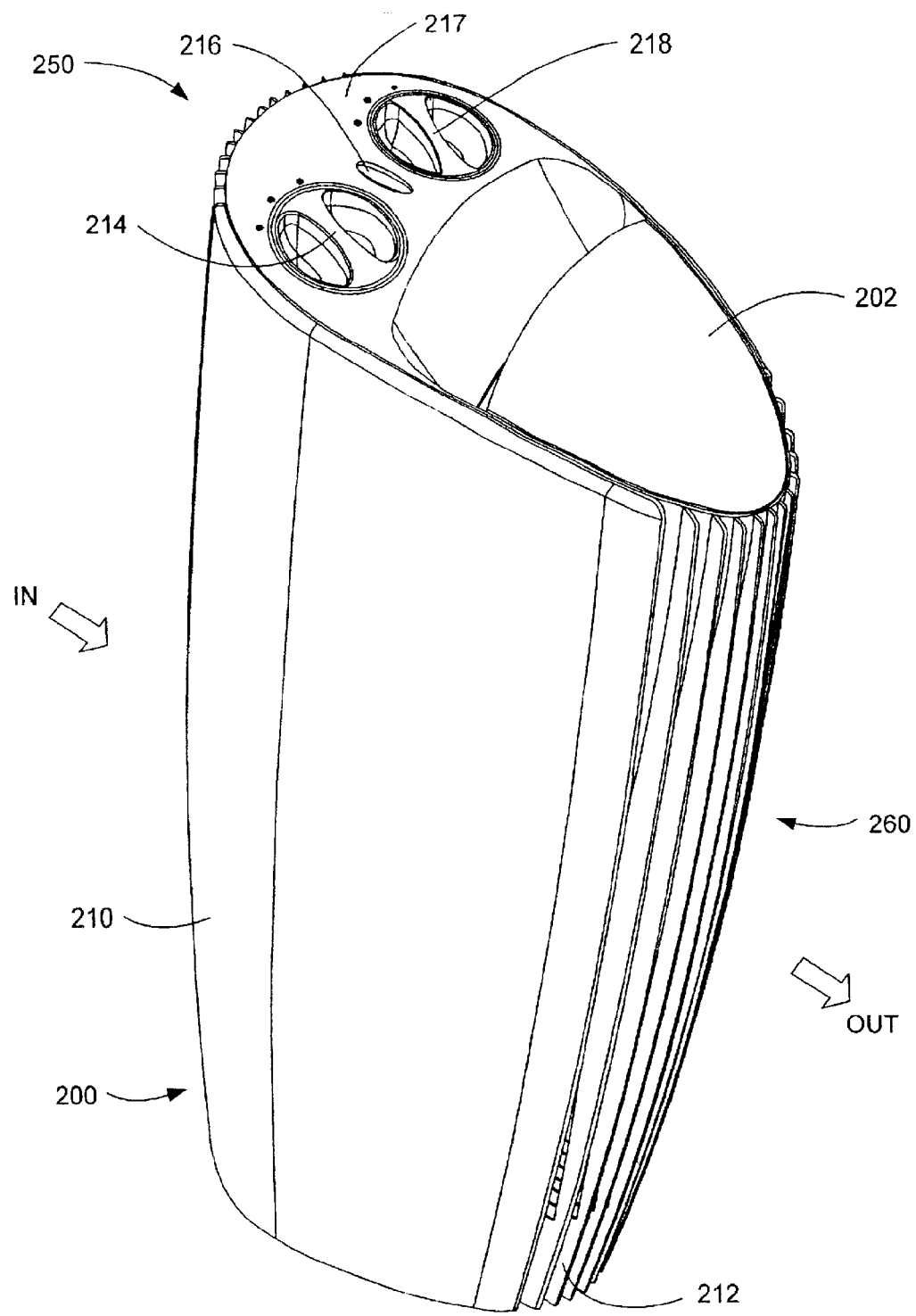
FIGS. 3A–3E.

FIG. 3A illustrates a first preferred embodiment of the housing 210 of device 200. The housing 210 is preferably made from a lightweight inexpensive material, ABS plastic for example. As a germicidal lamp (described hereinafter) is located within the housing 210, the material must be able to withstand prolonged exposure to class UV-C light. Non "hardened" material will degenerate over time if exposed to light such as UV-C. By way of example only, the housing 210 may be manufactured from CYCLOLAC® ABS Resin, (material designation VW300(f2)) which is manufactured by General Electric Plastics Global Products, and is certified by UL Inc. for use with ultraviolet light. It is within the scope of the present invention to manufacture the housing 210 from other UV appropriate materials.

In a preferred embodiment, the housing 210 is aerodynamically oval, elliptical, teardrop-shaped or egg-shaped. The housing 210 includes at least one air intake 250, and at least one air outlet 260. As used herein, it will be understood that the intake 250 is "upstream" relative to the outlet 260, and that the outlet 260 is "downstream" from the intake 250. "Upstream" and "downstream" describe the general flow of air into, through, and out of device 200, as indicated by the large hollow arrows.

Covering the inlet 250 and the outlet 260 are fins, louvers, or baffles 212. The fins 212 are preferably elongated and upstanding, and thus in the preferred embodiment, vertically oriented to minimize resistance to the airflow entering and exiting the device 200. Preferably the fins 212 are vertical and parallel to at least the second collector electrode array 240 (see FIG. 5A). The fins 212 can also be parallel to the first emitter electrode array 230. This configuration assists in the flow of air through the device 200 and also assists in preventing U radiation from the UV or germicidal lamp 290 (described hereinafter), or other germicidal source, from exiting the housing 210. By way of example only, if the long width of the body from the inlet 250 to the outlet 260 is 8 inches, the collector electrode 242 (see FIG. 5A) can be 1¼" wide in the direction of airflow, and the fins 212 can be ¾" or ½" wide in the direction airflow. Of course, other proportionate dimensions are within the spirit and scope of the invention. Further, other fin and housing shapes which may not be as aerodynamic are within the spirit and scope of the invention.

From the above it is evident that preferably the cross-section of the housing 210 is oval, elliptical, teardrop-shaped or egg shaped with the inlet 250 and outlet 260 narrower than the middle (see line A—A in FIG. 5A) of the housing 210. Accordingly, the airflow, as it passes across line A—A, is slower due to the increased width and area of the housing 210. Any bacteria, germs, or virus within the airflow will have a greater dwell time and be neutralized by a germicidal device, such as, preferably, an ultraviolet lamp.

Figure 3B:
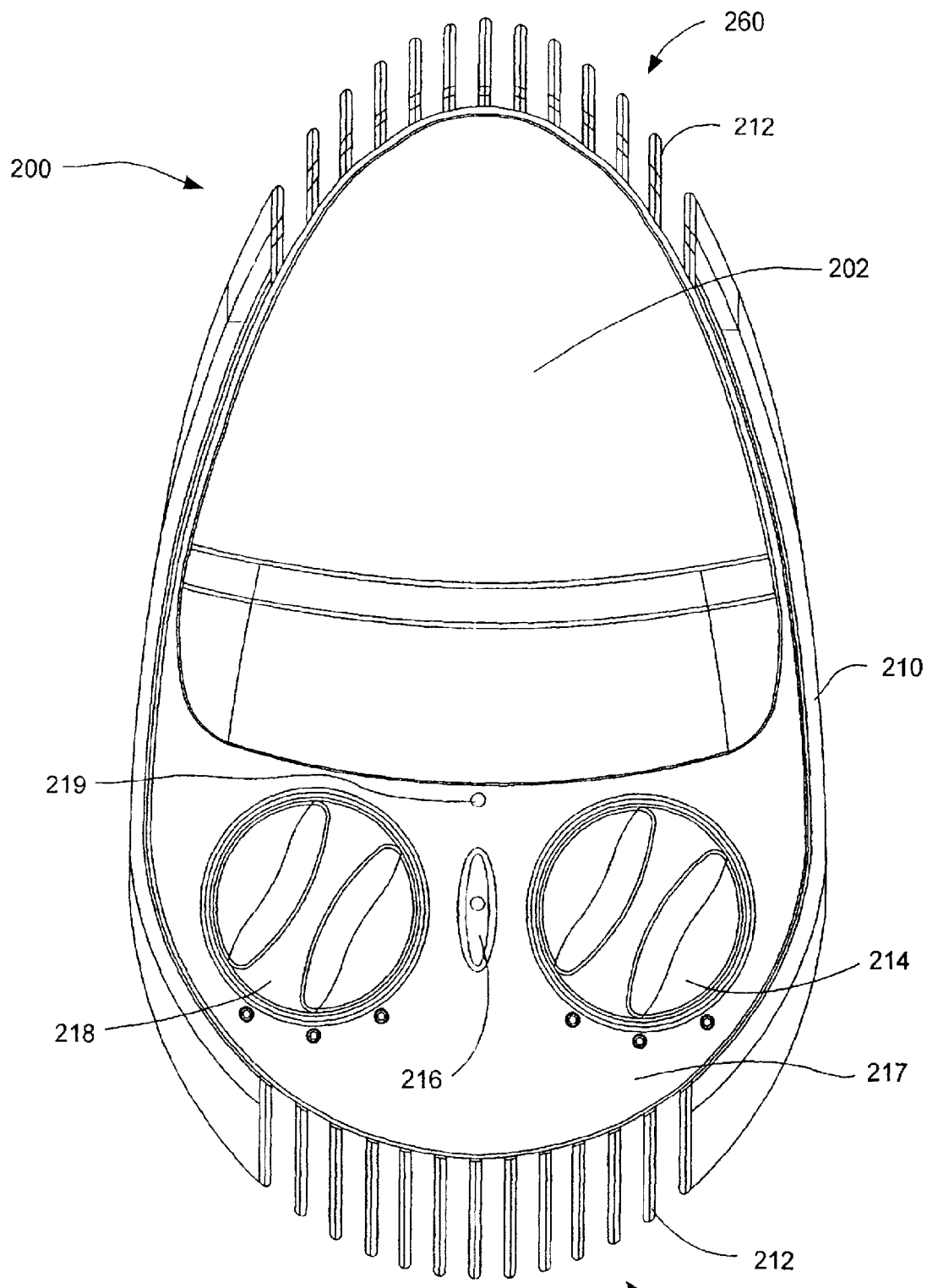

FIG. 3B illustrates the operating controls for the device 200. Located on top surface 217 of the housing 210 is an airflow speed control dial 214, a boost button 216, a function dial 218, and an overload/cleaning light 219. The airflow speed control dial 214 has three settings from which a user can choose: LOW, MED, and HIGH. The airflow rate is proportional to the voltage differential between the electrodes or electrode arrays coupled to the ion generator 160.

The LOW, MED, and HIGH settings generate a different predetermined voltage difference between the first and second arrays. For example, the LOW setting will create the smallest voltage difference, while the HIGH setting will create the largest voltage difference. Thus, the LOW setting will cause the device 200 to generate the slowest airflow rate, while the HIGH setting will cause the device 200 to generate the fastest airflow rate. These airflow rates are created by the electronic circuit disclosed in FIGS. 7A–7B, and operate as disclosed below.

The function dial 218 enables a user to select "ON," "ON/GP," or "OFF." The unit 200 functions as an electrostatic air transporter-conditioner, creating an airflow from the inlet 250 to the outlet 260, and removing the particles within the airflow when the function dial 218 is set to the "ON" setting. The germicidal lamp 290 does not operate, or emit UV light, when the function dial 218 is set to "ON." The device 200 also functions as an electrostatic air transporter conditioner, creating an airflow from the inlet 250 to the outlet 260, and removing particles within the airflow when the function dial 218 is set to the "ON/GP" setting. In addition, the "ON/GP" setting activates the germicidal lamp 290 to emit UV light to remove or kill bacteria within the airflow. The device 200 will not operate when the function dial 218 is set to the "OFF" setting.

As previously mentioned, the device 200 preferably generates small amounts of ozone to reduce odors within the room. If there is an extremely pungent odor within the room, or a user would like to temporarily accelerate the rate of cleaning, the device 200 has a boost button 216. When the boost button 216 is depressed, the device 200 will temporarily increase the airflow rate to a predetermined maximum rate, and generate an increased amount of ozone. The increased amount of ozone will reduce the odor in the room faster than if the device 200 was set to HIGH. The maximum airflow rate will also increase the particle capture rate of the device 200. In a preferred embodiment, pressing the boost button 216 will increase the airflow rate and ozone production continuously for 5 minutes. This time period maybe longer or shorter. At the end of the preset time period (e.g., 5 minutes), the device 200 will return to the airflow rate previously selected by the control dial 214.

The overload/cleaning light 219 indicates if the second electrodes 242 require cleaning, or if arcing occurs between the first and second electrode arrays. The overload/cleaning light 219 may illuminate either amber or red in color. The light 219 will turn amber if the device 200 has been operating continuously for more than two weeks and the second array 240 has not been removed for cleaning within the two week period. The amber light is controlled by the below described 2-week time circuit 130 (see FIG. 7B) which is connected to the power setting circuit 122. The device 200 will continue to operate after the light 219 turns amber. The light 219 is only an indicator. There are two ways to reset or turn the light 219 off. A user may remove and replace the second array 240 from the unit 200. The user may also turn the control dial 218 to the OFF position, and subsequently turn the control dial 218 back to the "ON" or "ON/GP" position. The timer circuit 130 will reset and begin counting a new two week period upon completing either of these two steps.

The light 219 will turn red to indicate that arcing has occurred between the first array 230 and the second array 240, as sensed by a sensing circuit 132, which is connected between the IGBT switch 126 and the connector oscillator 124 of FIG. 7B (as described below). When arcing occurs, the device 200 will automatically shut itself off. The device 200 cannot be restarted until the device 200 is reset. To reset the device 200, the second array 240 should first be removed from the housing 210 after the unit 200 is turned off. The second electrode 240 can then be cleaned and placed back into the housing 210. Then, the device 200 is turned on. If no arcing occurs, the device 200 will operate and generate an airflow. If the arcing between the electrodes continues, the device 200 will again shut itself off, and need to be reset.

Figure 3C:
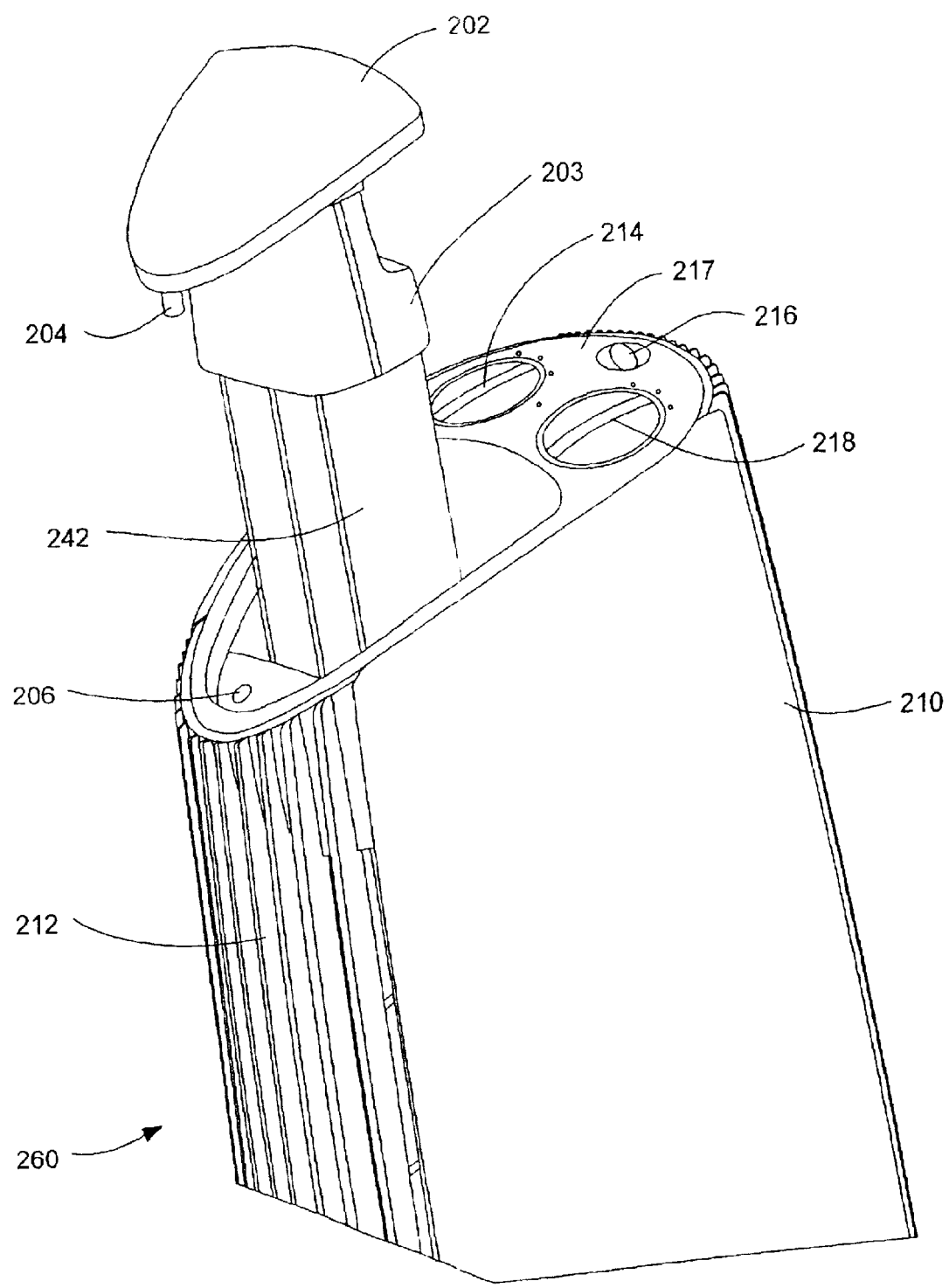

FIG. 3C illustrates the second electrodes 242 partially removed from the housing 210. In this embodiment, the handle 202 is attached to an electrode mounting bracket 203.

The bracket 203 secures the second electrodes 242 in a fixed, parallel configuration. Another similar bracket 203 is attached to the second electrodes 242 substantially at the bottom (not shown). The two brackets 203 align the second electrodes 242 parallel to each other, and in-line with the airflow traveling through the housing 210. Preferably, the brackets 203 are non-conductive surfaces.

One of the various safety features can be seen with the second electrodes 242 partially removed. As shown in FIG. 3C, an interlock post 204 extends from the bottom of the handle 202. When the second electrodes 242 are placed completely into the housing 210, the handle 202 rests within the top surface 217 of the housing, as shown by FIGS. 3A–3B. In this position, the interlock post 204 protrudes into the interlock recess 206 and activates a switch connecting the electrical circuit of the unit 200. When the handle 202 is removed from the housing 210, the interlock post 204 is pulled out of the interlock recess 206 and the switch opens the electrical circuit. With the switch in an open position, the unit 200 will not operate. Thus, if the second electrodes 242 are removed from the housing 210 while the unit 200 is operating, the unit 200 will shut off as soon as the interlock post 204 is removed from the interlock recess 206.

Figure 3D:
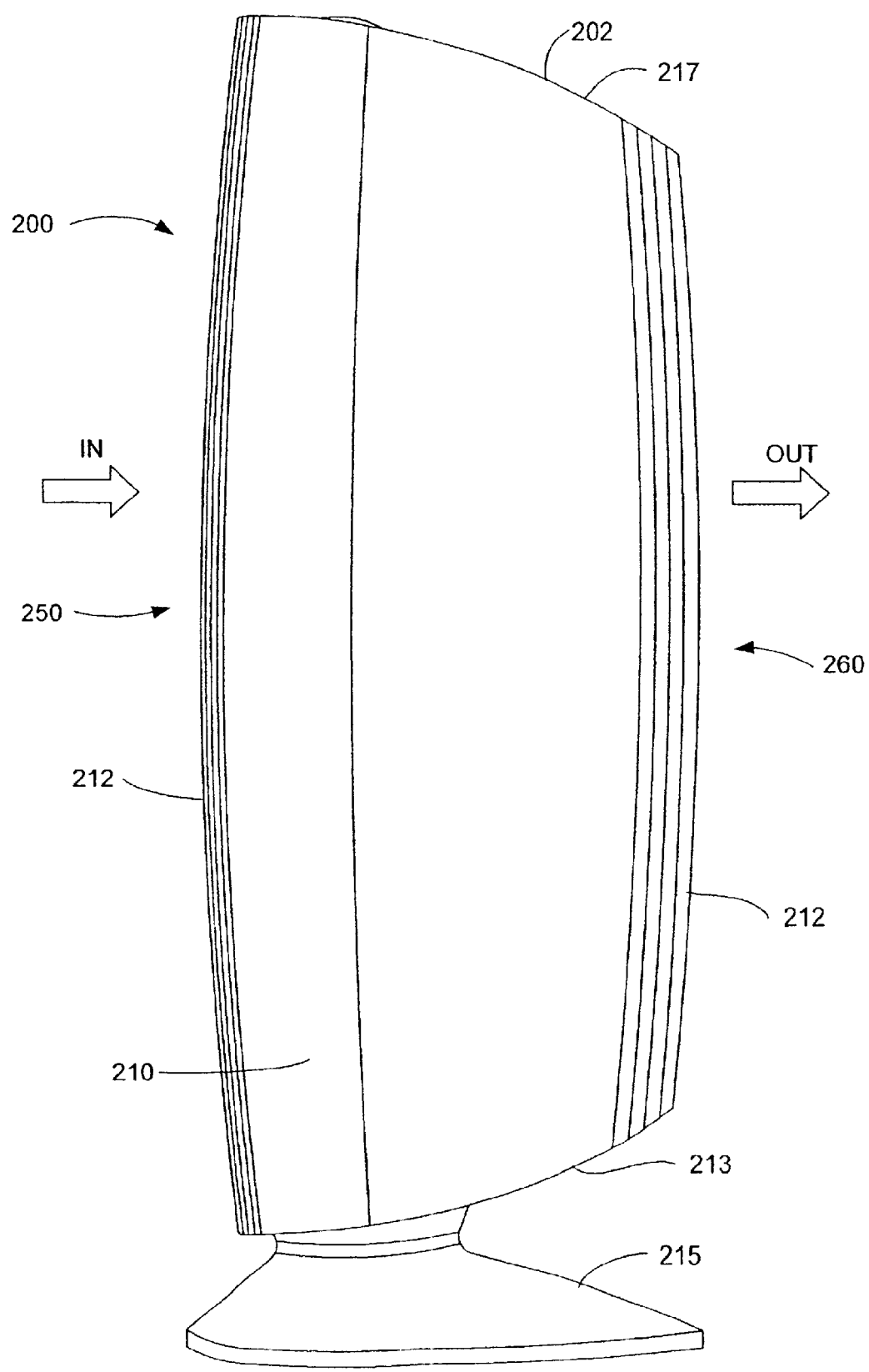

FIG. 3D depicts the housing 210 mounted on a stand or base 215. The housing 210 has an inlet 250 and an outlet 260. The base 215 sits on a floor surface. The base 215 allows the housing 210 to remain in a vertical position. It is within the scope of the present invention for the housing 210 to be pivotally connected to the base 215. As can be seen in FIG. 3D, housing 210 includes sloped top surface 217 and sloped bottom surface 213. These surfaces slope inwardly from inlet 250 to outlet 260 to additionally provide a streamline appearance and effect.

Figure 3E:
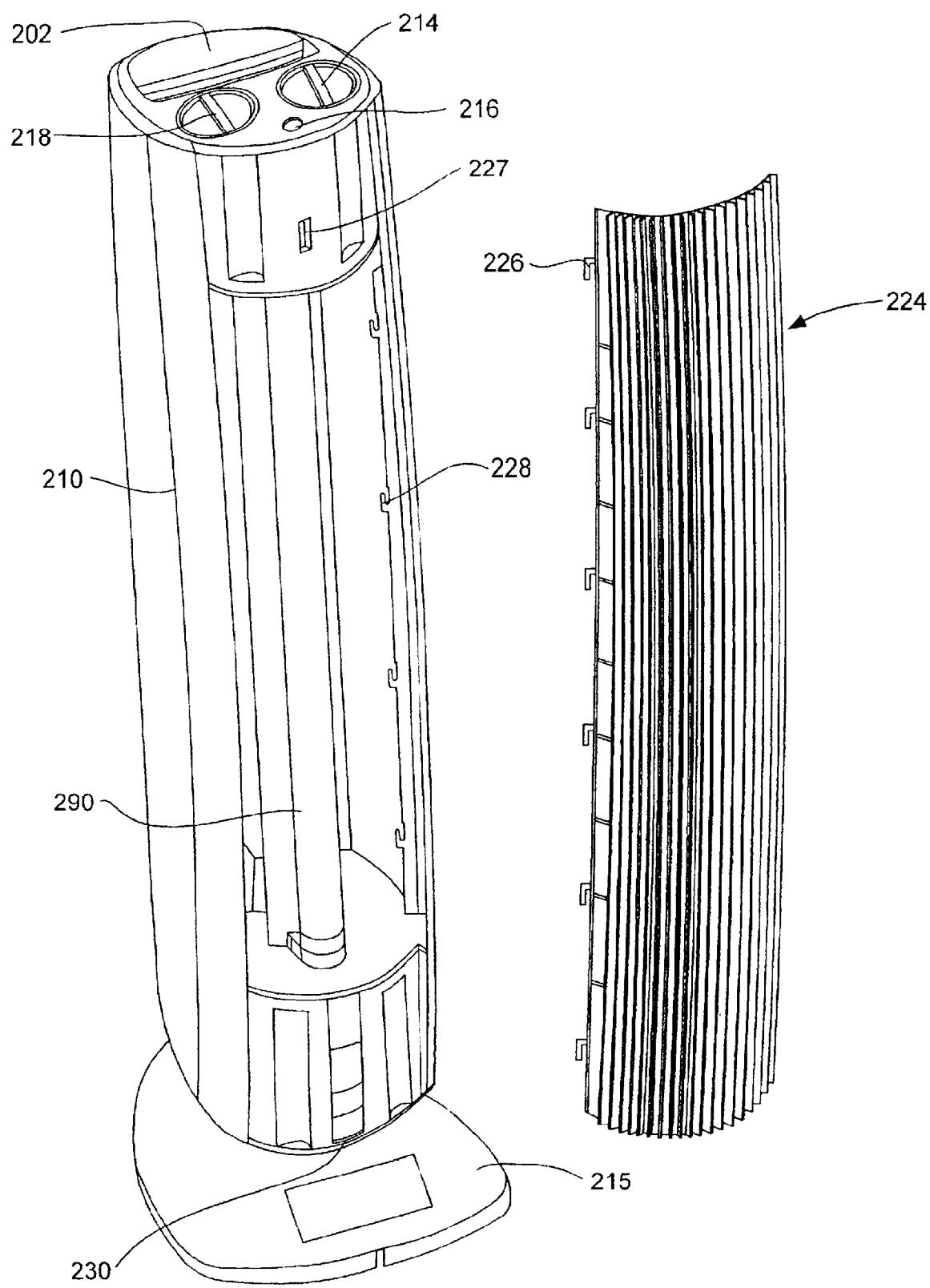

FIG. 3E illustrates that the housing 210 has are movable rear panel 224, allowing a user to easily access and remove the germicidal lamp 290 from the housing 210 when the lamp 290 expires. This rear panel 224 in this embodiment defines the air inlet and comprises the vertical louvers. The rear panel 224 has locking tabs 226 located on each side, along the entire length of the panel 224. The locking tabs 226, as shown in FIG. 3E, are "L"-shaped. Each tab 224 extends away from the panel 224, inward towards the housing 210, and then projects downward, parallel with the edge of the panel 224. It is within the spirit and scope of the invention to have differently shaped tabs 226. Each tab 224 individually and slidably interlocks with recesses 228 formed within the housing 210. The rear panel 224 also has a biased lever (not shown) located at the bottom of the panel 224 that interlocks with the recess 230. To remove the panel 224 from the housing 210, the lever is urged away from the housing 210, and the panel 224 is slid vertically upward until the tabs 226 disengage the recesses 228. The panel 224 is then pulled away from the housing 210. Removing the panel 224 exposes the lamp 290 for replacement.

The panel 224 also has a safety mechanism to shut the device 200 off when the panel 224 is removed. The panel 224 has a rear projecting tab (not shown) that engages the safety interlock recess 227 when the panel 224 is secured to the housing 210. Byway of example only, the rear tab depresses a safety switch located within the recess 227 when the rear panel 224 is secured to the housing 210. The device 200 will operate only when the rear tab in the panel 224 is fully inserted into the safety interlock recess 227. When the panel 224 is removed from the housing 210, the rear projecting tab is removed from the recess 227 and the power is cut-off to the entire device 200. For example if a user removes the rear panel 224 while the device 200 is running, and the germicidal lamp 290 is emitting UV radiation, the device 200 will turn off as soon as the rear projecting tab disengages from the recess 227. Preferably, the device 200 will turn off when the rear panel 224 is removed only a very short distance (e.g., ¼") from the housing 210. This safety switch operates very similar to the interlocking post 204, as shown in FIG. 3C.

FIG. 4

Figure 4:
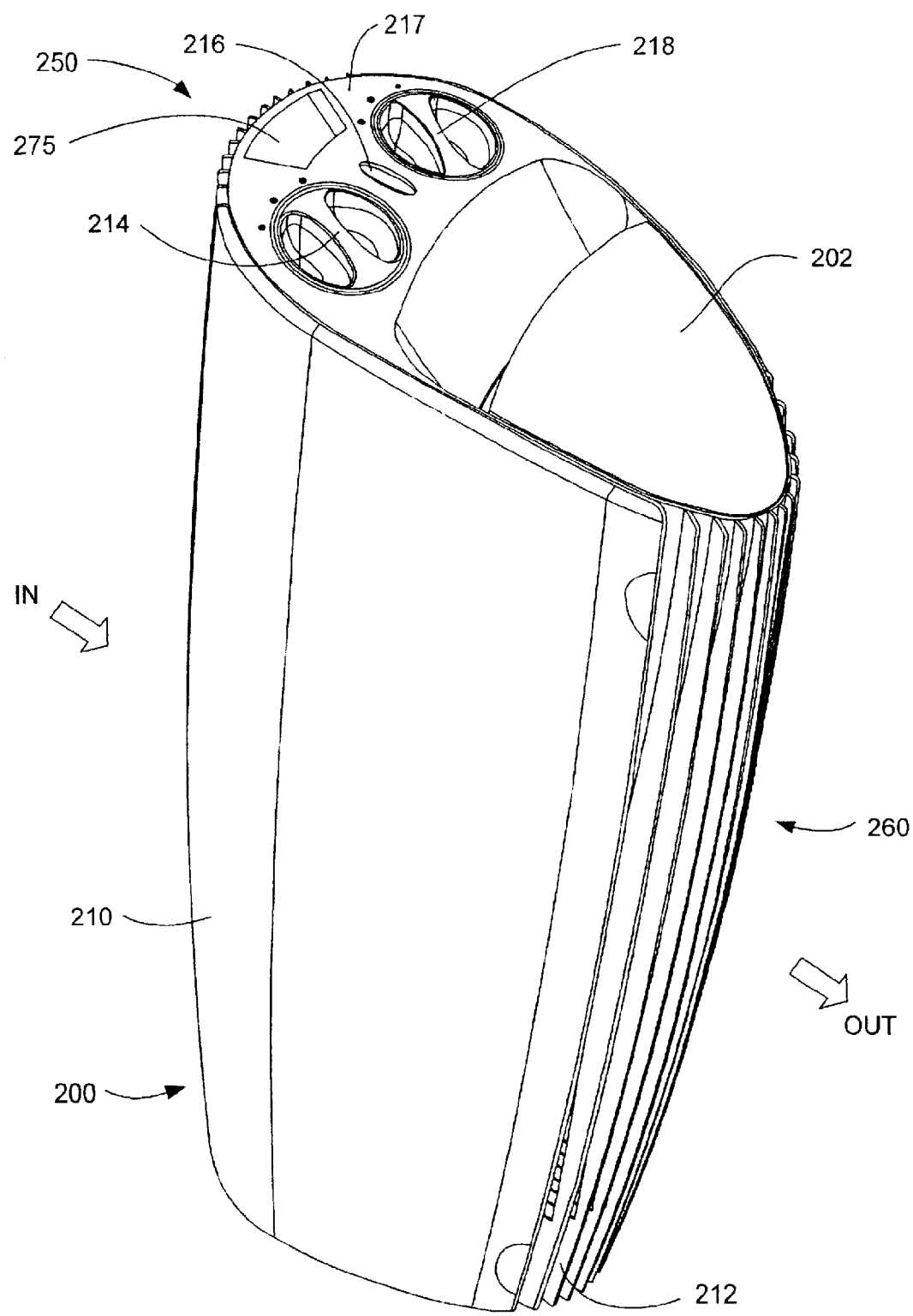
FIG. 4 is a perspective view of another embodiment of the present invention.

FIG. 4 illustrates yet another embodiment of the housing 210. In this embodiment, the germicidal lamp 290 maybe removed from the housing 210 by lifting the germicidal lamp 290 out of the housing 210 through the top surface 217. The housing 210 does not have are movable rear panel 224. Instead, a handle 275 is affixed to the germicidal lamp 290. The handle 275 is recessed within the top surface 217 of the housing 210 similar to the handle 202, when the lamp 290 is within the housing 210. To remove the lamp 290, the handle 275 is vertically raised out of the housing 210.

The lamp 290 is situated within the housing 210 in a similar manner as the second array of electrodes 240. That is to say, that when the lamp 290 is pulled vertically out of the top 217 of the housing 210, the electrical circuit that provides power to the lamp 290 is disconnected. 20 The lamp 290 is mounted in a lamp fixture that has circuit contacts which engages the circuit in FIG. 7A. As the lamp 290 and fixture are pulled out, the circuit contacts are disengaged. Further, as the handle 275 is lifted from the housing 210, a cutoff switch will shut the entire device 200 off. This safety mechanism ensures that the device 200 will not operate without the lamp 290 placed securely in the housing 210, preventing an individual from directly viewing the radiation emitted from the lamp 290. Reinserting the lamp 290 into the housing 210 causes the lamp fixture to reengage the circuit contacts as is known in the art. In similar, but less convenient fashion, the lamp 290 may be designed to be removed from the bottom of the housing 210.

The germicidal lamp 290 is a preferably UV-C lamp that preferably emits viewable light and radiation (in combination referred to as radiation or light 280) having wavelength of about 254 nm. This wavelength is effective in diminishing or destroying bacteria, germs, and viruses to which it is exposed. Lamps 290 are commercially available. For example, the lamp 290 maybe a Phillips model TUV 15W/G15T8, a 15 W tubular lamp measuring about 25 mm in diameter by about 43 cm in length. Another suitable lamp is the Phillips TUV 8WG8 T6, an 8 W lamp measuring about 15 mm in diameter by about 29 cm in length. Other lamps that emit the desired wavelength can instead be used.

FIGS. 5A–5B

Figure 5A:
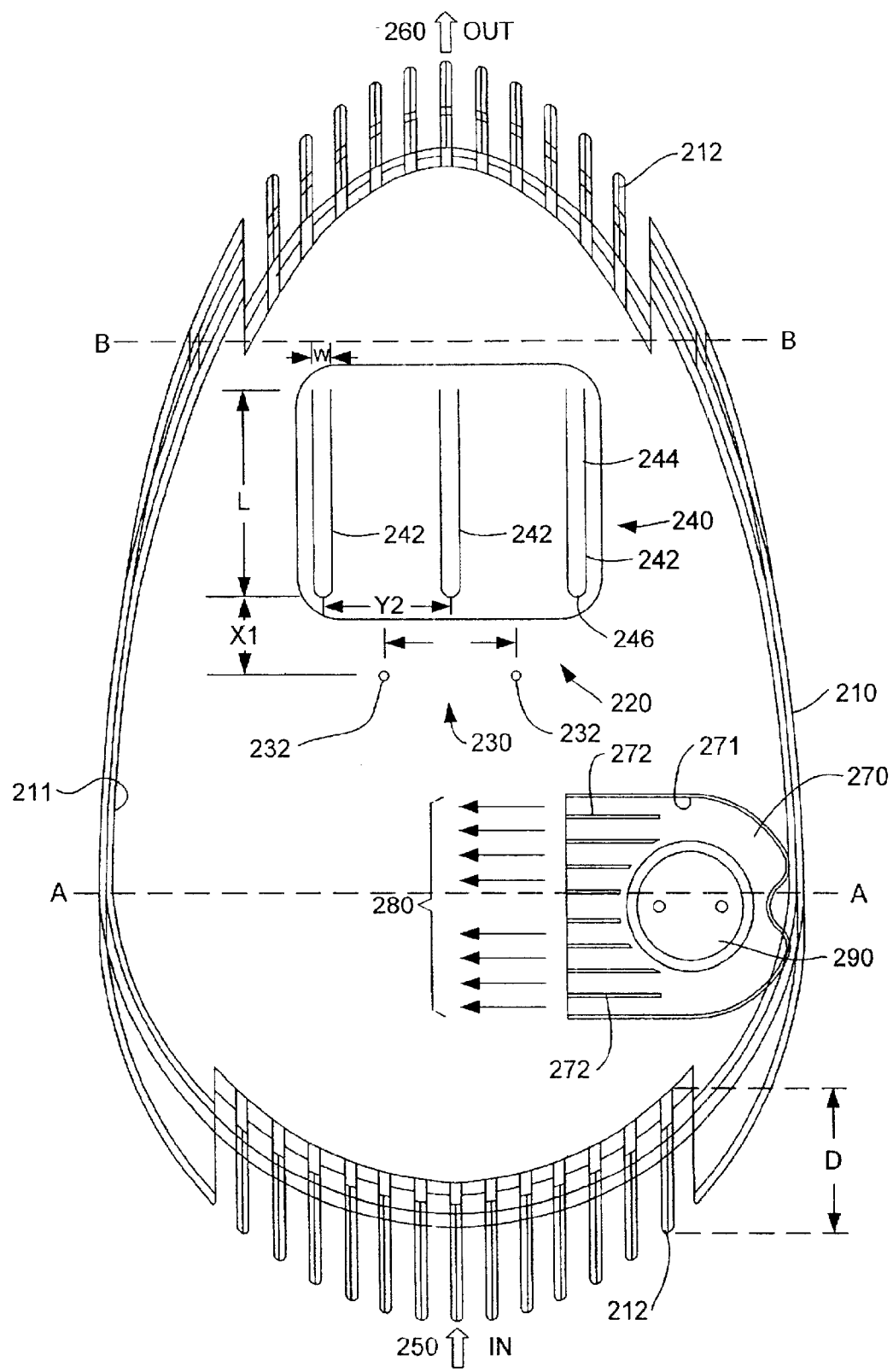
FIGS. 5A–5B.
Figure 5B:
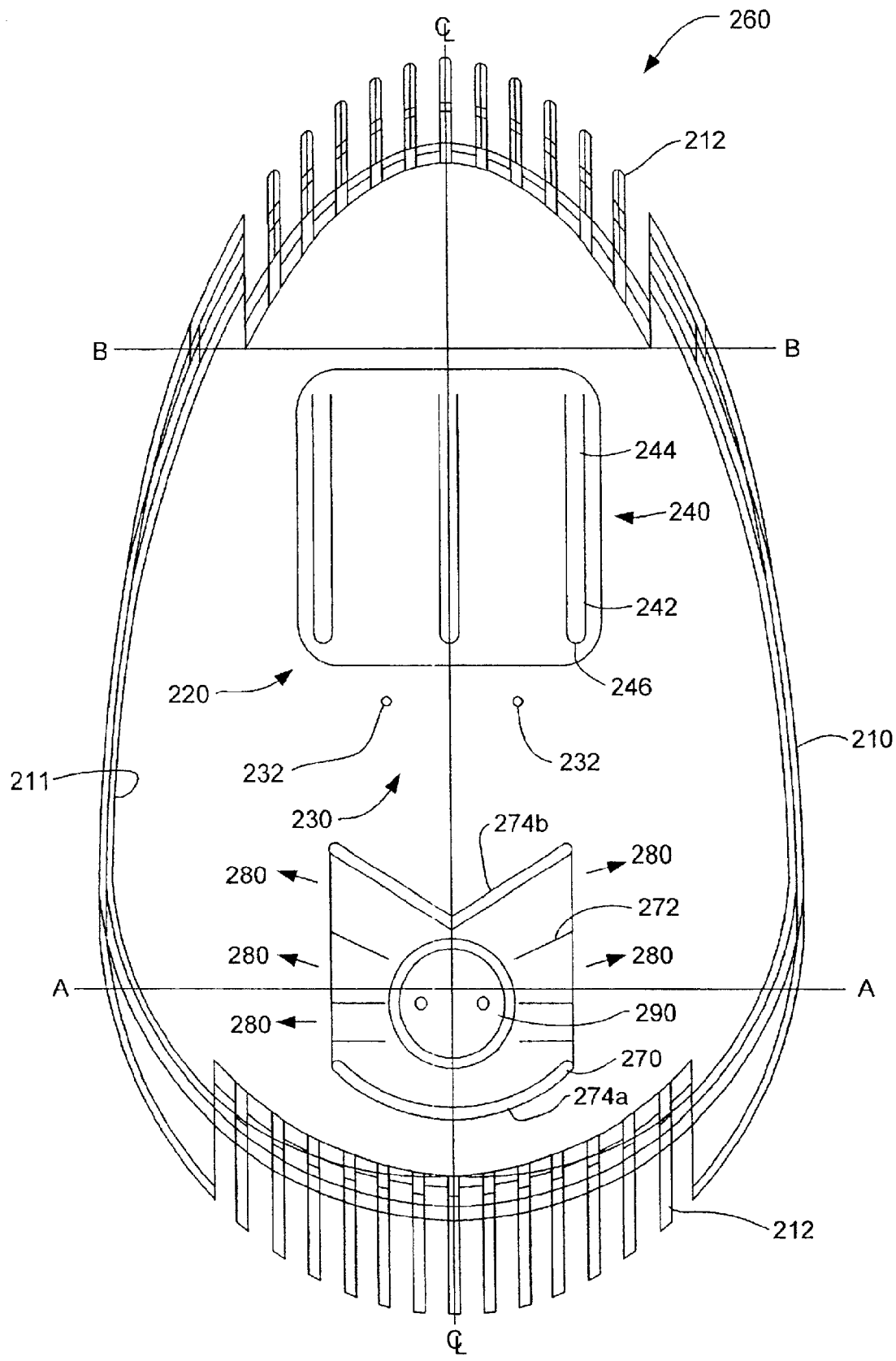

As previously mentioned, one role of the housing 210 is to prevent an individual from viewing, byway of example, ultraviolet (UV) radiation generated by a germicidal lamp 290 disposed within the housing 210. FIGS. 5A–5B illustrate preferred locations of the germicidal lamp 290 within the housing 210. FIGS. 5A–5B further show the spacial relationship between the germicidal lamp 290 and the electrode assembly 220, and the germicidal lamp 290 and the inlet 250 and the outlet 260 and the inlet and outlet louvers.

In a preferred embodiment, the inner surface 211 of the housing 210 diffuses or absorbs the UV light emitted from the lamp 290. FIGS. 5A–5B illustrate that the lamp 290 does emit some light 280 directly onto the inner surface 211 of the housing 210. By way of example only, the inner surface 211 of the housing 210 can be formed with anon-smooth finish, or a non-light reflecting finish or color, to also prevent the UV-C radiation from exiting through either the inlet 250 or the outlet 260. The UV portion of the radiation 280 striking the wall 211 will be absorbed and disbursed as indicated above.

As discussed above, the fins 212 covering the inlet 250 and the outlet 260 also limit any line of sight of the user into the housing 210. The fins 212 are vertically oriented within the inlet 250 and the outlet 260. The depth D of each fin 212 is preferably deep enough to prevent an individual from directly viewing the interior wall 211. In a preferred embodiment, an individual cannot directly view the inner surface 211 by moving from side-to-side, while looking into the outlet 260 or the inlet 250. Looking between the fins 212 and into the housing 210 allows an individual to "see through" the device 200. That is, a user can look into the inlet vent 250 or the outlet vent 260 and see out of the other vent. It is to be understood that it is acceptable to see light or a glow coming from within housing 210, if the light has a non-UV wavelength that is acceptable for viewing. In general, an user viewing into the inlet 250 or the outlet 260 maybe able to notice a light or glow emitted from within the housing 210. This light is acceptable to view. In general, when the radiation 280 strikes the interior surface 211 of the housing 210, the radiation 280 is shifted from its UV spectrum. The wavelength of the radiation changes from the UV spectrum into an appropriate viewable spectrum. Thus, any light emitted from within the housing 210 is appropriate to view.

As also discussed above, the housing 210 is designed to optimize the reduction of microorganisms within the airflow. The efficacy of radiation 280 upon microorganisms depends upon the length of time such organisms are subjected to the radiation 280. Thus, the lamp 290 is preferably located within the housing 210 where the airflow is the slowest. In preferred embodiments, the lamp 290 is disposed within the housing 210 along line A—A (see FIGS. 5A–7). Line A—A designates the largest width and cross-sectional area of the housing 210, perpendicular to the airflow. The housing 210 creates a fixed volume for the air to pass through. In operation, air enters the inlet 250, which has a smaller width, and cross-sectional area, than along line A—A. Since the width and cross-sectional area of the housing 210 along line A—A are larger than the width and cross-sectional area of the inlet 250, the airflow will decelerate from the inlet 250 to the line A—A. By placing the lamp 290 substantially along line A—A, the air will have the longest dwell time as it passes through the radiation 280 emitted by the lamp 290. In other words, the microorganisms within the air will be subjected to the radiation 280 for the longest period possible by placing the lamp 290 along line A—A. It is, however, within the scope of the present invention to locate the lamp 290 anywhere within the housing 210, preferably upstream of the electrode assembly 220.

A shell or housing 270 substantially surrounds the lamp 290. The shell 270 prevents the light 280 from shining directly towards the inlet 250 or the outlet 260. In a preferred embodiment, the interior surface of the shell 270 that faces the lamp 290 is a non-reflective surface. By way of example only, the interior surface of the shell 270 maybe a rough surface, or painted a dark, non-gloss color such as black. The lamp 290, as shown in FIGS. 5A–5B, is a circular tube parallel to the housing 210. In a preferred embodiment, the lamp 290 is substantially the same length as, or shorter than, the fins 212 covering the inlet 250 and outlet 260. The lamp 290 emits the light 280 outward in a 360° pattern. The shell 270 blocks the portion of the light 280 emitted directly towards the inlet 250 and the outlet 260. As shown in FIGS. 5A and 5B, there is no direct line of sight through the inlet 250 or the outlet 260 that would allow a person to view the lamp 290. Alternatively, the shell 270 can have an internal reflective surface in order to reflect radiation into the air stream.

In the embodiment shown in FIG. 5A, the lamp 290 is located along the side of the housing 210 and near the inlet 250. After the air passes through the inlet 250, the air is immediately exposed to the light 280 emitted by the lamp 290. An elongated "U"-shaped shell 270 substantially encloses the lamp 290. The shell 270 has two mounts to support and electrically connect the lamp 290 to the power supply.

In a preferred embodiment, as shown in FIG. 5B, the shell 270 comprises two separate surfaces. The wall 274a is located between the lamp 290 and the inlet 250. The first wall 274a is preferably "U"-shaped, with the concave surface facing the lamp 290. The convex surface of the wall 274a is preferably a non-reflective surface. Alternatively, the convex surface of the wall 274a may reflect the light 280 outward toward the passing airflow. The wall 274a is integrally formed with the removable rear panel 224. When the rear panel 224 is removed from the housing 210, the wall 274a is also removed, exposing the germicidal lamp 290. The germicidal lamp 290 is easily accessible in order to, as an example, replace the lamp 290 when it expires.

The wall 274b, as shown in FIG. 5B, is "V"-shaped. The wall 274b is located between the lamp 290 and the electrode assembly 220 to prevent a user from directly looking through the outlet 260 and viewing the UV radiation emitted from the lamp 290. In a preferred embodiment, the wall 274b is also a non-reflective surface. Alternatively, the wall 274b maybe a reflective surface to reflect the light 280. It is within the scope of the present invention for the wall 274b to have other shapes such as, but not limited to, "U"-shaped or "C"-shaped.

The shell 270 may also have fins 272. The fins 272 are spaced apart and preferably substantially perpendicular to the passing airflow. In general, the fins 272 further prevent the light 280 from shining directly towards the inlet 250 and the outlet 260. The fins have a black or non-reflective surface. Alternatively, the fins 272 may have a reflective surface. Fins 272 with a reflective surface may shine more light 280 onto the passing airflow because the light 280 will be repeatedly reflected and not absorbed by a black surface. The shell 270 directs the radiation towards the fins 272, maximizing the light emitted from the lamp 290 for irradiating the passing airflow. The shell 270 and fins 272 direct the radiation 280 emitted from the lamp 290 in a substantially perpendicular orientation to the crossing airflow traveling through the housing 210. This prevents the radiation 280 from being emitted directly towards the inlet 250 or the outlet 260.

FIG. 6

Figure 6:
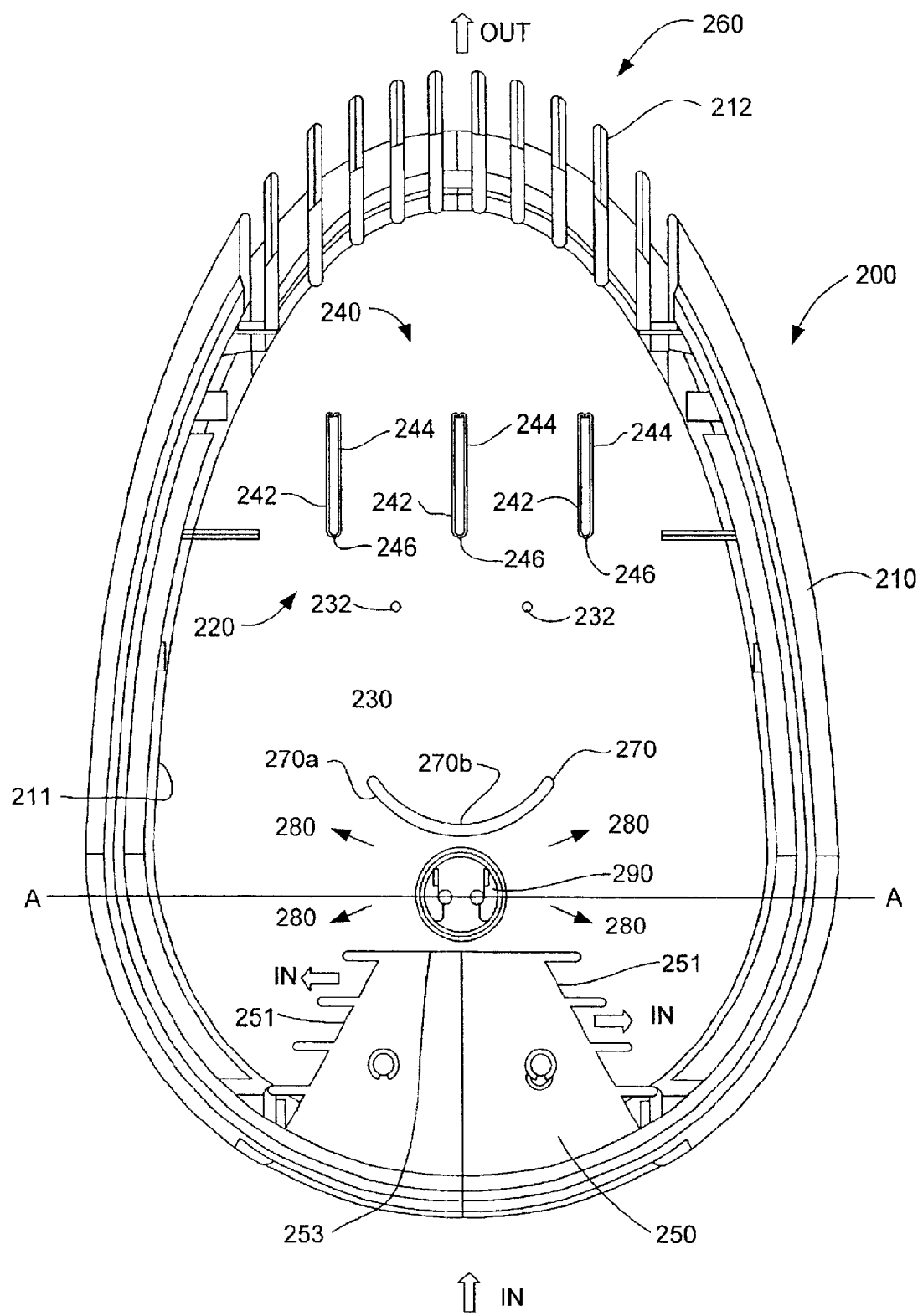
FIG. 6 is a top, partial cross-sectional view of yet another embodiment of the present invention.

FIG. 6 illustrates yet another embodiment of the device 200. The embodiment shown in FIG. 6 is a smaller, more portable, desk version of the air transporter-conditioner. Air is brought into the housing 210 through the inlet 250, as shown by the arrows marked "IN." The inlet 250 in this embodiment is an air chamber having multiple vertical slots 251 located along each side. In this embodiment, the slots are divided across the direction of the airflow into the housing 210. The slots 251 preferably are spaced apart a similar distance as the fins 212 in the previously described embodiments, and are substantially the same height as the side walls of the air chamber. In operation, air enters the housing 210 by entering the chamber 250 and then exiting the chamber 250 through the slots 251. The air contacts the interior wall 211 of the housing 210 and continues to travel through the housing 210 towards the outlet 260. Since the rear wall 253 of the chamber is a solid wall, the device 200 only requires a single non-reflective housing 270 located between the germicidal lamp 290 and the electrode assembly 220 and the outlet 260. The housing 270 in FIG. 6 is preferably "U"-shaped, with the convex surface 270a facing the germicidal lamp 290. The surface 270a directs the light 280 toward the interior surface 211 of the housing 210 and maximizes the disbursement of radiation into the passing airflow. It is within the scope of the invention for the surface 270 to comprise other shapes such as, but not limited to, a "V"-shaped surface, or to have the concave surface 270b face the lamp 290. Also in other embodiments the housing 270 can have a reflective surface in order to reflect radiation into the air stream. Similar to the previous embodiments, the air passes the lamp 290 and is irradiated by the light 280 soon after the air enters the housing 210, and prior to reaching the electrode assembly 220.

FIGS. 5A–6 illustrate embodiments of the electrode assembly 220. The electrode assembly 220 comprises a first emitter electrode array 230 and a second particle collector electrode array 240, which is preferably located downstream of the germicidal lamp 290. The specific configurations of the electrode array 220 are discussed below, and it is to be understood that any of the electrode assembly configurations depicted in FIGS. 8A–15C maybe used in the device depicted in FIGS. 2A–6. It is the electrode assembly 220 that creates ions and causes the air to flow electro-kinetically between the first emitter electrode array 230 and the second collector electrode array 240. In the embodiments shown in FIGS. 5A–6, the first array 230 comprises two wire-shaped electrodes 232, while the second array 240 comprises three "U"-shaped electrodes 242. Each "U"-shaped electrode has a nose 246 and two trailing sides 244. It is within the scope of the invention for the first array 230 and the second array 240 to include electrodes having other shapes as mentioned above and described below.

Figure 7A:
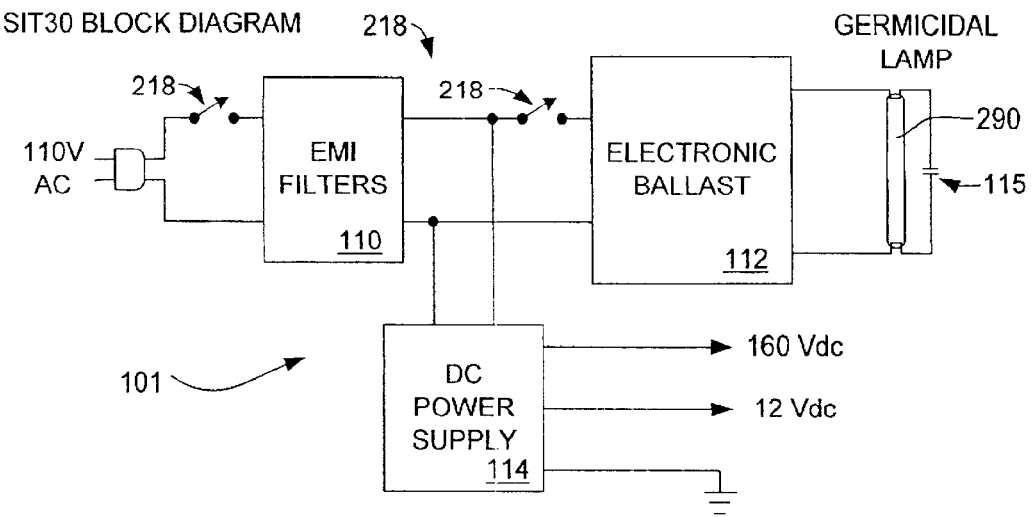
FIGS. 7A–7B.
Figure 7B:
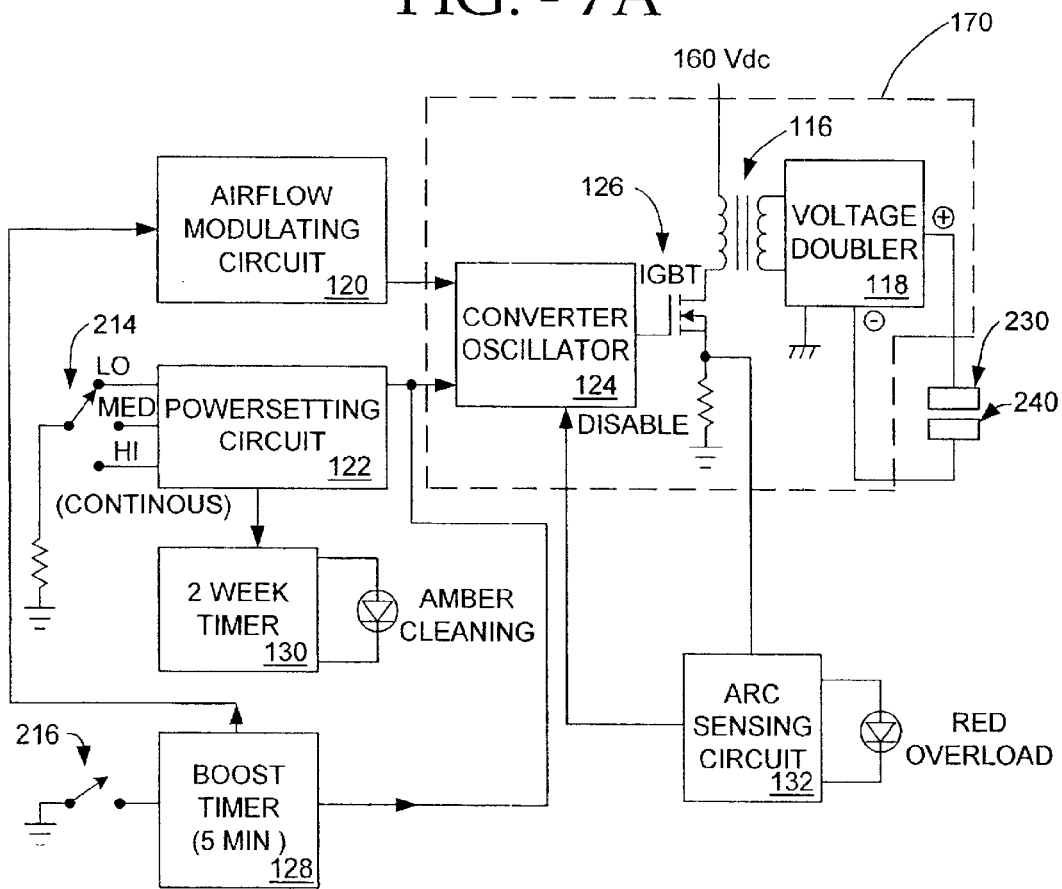

Electrical Circuit for the Electric-Kinetic Device:

FIGS. 7A–7B illustrate a preferred embodiment of an electrical block diagram for the electro-kinetic device 200 with enhanced anti-microorganism capability. FIG. 7A illustrates a preferred electrical block diagram of the germicidal lamp circuit 101. The main components of the circuit 101 are an electromagnetic interference (EMI) filter 110, an electronic ballast 112, and a DC power supply 114. The device 200 has an electrical power cord that plugs into a common electrical wall socket. The (EMI) filter 110 is placed across the incoming 110VAC line to reduce and/or eliminate high frequencies generated by the electronic ballast 112 and the high voltage generator 170. The electronic ballast 112 is electrically connected to the germicidal lamp 290 to regulate, or control, the flow of current through the lamp 290. Electrical components such as the EMI Filter 110 and electronic ballast 112 are well known in the art and do not require a further description. The DC Power Supply 114 receives the 110VAC and outputs 12VDC for the internal logic of the device 200, and 160VDC for the primary side of the transformer 116 (see FIG. 7B).

As seen in FIG. 7B, a high voltage pulse generator 170 is coupled between the first electrode array 230 and the second electrode array 240. The generator 170 receives low input voltage, e.g., 160VDC from DC power supply 114, and generates high voltage pulses of at least 5 KV peak-to-peak with a repetition rate of about 20 KHz. Preferably, the voltage doubler 118 outputs 9 KV to the first array 230, and 18 KV to the second array 240. It is within the scope of the present invention for the voltage doubler 118 to produce a greater or smaller voltage. The pulse train output preferably has a duty cycle of perhaps 10%, but may have other duty cycles, including a 100% duty cycle. The high voltage pulse generator 170 may be implemented in many ways, and typically will comprise a low voltage converter oscillator 124, operating at perhaps 20 KHz frequency, that outputs low voltage pulses to an electronic switch. Such a switch is shown as an insulated gate bipolar transistor (IGBT) 126. The IGBT 126, or other appropriate switch, couples the low voltage pulses from the oscillator 124 to the input winding of a step-up transformer 116. The secondary winding of the transformer 116 is coupled to the voltage doubler 118, which outputs the high voltage pulses to the first and second array of electrodes 230, 240. In general, the IGBT 126 operates as an electronic on/off switch. Such a transistor is well known in the art and does not require a further description.

The converter oscillator 124 receives electrical signals from the airflow modulating circuit 120, the power setting circuit 122, and the boost timer 128. The airflow rate of the device 200 is primarily controlled by the airflow modulating circuit 120 and the power setting circuit 122. The airflow modulating circuit 120 is a "micro-thing" gating circuit. The airflow modulating circuit 120 outputs an electrical signal that modulates between a "low" airflow signal and a "high" airflow signal. The airflow modulating circuit 120 continuously modulates between these two signals, preferably outputting the "high" airflow signal for 2.5 seconds, and then the "low" airflow signal for 5 seconds. By way of example only, the "high" airflow signal causes the voltage doubler 118 to provide 9 KV to the first array 230, while 18 KV is provided to the second array 240, and the "low" airflow signal causes the voltage doubler 118 to provide 6 KV to the first array 230, while 12 KV is provided to the second array 240. As will be described later, the voltage difference between the first and second array is proportional to the airflow rate of the device 200. In general, a greater voltage differential is created between the first and second array by the "high" airflow signal. It is within the scope of the present invention for the airflow modulating circuit 120 to produce different voltage differentials between the first and second arrays. The various circuits and components comprising the high voltage pulse generator 170 can be fabricated on a printed circuit board mounted within housing 210.

The power setting circuit 122 is a "macro-timing" circuit that can be set, by a control dial 214 (described hereinafter), to a LOW, MED, or HIGH setting. The three settings determine how long the signal generated by the airflow modulating circuit 120 will drive the oscillator 124. When the control dial 214 is set to HIGH, the electrical signal output from the airflow modulating circuit 120, modulating between the high and low airflow signals, will continuously drive the connector oscillator 124. When the control dial 214 is set to MED, the electrical signal output from the airflow modulating circuit 120 will cyclically drive the oscillator 124 for 25 seconds, and then drop to a zero or a lower voltage for 25 seconds. Thus, the airflow rate through the device 200 is slower when the dial 214 is set to MED than when the control dial 214 is set to HIGH. When the control dial 214 is set to LOW, the signal from the airflow modulating circuit 120 will cyclically drive the oscillator 124 for 25 seconds, and then drop to a zero or a lower voltage for 75 seconds. It is within the scope and spirit of the present invention for the HIGH, MED, and LOW settings to drive the oscillator 124 for longer or shorter periods of time.

The boost timer 128 sends an electrical signal to the airflow modulating circuit 120 and the powersetting circuit 122 when the boost button 216 is depressed. The boost timer 128 when activated, instructs the airflow modulating circuit 120 to continuously drive the converter oscillator 124 as if the device 200 was set to the HIGH setting. The boost timer 128 also sends a signal to the power setting circuit 122 that shuts the powersetting circuit 122 temporarily off. In effect, the boost timer 128 overrides the setting that the device 200 is set to by the dial 214. Therefore, the device 200 will run at a maximum airflow rate for a 5 minute period.

FIG. 7B further illustrates some preferred timing and maintenance features of the device 200. The device 200 has a 2 week timer 130 that provides a reminder to the user to clean the device 200, and an arc sensing circuit 132 that may shut the device 200 completely off in case of arcing.

Electrode Assembly with First and Second Electrodes: FIGS. 8A–8F

FIGS. 8A–8F illustrate various configurations of the electrode assembly 220. The output from high voltage pulse generator unit 170 is coupled to an electrode assembly 220 that comprises a first electrode array 230 and a second electrode array 240. Again, instead of arrays, a single electrode or single conductive surface can be substituted for one or both array 230 and array 240.

The positive output terminal of unit 170 is coupled to first electrode array 230, and the negative output terminal is coupled to second electrode array 240. It is believed that with this arrangement the net polarity of the emitted ions is positive, e.g., more positive ions than negative ions are emitted. This coupling polarity has been found to work well, including minimizing unwanted audible electrode vibration or hum. However, while generation of positive ions is conducive to a relatively silent airflow, from a health standpoint, it is desired that the output airflow be richer in negative ions, not positive ions. It is noted that in some embodiments, one port (preferably the negative port) of the high voltage pulse generator 170 need not be connected to the second array of electrodes 240. Nonetheless, there will be an "effective connection" between the second array electrodes 242 and one output port of the high voltage pulse generator 170, in this instance, via ambient air. Alternatively the negative output terminal of unit 170 can be connected to the first electrode array 230 and the positive output terminal can be connected to the second electrode array 240.

With this arrangement an electrostatic flow of air is created, going from the first electrode array 230 towards the second electrode array 240. (This flow is denoted "OUT" in the figures.) Accordingly electrode assembly 220 is mounted within transporter system 100 such that second electrode array 240 is closer to the OUT vents and first electrode array 230 is closer to the IN vents.

When voltage or pulses from high voltage pulse generator 170 are coupled across first and second electrode arrays 230 and 240, a plasma-like field is created surrounding electrodes 232 in first array 230. This electric field ionizes the ambient air between the first and second electrode arrays and establishes an "OUT" airflow that moves towards the second array 240. It is understood that the "IN" flow enters via vent(s) 104 or 250, and that the "OUT" flow exits via vent(s) 106 or 260.

Ozone and ions are generated simultaneously by the first array electrodes 232, essentially as a function of the potential from generator 170 coupled to the first array of electrodes or conductive surfaces. Ozone generation can be increased or decreased by increasing or decreasing the potential at the first array 230. Coupling an opposite polarity potential to the second array electrodes 242 essentially accelerates the motion of ions generated at the first array 230, producing the airflow denoted as "OUT" in the figures. As the ions and ionized particles move toward the second array 240, the ions and ionized particles push or move air molecules toward the second array 240. The relative velocity of this motion maybe increased, by way of example, by decreasing the potential at the second array 240 relative to the potential at the first array 230.

For example, if+10 KV were applied to the first array electrode(s) 232, and no potential were applied to the second array electrode(s) 242, a cloud of ions (whose net charge is positive) would form adjacent the first electrode array 230. Further, the relatively high 10 KV potential would generate substantial ozone. By coupling a relatively negative potential to the second array electrode(s) 242, the velocity of the air mass moved by the net emitted ions increases.

On the other hand, if it were desired to maintain the same effective outflow (OUT) velocity, but to generate less ozone, the exemplary 10 KV potential could be divided between the electrode arrays. For example, generator 170 could provide +4 KV (or some other fraction) to the first array electrodes 232 and −6 KV (or some other fraction) to the second array electrodes 242. In this example, it is understood that the +4 KV and the −6 KV are measured relative to ground. Understandably it is desired that the unit 100 operates to output appropriate amounts of ozone. Accordingly, the high voltage is preferably fractionalized with about +4 KV applied to the first array electrodes 232 and about −6 KV applied to the second array electrodes 242.

Figure 8A:
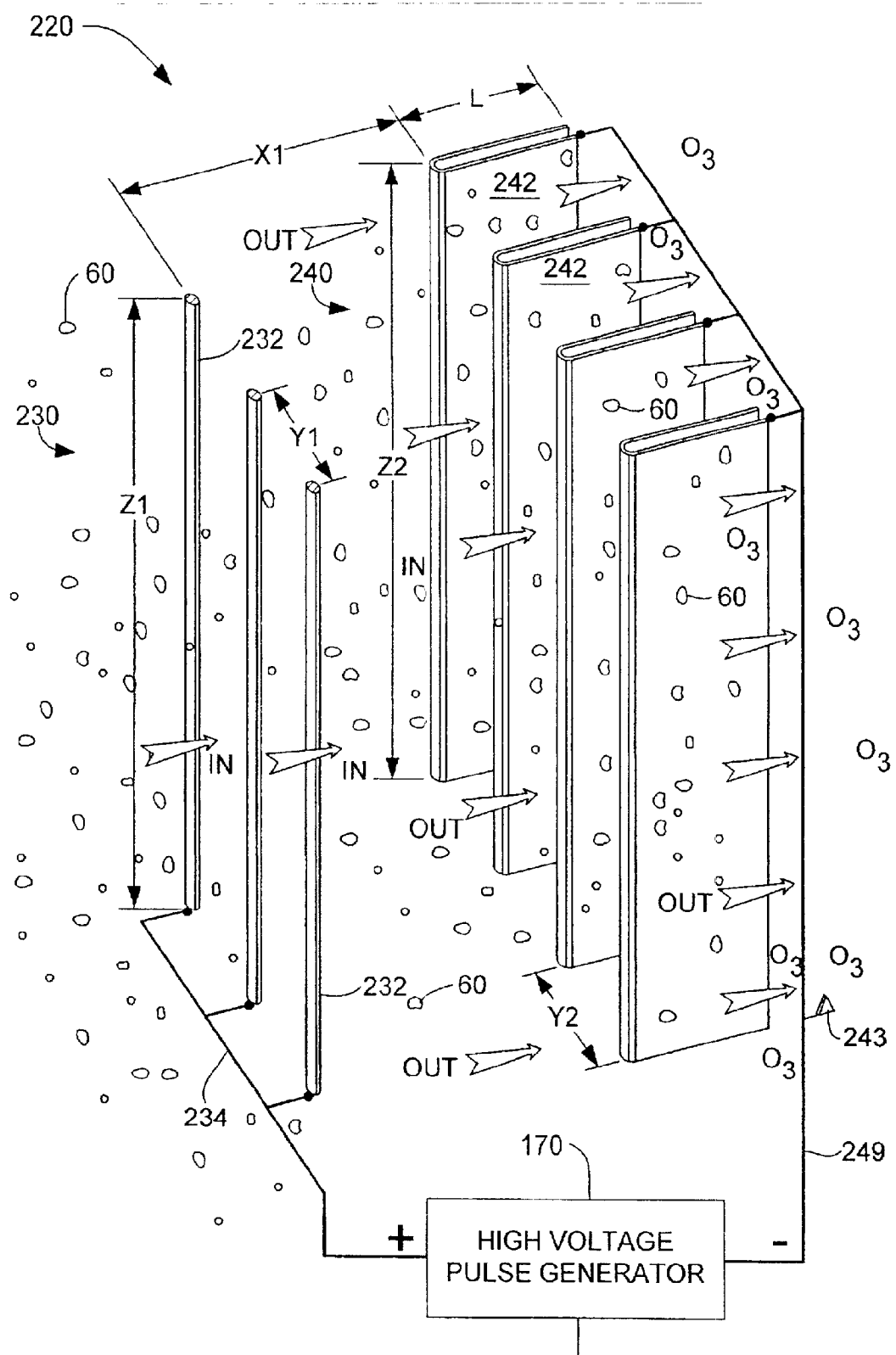
FIGS. 8A–8F.
Figure 8B:
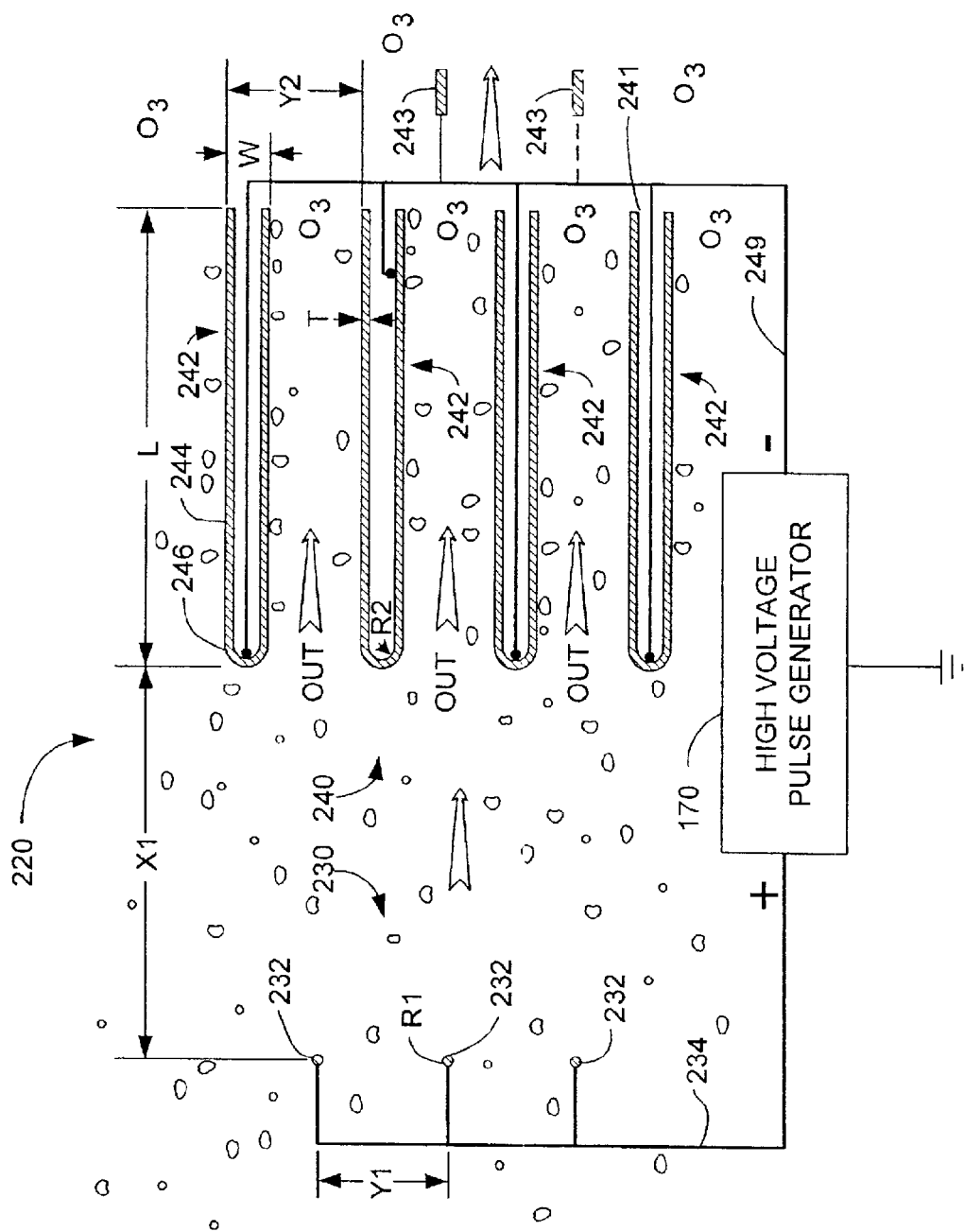

In the embodiments of FIGS. 8A and 8B, electrode assembly 220 comprises a first array 230 of wire-shaped electrodes 232, and a second array 240 of generally "U"-shaped electrodes 242. In preferred embodiments, the number N1 of electrodes comprising the first array 230 can preferably differ by one relative to the number N2 of electrodes comprising the second array 240. In many of the embodiments shown, N2>N1. However, if desired, additional first electrodes 232 could be added at the outer ends of array 230 such that N1>N2, e.g., five first electrodes 232 compared to four second electrodes 242.

As previously indicated, first or emitter electrodes 232 are preferably lengths of tungsten wire, whereas electrodes 242 are formed from sheet metal, preferably stainless steel, although brass or other sheet metal could be used. The sheet metal is readily configured to define side regions 244 and a bulbous nose region 246, forming the hollow, elongated "U"-shaped electrodes 242. While FIG. 8A depicts four electrodes 242 in second array 240 and three electrodes 232 in first array 230, as noted previously, other numbers of electrodes in each array could be used, preferably retaining a symmetrically staggered configuration as shown. It is seen in FIG. 8A that while particulate matter 60 is present in the incoming (IN) air, the outflow (OUT) air is substantially devoid of particulate matter, which adheres to the preferably large surface area provided by the side regions 244 of the second array electrodes 242.

FIG. 8B illustrates that the spaced-apart configuration between the first and second arrays 230, 240 is staggered. Preferably, each first array electrode 232 is substantially equidistant from two second array electrodes 242. This symmetrical staggering has been found to be an efficient electrode placement. Preferably, in this embodiment, the staggering geometry is symmetrical in that adjacent electrodes 232 or adjacent electrodes 242 are spaced-apart a constant distance, Y1 and Y2 respectively. However, a non-symmetrical configuration could also be used. Also, it is understood that the number of electrodes 232 and 242 may differ from what is shown.

In the embodiment of FIGS. 8A, typically dimensions are as follows: diameter of electrodes 232, R1, is about 0.08 mm, distances Y1 and Y2 are each about 16 mm, distance X1 is about 16 mm, distance L is about 20 mm, and electrode heights Z1 and Z2 are each about 1 m. The width W of electrodes 242 is preferably about 4 mm, and the thickness of the material from which electrodes 242 are formed is about 0.5 mm. Of course, other dimensions and shapes could be used. For example, preferred dimensions for distance X1 may vary between 12–30 mm, and the distance Y2 may vary between 15–30 mm. It is preferred that electrodes 232 have a small diameter, such as R1 shown in FIG. 8B. The small diameter electrode generates a high voltage field and has a high emissivity. Both characteristics are beneficial for generating ions. At the same time, it is desired that electrodes 232 (as well as electrodes 242) be sufficiently robust to withstand occasional cleaning.

Electrodes 232 in first array 230 are electrically connected to a first (preferably positive) output port of high voltage pulse generator 170 by a conductor 234. Electrodes 242 in second array 240 are electrically connected to a second (preferably negative) output port of high voltage generator 170 by a conductor 249. The first and second electrodes maybe electrically connected to the high voltage generator 170 at various locations. By way of example only, FIG. 8B depicts conductor 249 making connection with some electrodes 242 internal to nose 246, while other electrodes 242 make electrical connection to conductor 249 elsewhere on the electrode 242. Electrical connection to the various electrodes 242 could also be made on the electrode external surface, provided no substantial impairment of the outflow airstream results; however it has been found to be preferable that the connection is made internally.

In this and the other embodiments to be described herein, ionization appears to occur at the electrodes 232 in the first electrode array 230, with ozone production occurring as a function of high voltage arcing. For example, increasing the peak-to-peak voltage amplitude and/or duty cycle of the pulses from the high voltage pulse generator 170 can increase ozone content in the output flow of ionized air. If desired, user-control S2 or the dial 214 can be used to somewhat vary ozone content by varying amplitude and/or duty cycle. Specific circuitry for achieving such control is known in the art and need not be described in detail herein.

Note the inclusion in FIGS. 8A and 8B of at least one output controlling electrodes 243, preferably electrically coupled to the same potential as the second array electrodes 242. Electrode 243 preferably defines a pointed shape in side profile, e.g., a triangle. The sharp point on electrodes 243 causes generation of substantial negative ions (since the electrode is coupled to relatively negative high potential). These negative ions neutralize excess positive ions otherwise present in the output airflow, such that the "OUT" flow has a net negative charge. Electrode 243 is preferably manufactured from stainless steel, copper, or other conductor material, and is perhaps 20 mm high and about 12 mm wide at the base. The inclusion of one electrode 243 has been found sufficient to provide a sufficient number of output negative ions, but more such electrodes maybe included.

Figure 8C:
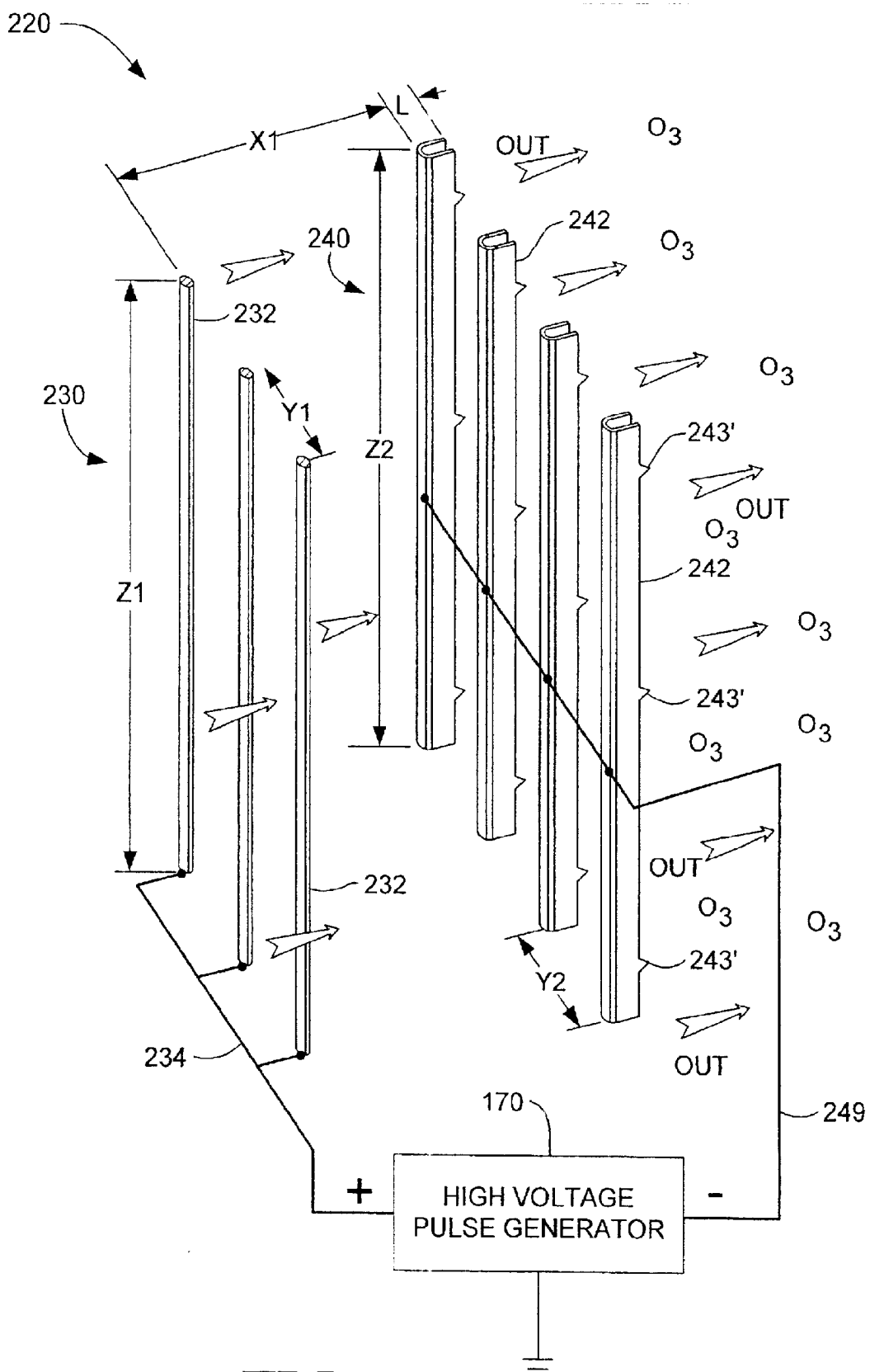

In the embodiments of FIGS. 8A, 8B and 8C, each "U"-shaped electrode 242 has two trailing surface or sides 244 that promote efficient kinetic transport of the outflow of ionized air and ozone. For the embodiment of FIG. 8C, there is the inclusion on at least one portion of a trailing edge of a pointed electrode region 243'. Electrode region 243' helps promote output of negative ions, in the same fashion that was previously described with respect to electrodes 243, as shown in FIGS. 8A and 8B.

In FIG. 8C and the figures to follow, the particulate matter is omitted for ease of illustration. However, from what was shown in FIGS. 8A–8B, particulate matter will be present in the incoming air, and will be substantially absent from the outgoing air. As has been described, particulate matter 60 typically will be electrostatically precipitated upon the surface area of electrodes 242.

As discussed above and as depicted by FIG. 8C, it is relatively unimportant where on an electrode array the electrical connection is made with the high voltage generator 170. In this embodiment, first array electrodes 232 are shown electrically connected together at their bottom regions by conductor 234, whereas second array electrodes 242 are shown electrically connected together in their middle regions by the conductor 249. Both arrays maybe connected together in more than one region, e.g., at the top and at the bottom. It is preferred that the wire or strips or other inter-connecting mechanisms be at the top, bottom, or periphery of the second array electrodes 242, so as to minimize obstructing stream air movement through the housing 210.

Figure 8D:
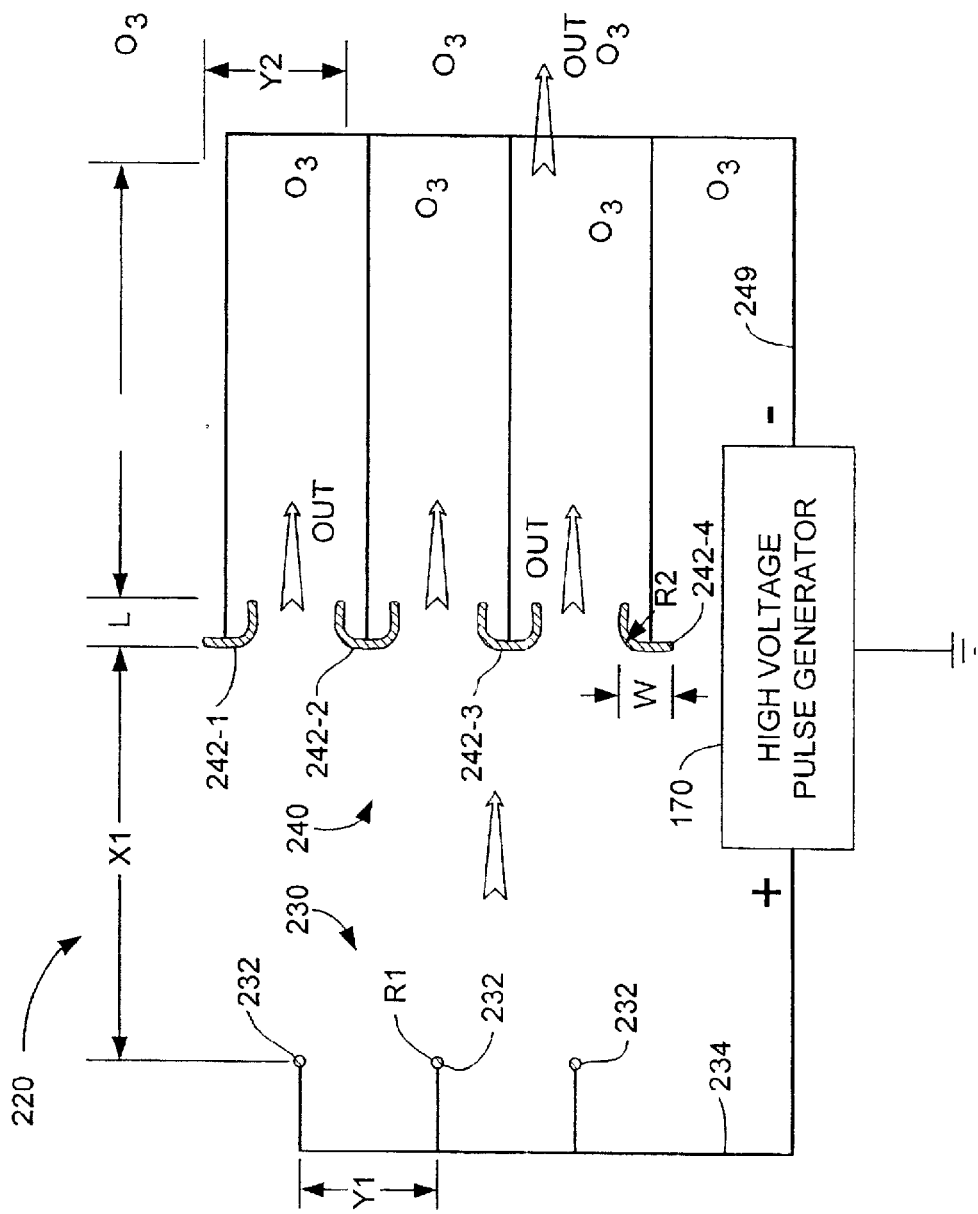

It is noted that the embodiments of FIGS. 8C and 8D depict somewhat truncated versions of the second electrodes 242. Whereas dimension L in the embodiment of FIGS. 8A and 8B was about 20 mm, in FIGS. 8C and 8D, L has been shortened to about 8 mm. Other dimensions in FIG. 8C preferably are similar to those stated for FIGS. 8A and 8B. It will be appreciated that the configuration of second electrode array 240 in FIG. 8C can be more robust than the configuration of FIGS. 8A and 8B, by virtue of the shorter trailing edge geometry. As noted earlier, a symmetrical staggered geometry for the first and second electrode arrays is preferred for the configuration of FIG. 8C.

In the embodiment of FIG. 8D, the outermost second electrodes, denoted 242-1 and 242-4, have substantially no outermost trailing edges. Dimension L in FIG. 8D is preferably about 3 mm, and other dimensions maybe as stated for the configuration of FIGS. 8A and 8B. Again, the ratio of the radius or surface areas between the first electrode 232 and the second electrodes 242 for the embodiment of FIG. 8D preferably exceeds about 20:1.

Figure 8E:
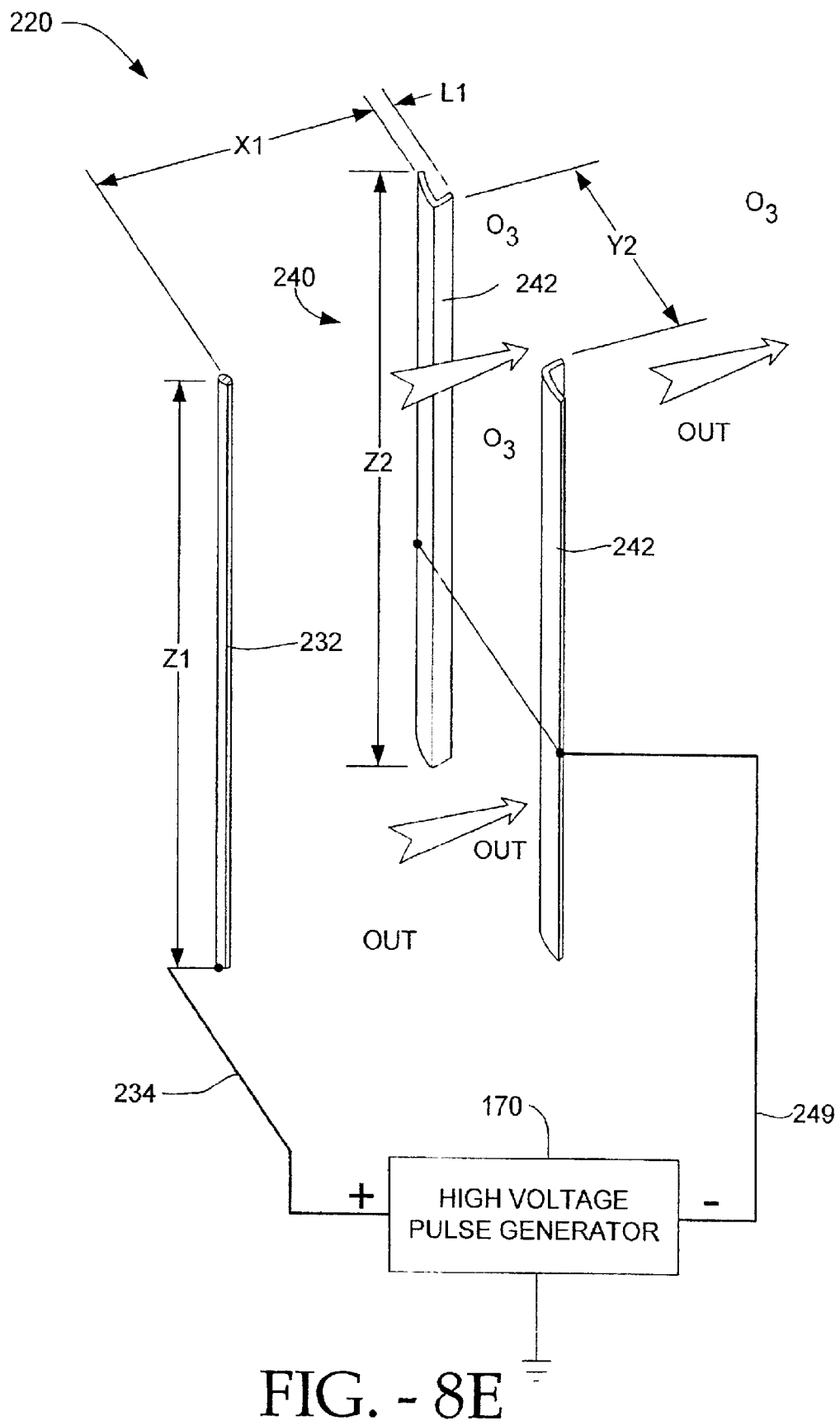
Figure 8F:
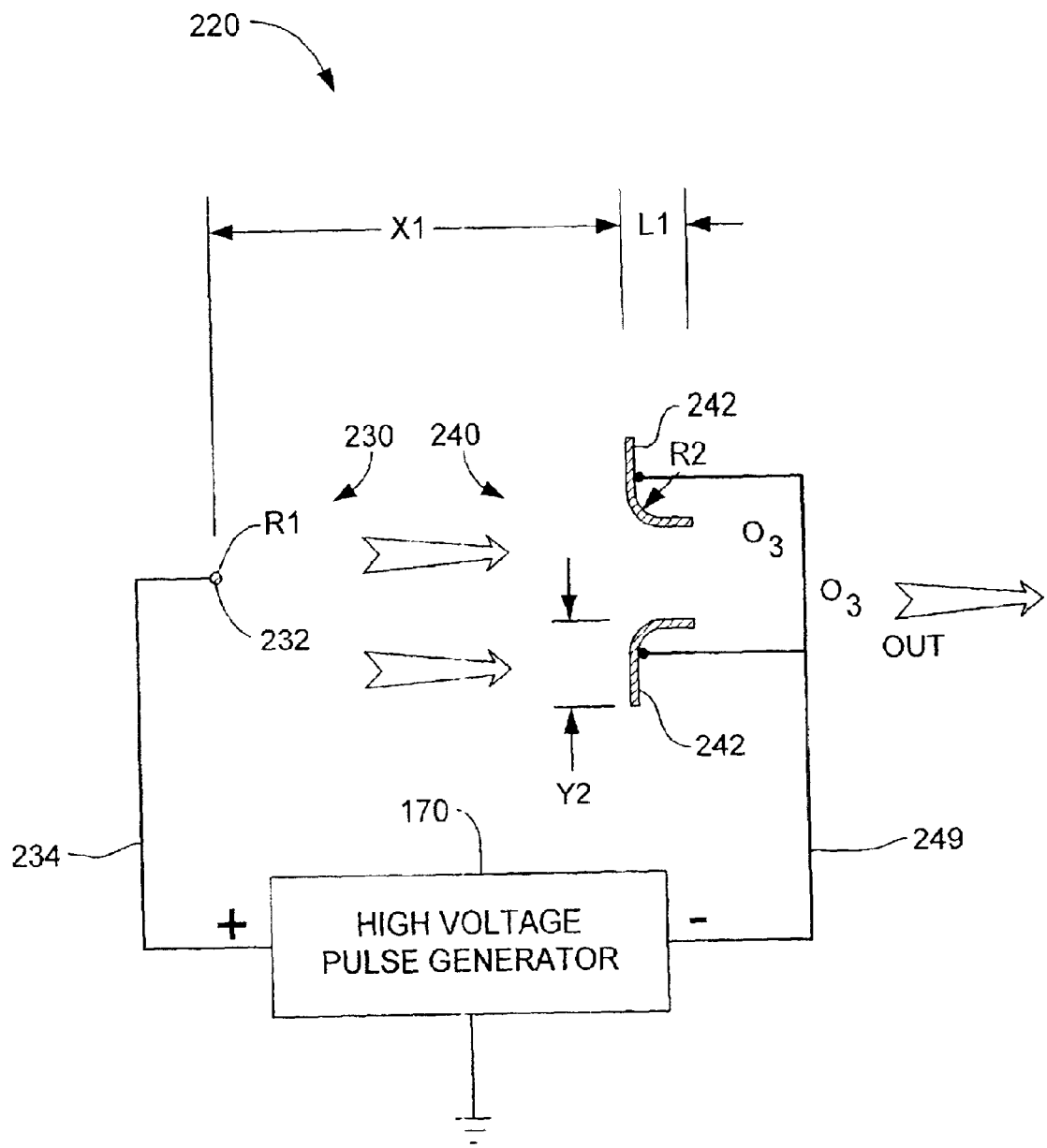

FIGS. 8E and 8F depict another embodiment of electrode assembly 220, in which the first electrode array 230 comprises a single wire electrode 232, and the second electrode array 240 comprises a single pair of curved "L"-shaped electrodes 242, in cross-section. Typical dimensions, where different than what has been stated for earlier-described embodiments, are X1≈12 mm, Y2≈5 mm, and L1≈3 mm. The effective surface area or radius ratio between the electrode arrays is again greater than about 20:1. The fewer electrodes comprising assembly 220 in FIGS. 8E and 8F promote economy of construction, and ease of cleaning, although more than one electrode 232, and more than two electrodes 242 could of course be employed. This particular embodiment incorporates the staggered symmetry described earlier, in which electrode 232 is equidistant from two electrodes 242. Other geometric arrangements, which may not be equidistant, are within the spirit and scope of the invention.

Figure 9A:
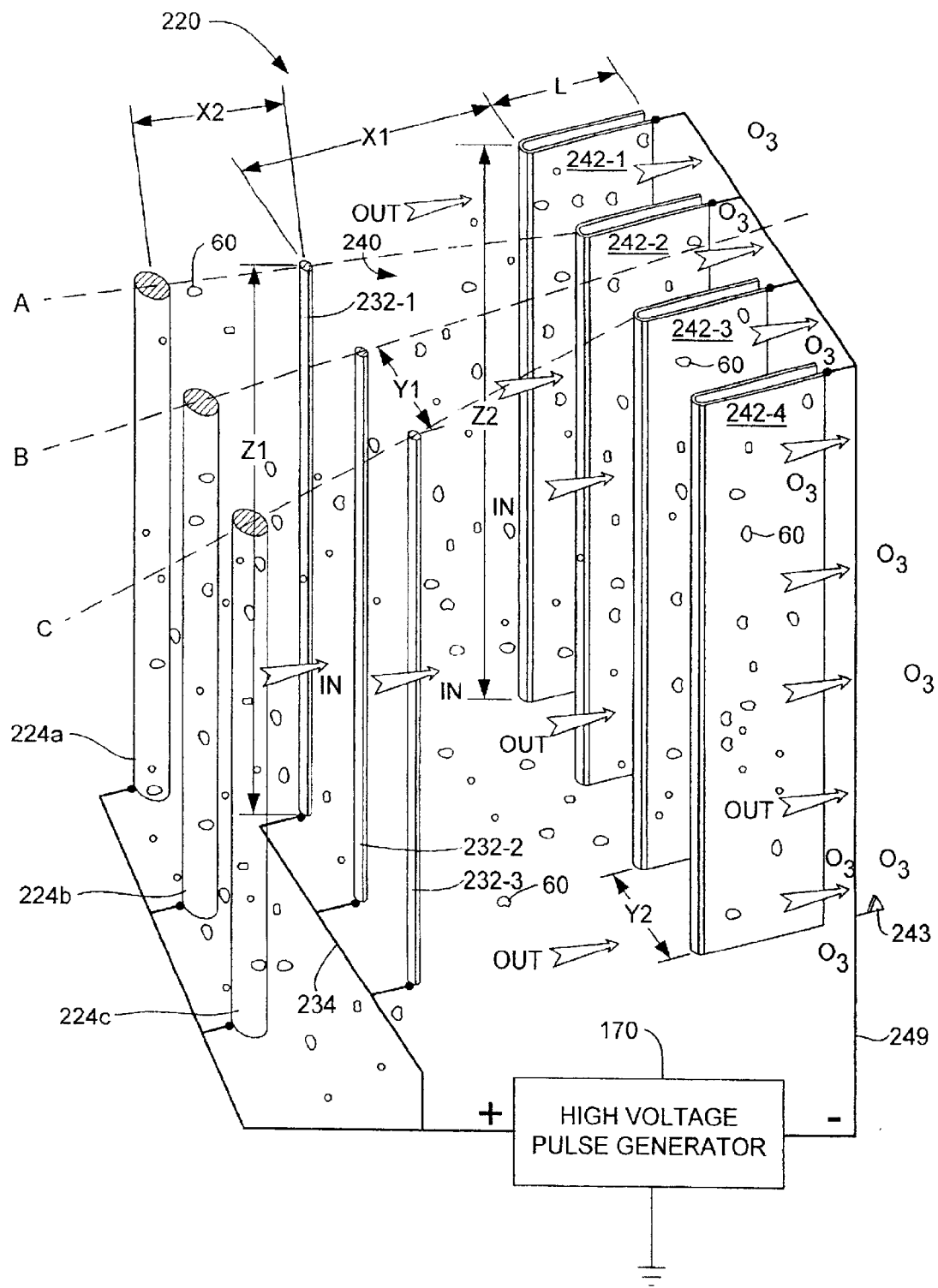
FIGS. 9A–9B.
Figure 9B:
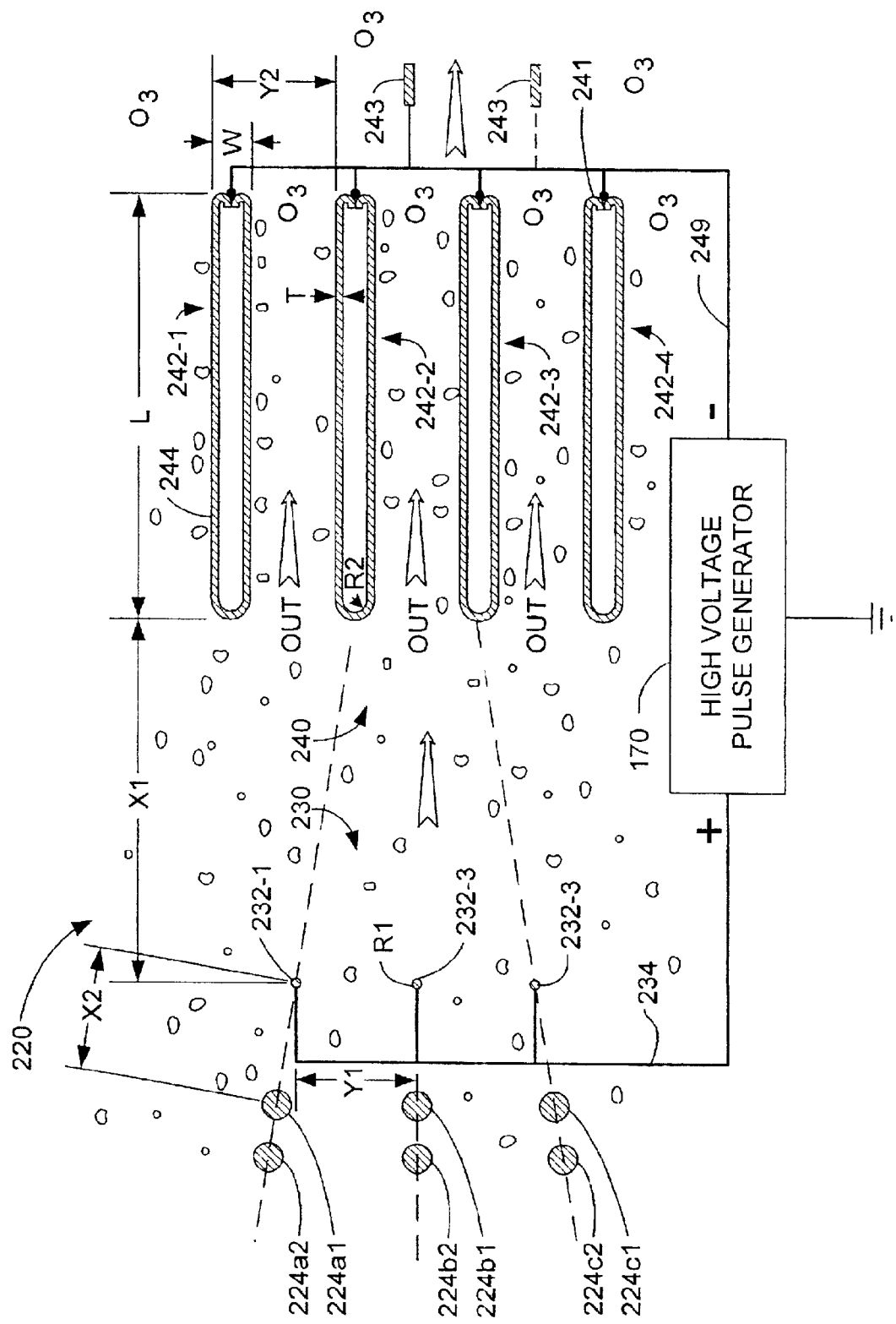

Electrode Assembly with an Upstream Focus Electrode: FIGS. 9A–9B

The embodiments illustrated in FIGS. 9A–9B are somewhat similar to the previously described embodiments in FIGS. 8A–8B. The electrode assembly 220 includes a first array of electrodes 230 and a second array of electrodes 240. Again, for this and the other embodiments, the term "array of electrodes" may refer to a single electrode or a plurality of electrodes. Preferably, the number of electrodes 232 in the first array of electrodes 230 will differ by one relative to the number of electrodes 242 in the second array of electrodes

240. The distances L, X1, Y1, Y2, Z1 and Z2 for this embodiment are similar to those previously described in FIG. 8A.

As shown in FIG. 9A, the electrode assembly 220 preferably adds a third, or leading, or focus, or directional electrode 224*a*, 224*b*, 224*c* (generally referred to as "electrode 224") upstream of each first electrode 232-1, 232-2, 232-3. The focus electrode 224 creates an enhanced airflow velocity exiting the devices 100 or 200. In general, the third focus electrode 224 directs the airflow, and ions generated by the first electrode 232, towards the second electrodes 242. Each third focus electrode 224 is a distance X2 upstream from at least one of the first electrodes 232. The distance X2 is preferably 5–6 mm, or four to five diameters of the focus electrode 224. However, the third focus electrode 224 can be further from, or closer to, the first electrode 232.

The third focus electrode 224 illustrated in FIG. 9A is a rod-shaped electrode. The third focus electrode 224 can also comprise other shapes that preferably do not contain any sharp edges. The third focus electrode 224 is preferably manufactured from material that will not erode or oxidize, such as stainless steel. The diameter of the third focus electrode 224, in a preferred embodiment, is at least fifteen times greater than the diameter of the first electrode 232. The diameter of the third focus electrode 224 can be larger or smaller. The diameter of the third focus electrode 224 is preferably large enough so that third focus electrode 224 does not function as an ion emitting surface when electrically connected with the first electrode 232. The maximum diameter of the third focus electrode 224 is somewhat constrained. As the diameter increases, the third focus electrode 224 will begin to noticeably impair the airflow rate of the units 100 or 200. Therefore, the diameter of the third electrode 224 is balanced between the need to form a non-ion emitting surface and airflow properties of the unit 100 or 200.

In a preferred embodiment, each third focus electrode 224*a*, 224*b*, 224*c* are electrically connected with the first array 230 and the high voltage generator 170 by the conductor 234. As shown in FIG. 9A, the third focus electrodes 224 are electrically connected to the same positive outlet of the high voltage generator 170 as the first array 230. Accordingly, the first electrode 232 and the third focus electrode 224 generate a positive electrical field. Since the electrical fields generated by the third focus electrode 224 and the first electrode 232 are both positive, the positive field generated by the third focus electrode 224 can push, or repel, or direct, the positive field generated by the first electrode 232 towards the second array 240. For example, the positive field generated by the third focus electrode 224*a* will push, or repel, or direct, the positive field generated by the first electrode 232-1 towards the second array 240. In general, the third focus electrode 224 shapes the electrical field generated by each electrode 232 in the first array 230. This shaping effect is believed to decrease the amount of ozone generated by the electrode assembly 220 and increases the airflow of the units 100 and 200.

The particles within the airflow are positively charged by the ions generated by the first electrode 232. As previously mentioned, the positively charged particles are collected by the negatively charged second electrodes 242. The third focus electrode 224 also directs the airflow towards the trailing sides 244 of each second electrode 242. For example, it is believed that the airflow will travel around the third focus electrode 224, partially guiding the airflow towards the trailing sides 244, improving the collection rate of the electrode assembly 220.

The third focus electrode 224 maybe located at various positions upstream of each first electrode 232. Byway of example only, a third focus electrode 224*b* is located directly upstream of the first electrode 232-2 so that the center of the third focus electrode 224*b* is in-line and symmetrically aligned with the first electrode 232-2, as shown by extension line B. Extension line B is located midway between the second electrode 242-2 and the second electrode 242-3. Alternatively, a third focus electrode 224 may also be located at an angle relative to the first electrode 232. For example, a third focus electrode 224*a* maybe located upstream of the first electrode 232-1 along a line extending from the middle of the nose 246 of the second electrode 242-2 through the center of the first electrode 232-1, as shown by extension line A. The third focus electrode 224*a* is in-line and symmetrically aligned with the first electrode 232-1 along extension line A. Similarly, the third electrode 224*c* is located upstream to the first electrode 232-3 along a line extending from the middle of the nose 246 of the second electrode 242-3 through the first electrode 232-3, as shown by extension line C. The third focus electrode 224*c* is in-line and symmetrically aligned with the first electrode 232-3 along extension line C. It is within the scope of the present invention for the electrode assembly 220 to include third focus electrodes 224 that are both directly upstream and at an angle to the first electrodes 232, as depicted in FIG. 9A. Thus, the focus electrodes 224 fan out relative to the first electrodes 232.

FIG. 9B illustrates that an electrode assembly 220 may contain multiple third focus electrodes 224 upstream of each first electrode 232. Byway of example only, the third focus electrode 224*a*2 is in-line and symmetrically aligned with the third focus electrode 224*a*1, as shown by extension line A. In a preferred embodiment, only the third focus electrodes 224*a*1, 224*b*1, 224*c*1 are electrically connected to the high voltage generator 170 by conductor 234. Accordingly, not all of the third electrodes 224 are at the same operating potential. In the embodiment shown in FIG. 9B, the third focus electrodes 224*a*1, 224*b*1, 224*c*1 are at the same electrical potential as the first electrodes 232, while the third focus electrodes 224*a*2, 224*b*2, 224*c*2 are floating. Alternatively, the third focus electrodes 224*a*2, 224*b*2 and 224*c*2 maybe electrically connected to the high voltage generator 170 by the conductor 234.

FIG. 9B illustrates that each second electrode 242 may also have a protective end 241. In the previous embodiments, each "U"-shaped second electrode 242 has an open end. Typically, the end of each trailing side or side wall 244 contains sharp edges. The gap between the trailing sides or side walls 244, and the sharp edges at the end of the trailing sides or side walls 244, generate unwanted eddy currents. The eddy currents create a "backdraft," or airflow traveling from the outlet towards the inlet, which slows down the airflow rate of the units 100 or 200.

In a preferred embodiment, the protective end 241 is created by shaping, or rolling, the trailing sides or side walls 244 inward and pressing them together, forming a rounded trailing end with no gap between the trailing sides or side walls of each second electrode 242. Accordingly, the side walls 244 have outer surfaces, and the end of the side walls 244 are bent back inward and towards the nose 246 so that the outer surface of the side walls 244 are adjacent to, or face, or touch each other to form a smooth trailing edge on the second electrode 242. If desired, it is within the scope of the invention to spot weld the rounded ends together along the length of the second electrode 242. It is also within the scope of the present invention to form the protective end 241 by other methods such as, but not limited to, placing a strap of plastic across each end of the trailing sides 244 for the full length of the second electrode 242. The rounded or capped end is an improvement over the previous electrodes 242 without a protective end 241. Eliminating the gap between the trailing sides 244 also reduces or eliminates the eddy currents typically generated by the second electrode 242. The rounded protective end also provides a smooth surface for purpose of cleaning the second electrode. In a preferred embodiment, the second or collector electrode 242 is a one-piece, integrally formed, electrode with a protective end.

FIGS. 10A–10D

Figure 10A:
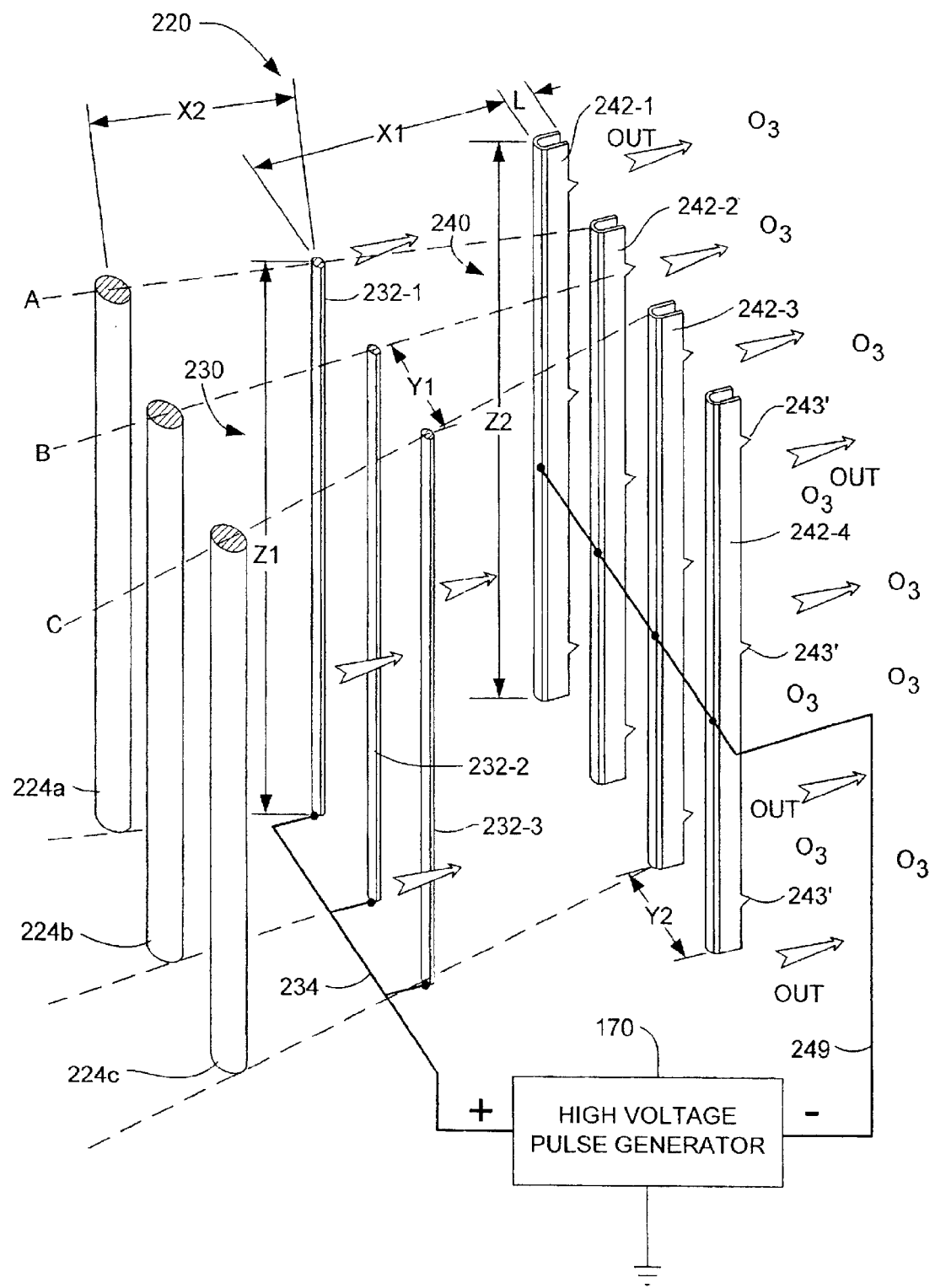
FIGS. 10A–10D.

FIG. 10A illustrates an electrode assembly 220 including a first array of electrodes 230 having three wire-shaped first electrodes 232-1, 232-2, 232-3 (generally referred to as "electrode 232") and a second array of electrodes 240 having four "U"-shaped second electrodes 242-1, 242-2, 242-3, 242-4 (generally referred to as "electrode 242"). Each first electrode 232 is electrically connected to the high voltage generator 170 at the bottom region, whereas each second electrode 242 is electrically connected to the high-voltage generator 170 in the middle to illustrate that the first and second electrodes 232, 242 can be electrically connected in a variety of locations.

The second electrode 242 in FIG. 10A is a similar version of the second electrode 242 shown in FIG. 8C. The distance L has been shortened to about 8 mm, while the other dimensions X1, Y1, Y2, Z1, Z2 are similar to those shown in FIG. 8A.

Figure 10B:
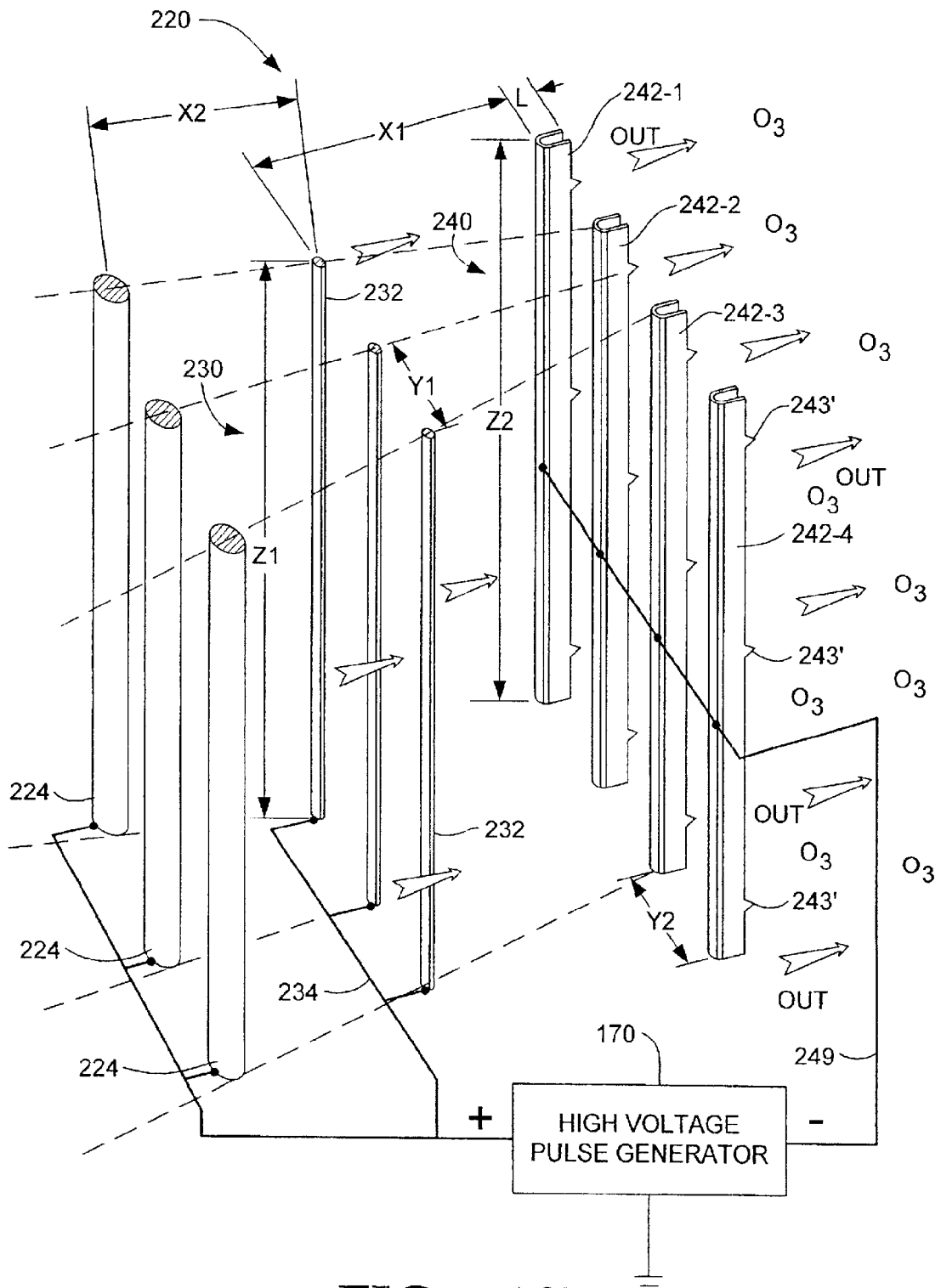

A third leading or focus electrode 224 is located up stream of each first electrode 232. The innermost third focus electrode 224b is located directly upstream of the first electrode 232-2, as shown by extension line B. Extension line B is located midway between the second electrodes 242-2, 242-3. The third focus electrodes 224a, 224c are at an angle with respect to the first electrodes 232-1, 232-3. For example, the third focus electrode 224a is upstream to the first electrode 232-1 along a line extending from the middle of the nose 246 of the second electrode 242-2 extending through the center of the first electrode 232-1, as shown by extension line A. The third electrode 224c is located upstream of the first electrode 232-3 along a line extending from the center of the nose 246 of the second electrode 242-3 through the center of the first electrode 232-3, as shown by extension line C. Preferably, the focus electrodes 224 fan out relative to the first electrodes 232 as an aid for directing the flow of ions and charged particles. FIG. 10B illustrates that the third focus electrodes 224 and the first electrode 232 may be electrically connected to the high voltage generator 170 by conductor 234.

Figure 10C:
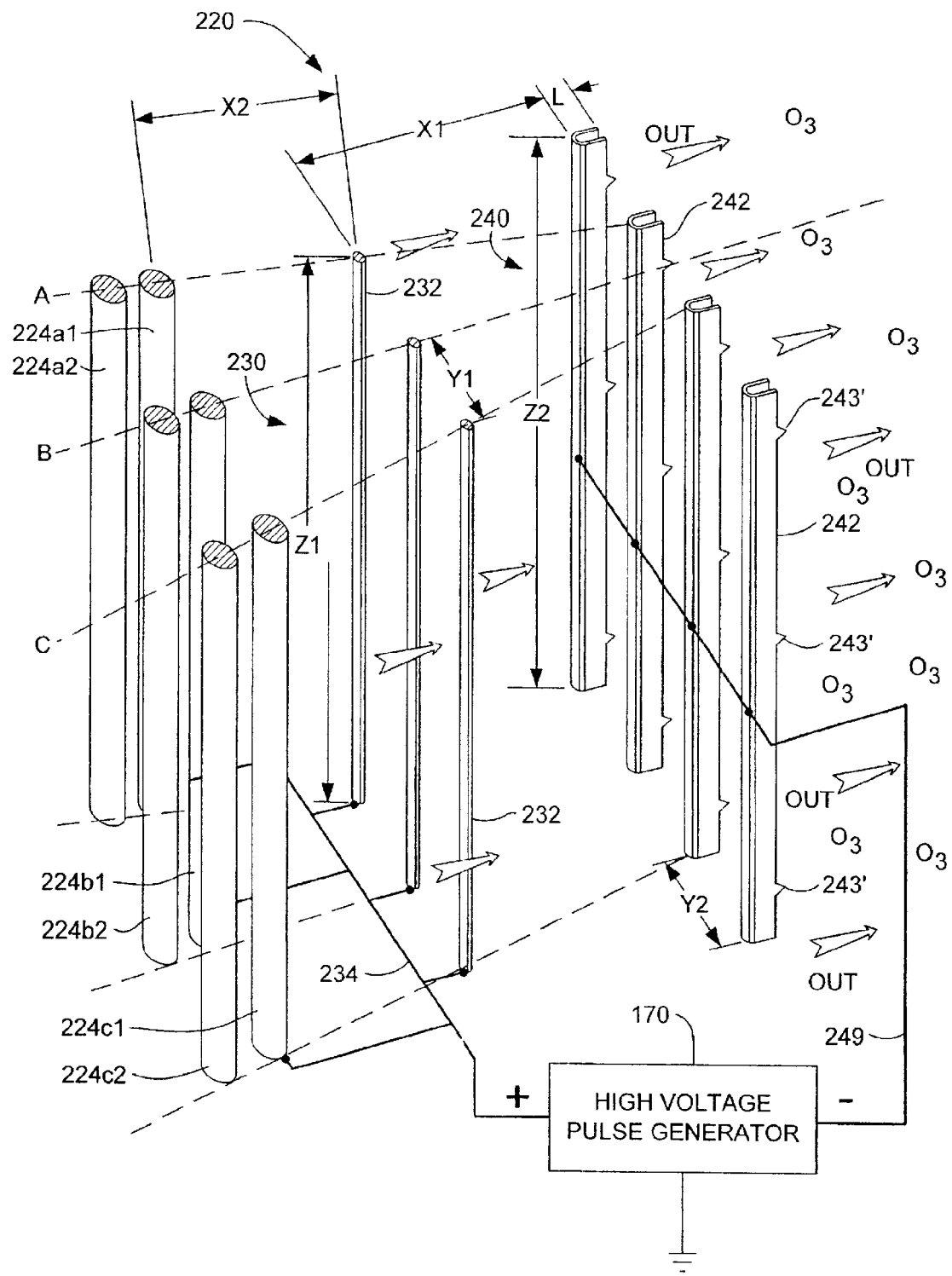

FIG. 10C illustrates that a pair of third focus electrodes 224 may be located upstream of each first electrode 232. Preferably, the multiple third focus electrodes 224 are in-line and symmetrically aligned with each other. For example, the third focus electrode 224a2 is in-line and symmetrically aligned with the third focus electrode 224a1, along extension line A. As previously mentioned, preferably only third focus electrodes 224a1, 224b1, 224c1 are electrically connected with the first electrodes 232 by conductor 234. It is also within the scope of the present invention to have none or all of the third focus electrodes 224 electrically connected to the high voltage generator 170.

Figure 10D:
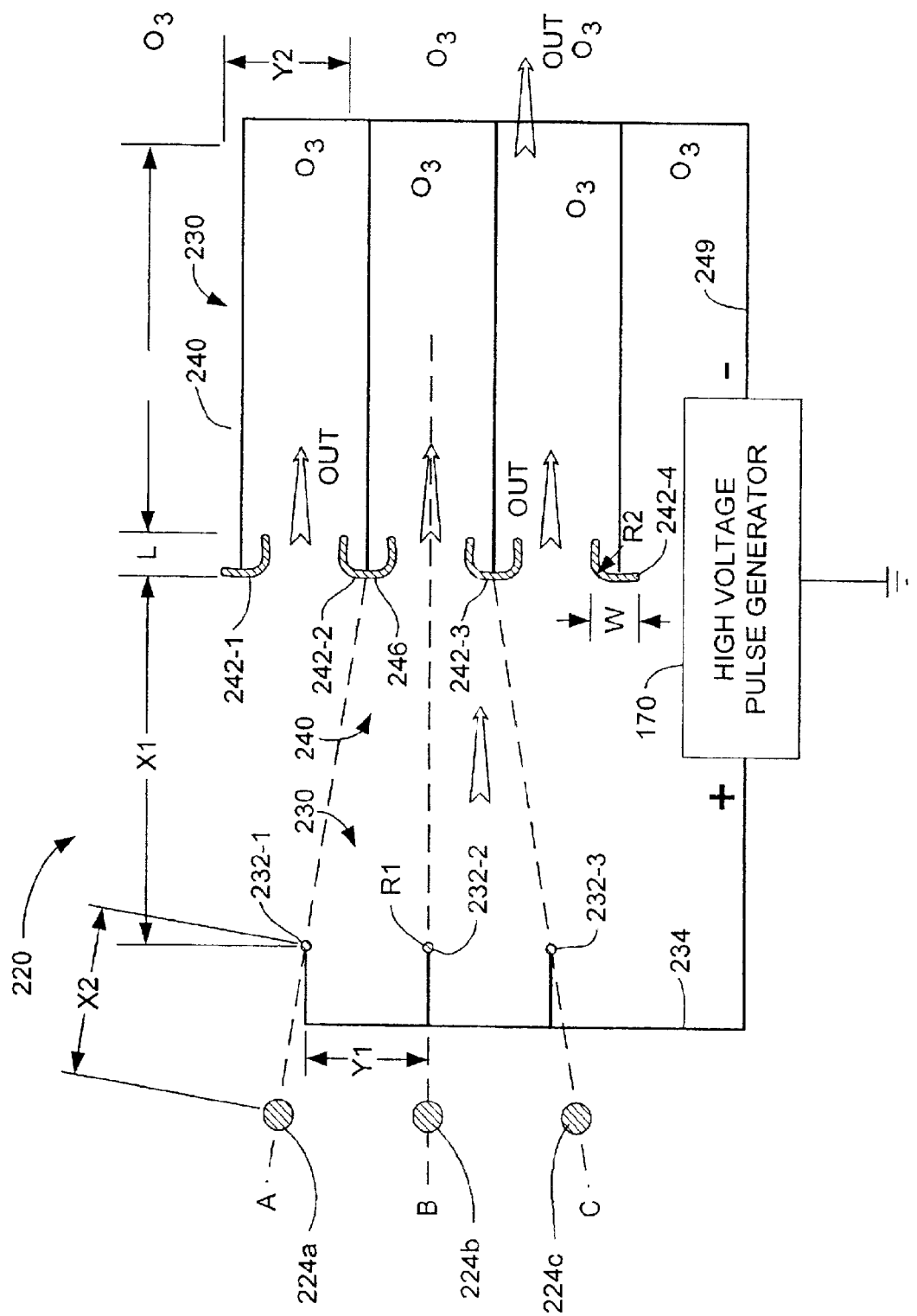

FIG. 10D illustrates third focus electrodes 224 added to the electrode assembly 220 shown in FIG. 8D. Preferably, a third focus electrode 224 is located upstream of each first electrode 232. For example, the third focus electrode 224b is in-line and symmetrically aligned with the first electrode 232-2, as shown by extension line B. Extension line B is located midway between the second electrodes 242-2, 242-3. The third focus electrode 224a is in-line and symmetrically aligned with the first electrode 232-1, as shown by extension line A. Similarly, the third electrode 224c is in-line and symmetrically aligned with the first electrode 232-3, as shown by extension line C. Extension lines A and C extend from the middle of the nose 246 of the "U"-shaped second electrodes 242-2, 242-3 through the first electrodes 232-1, 232-3, respectively. In a preferred embodiment, the third electrodes 224a, 224b, 224c with the high voltage generator 170 by the conductor 234. This embodiment can also include a pair of third focus electrodes 224 upstream of each first electrode 232 similar to the embodiment depicted in FIG. 10C.

FIGS. 11A–11C

Figure 11A:
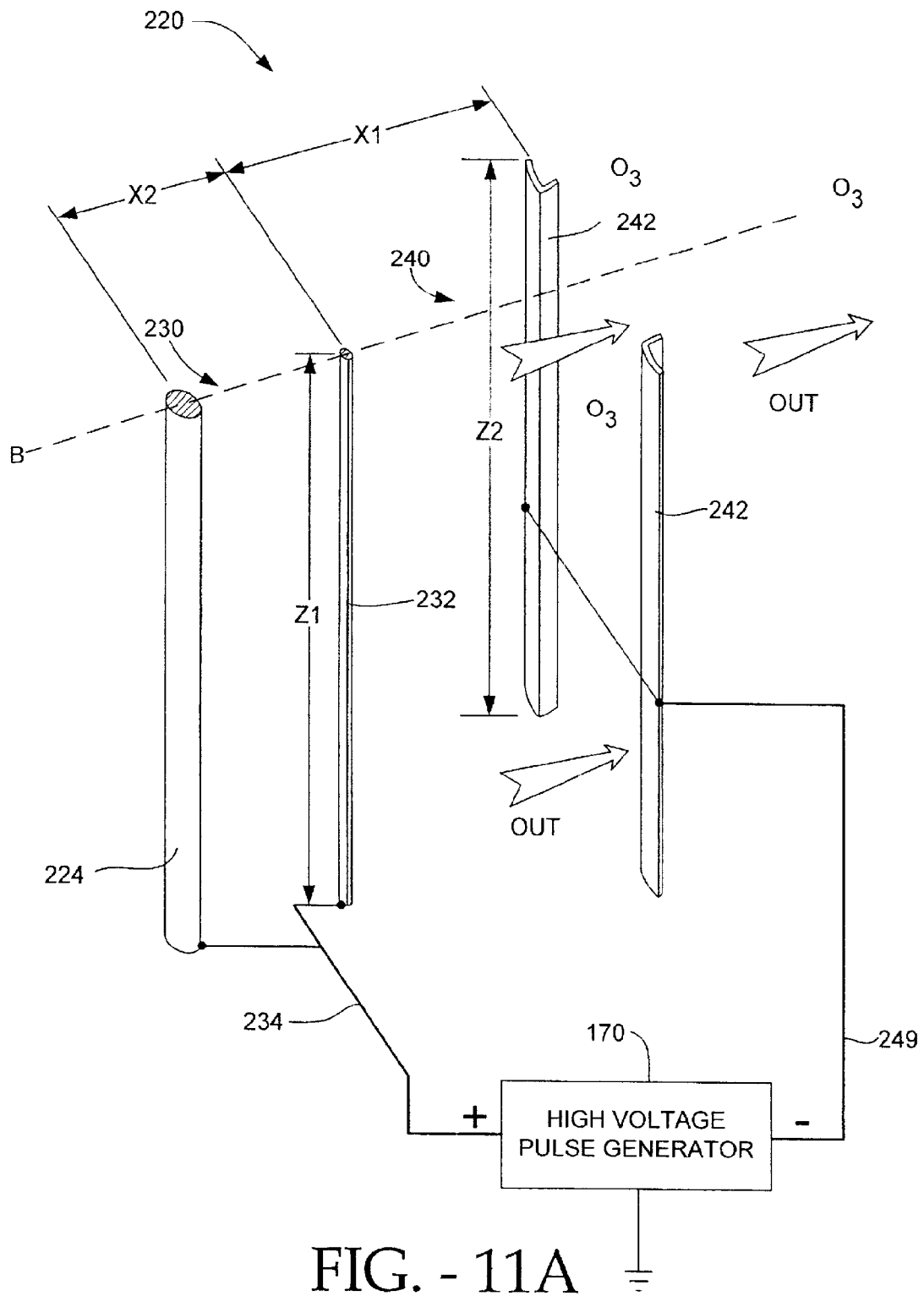
FIGS. 11A–11C.
Figure 11B:
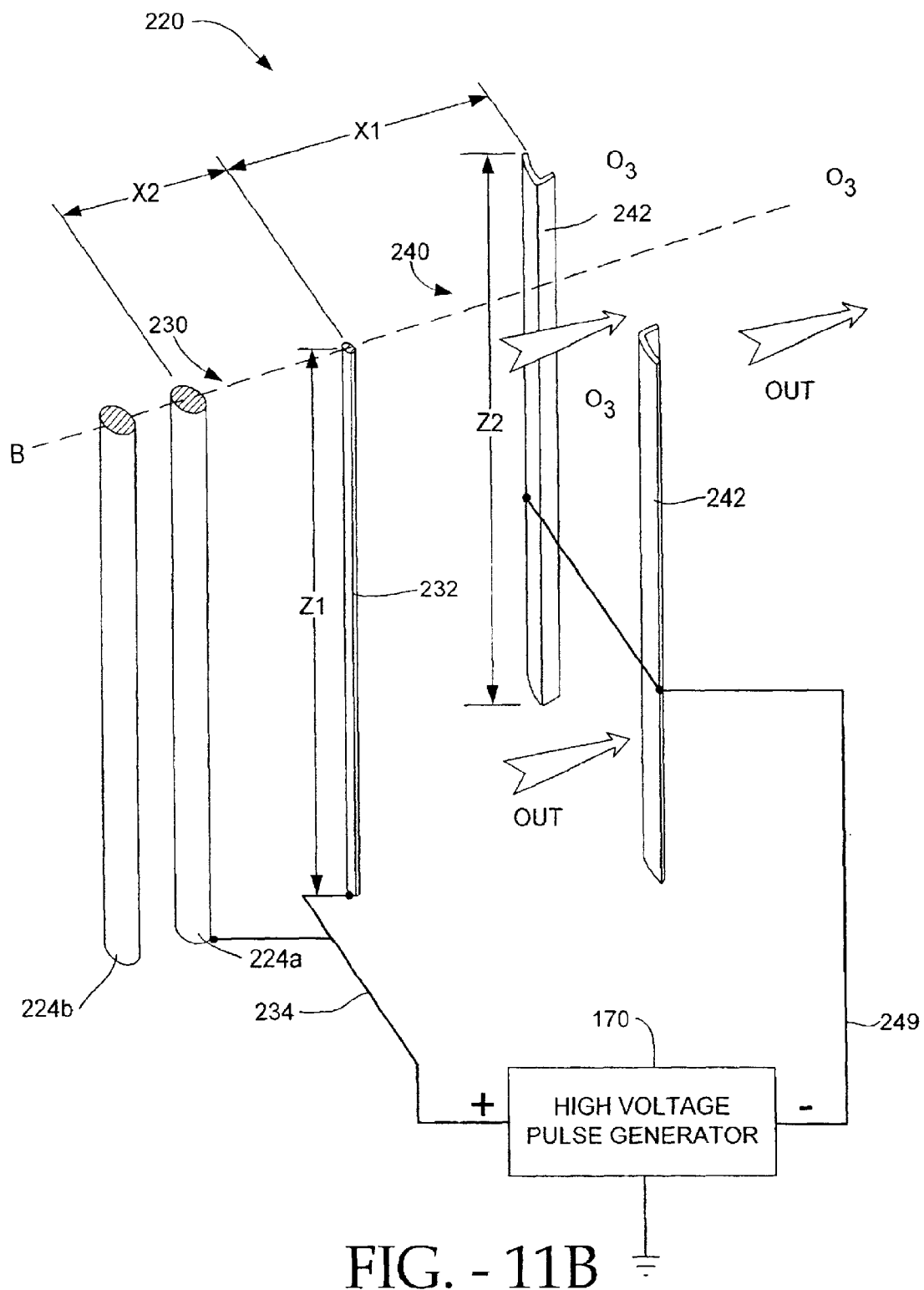
Figure 11C:
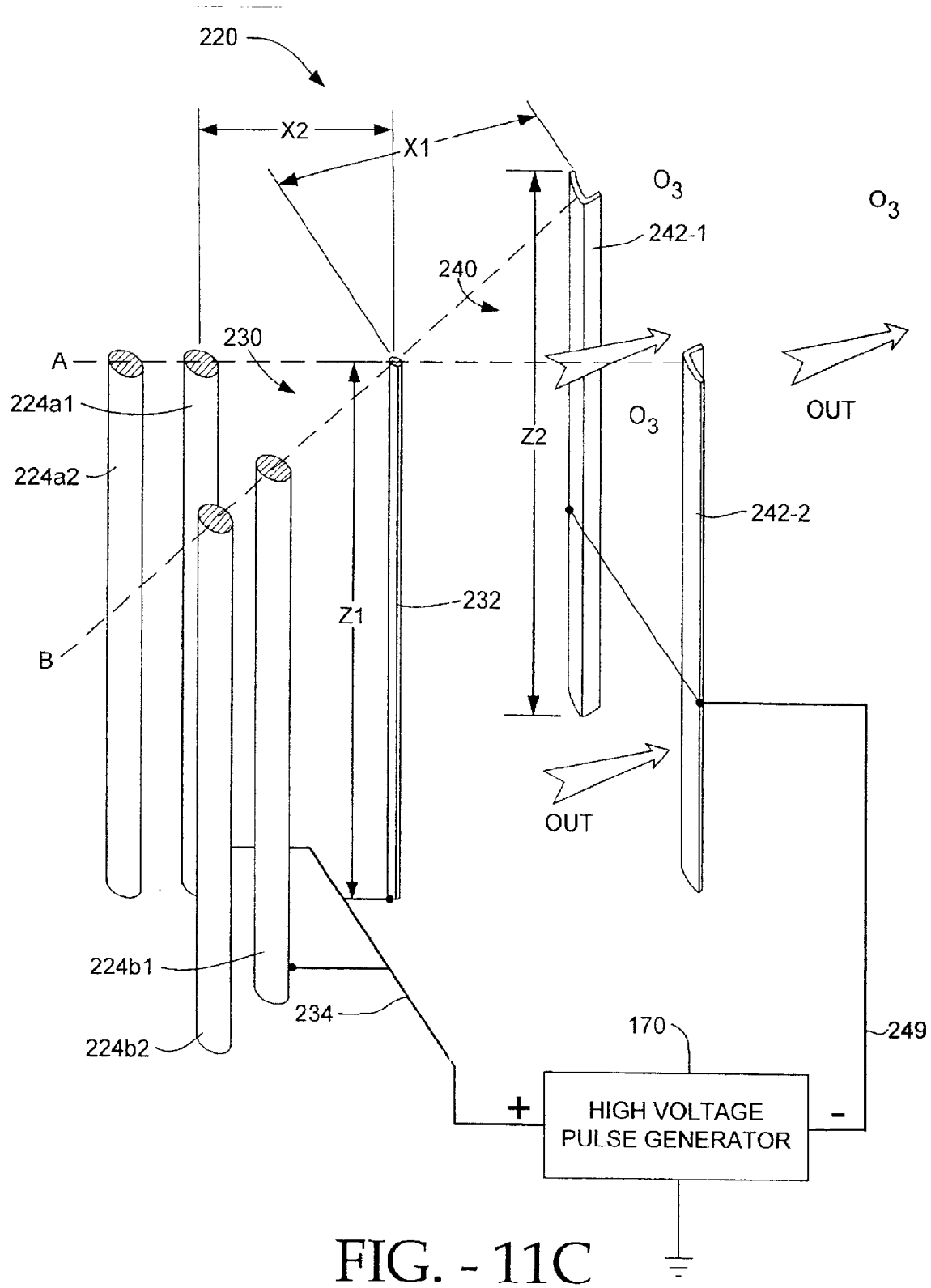

FIGS. 11A–11C illustrate that the electrode assembly 220 shown in FIG. 8E may include a third focus electrode 224 upstream of the first array of electrodes 230 comprising a single wire electrode 232. Preferably, the center of the third focus electrode 224 is in-line and symmetrically aligned with the center of the first electrode 232, as shown by extension line B. Extension line B is located midway between the second electrodes 242. The distances X1, X2, Y1, Y2, Z1 and Z2 are similar to the embodiments previously described. The first electrode 232 and the second electrodes 242 maybe electrically connected to the high-voltage generator 170 by conductor 234, 249 respectively. It is within the scope of the present invention to connect the first and second electrodes to opposite ends of the high voltage generator 170 (e.g., the first electrode 232 maybe negatively charged and the second electrode 242 maybe positively charged). In a preferred embodiment, the third focus electrode 224 is also electrically connected to the high voltage generator 170.

FIG. 11B illustrates that a pair of third focus electrodes 224a, 224b maybe located upstream of the first electrode 232. The third focus electrodes 224a, 224b are in-line and symmetrically aligned with the first electrode 232, as shown by extension line B. Extension line B is located midway between the second electrodes 242. Preferably, the third focus electrode 224b is upstream of third focus electrode 224a a distance equal to the diameter of a third focus electrode 224. In a preferred embodiment, only the third focus electrode 224a is electrically connected to the high voltage generator 170. It is within the scope of the present invention to electrically connect both third focus electrodes 224a, 224b to the high voltage generator 170.

FIG. 11C illustrates that each third focus electrode 224 can be located at an angle with respect to the first electrode 232. Similar to the previous embodiments, the third focus electrode 224a1 and 224b1 is located a distance X2 upstream from the first electrode 232. By way of example only, the third focus electrodes 224a1, 224a2 are located along a line extending from the middle of the second electrode 242-2 through the center of the first electrode 232, as shown by extension line A. Similarly, the third focus electrodes 224b1, 224b2 are along a line extending from the middle of the second electrode 242-1 through the middle of the first electrode 232, as shown by extension line B. The third focus electrode 224a2 is in-line and symmetrically aligned with the third focus electrode 224a1 along extension line A. Similarly, the third focus electrode 224b2 is in line and symmetrically aligned with the third focus electrode 224b1, along extension line B. The third focus electrodes 224 are fanned out and form a "V" pattern upstream of first electrode 232. In a preferred embodiment, only the third focus electrodes 224a1 and 224b1 are electrically connected to the high-voltage generator 170 by conductor 234. It is within the scope and spirit of the invention to electrically connect the third focus electrodes 224a and 224b2 to the high voltage generator 170.

FIGS. 12A–12B

Figure 12A:
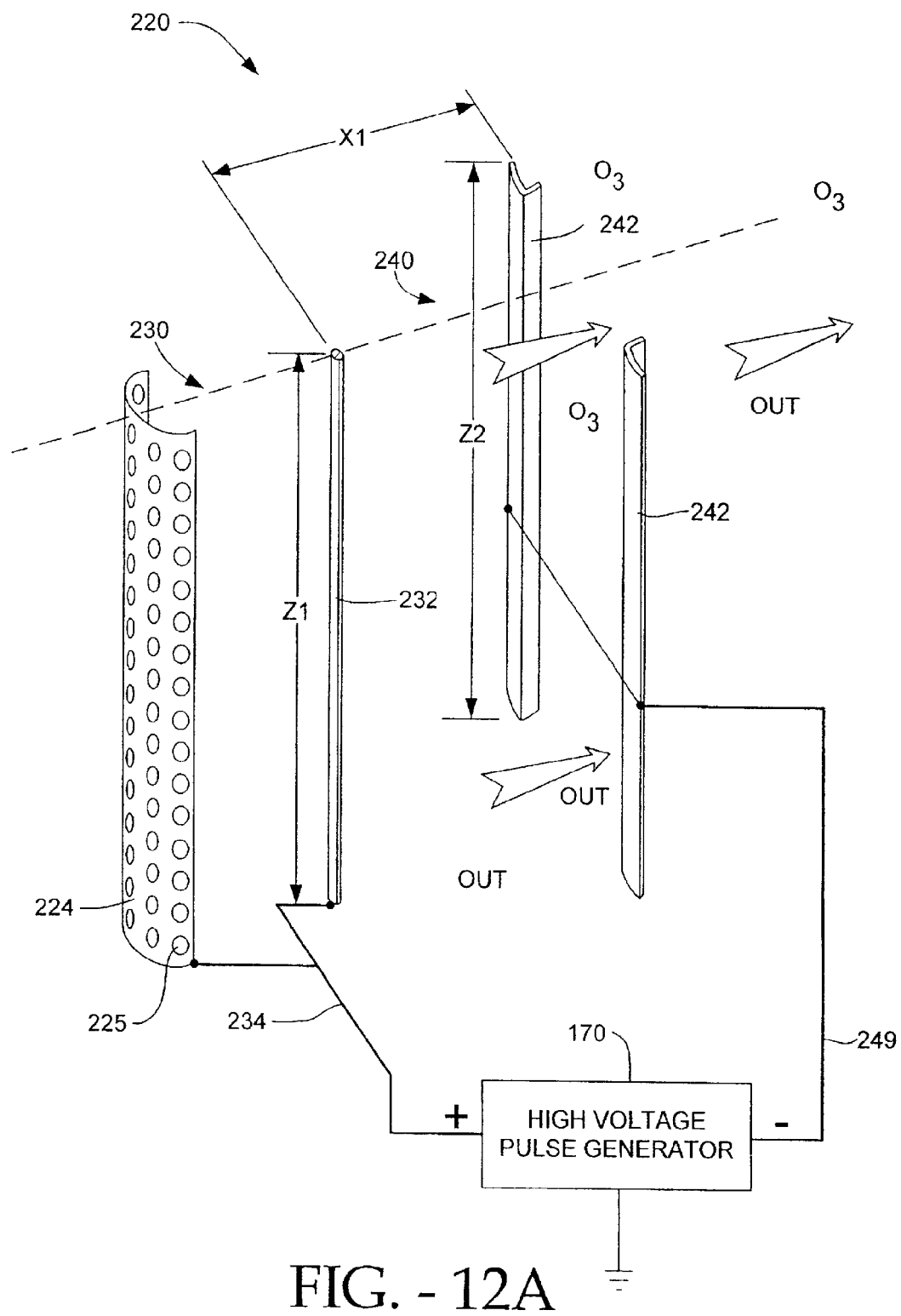
FIGS. 12A–12C.

The previously described embodiments of the electrode assembly 220 disclose a rod-shaped third focus electrode 224 upstream of the first array of electrodes 230. FIG. 12A illustrates an alternative configuration for the third focus electrode 224. By way of example only, the electrode assembly 220 may include a "U"-shaped or possibly "C"-shaped third focus electrode 224 upstream of each first electrode 232. The third focus electrode 224 may also have other curved configurations such as, but not limited to, circular-shaped, elliptical-shaped, parabolically-shaped, and other concave shapes facing the first electrode 232. In a preferred embodiment, the third focus electrode 224 has holes 225 extending through, forming a perforated surface to minimize the resistance of the third focus electrode 224 on the airflow rate.

In a preferred embodiment, the third focus electrode 224 is electrically connected to the high voltage generator 170 by conductor 234. The third focus electrode 224 in FIG. 12A is preferably not an ion emitting surface. Similar to previous embodiments, the third focus electrode 224 generates a positive electric field and pushes or repels the electric field generated by the first electrode 232 towards the second array 240.

Figure 12B:
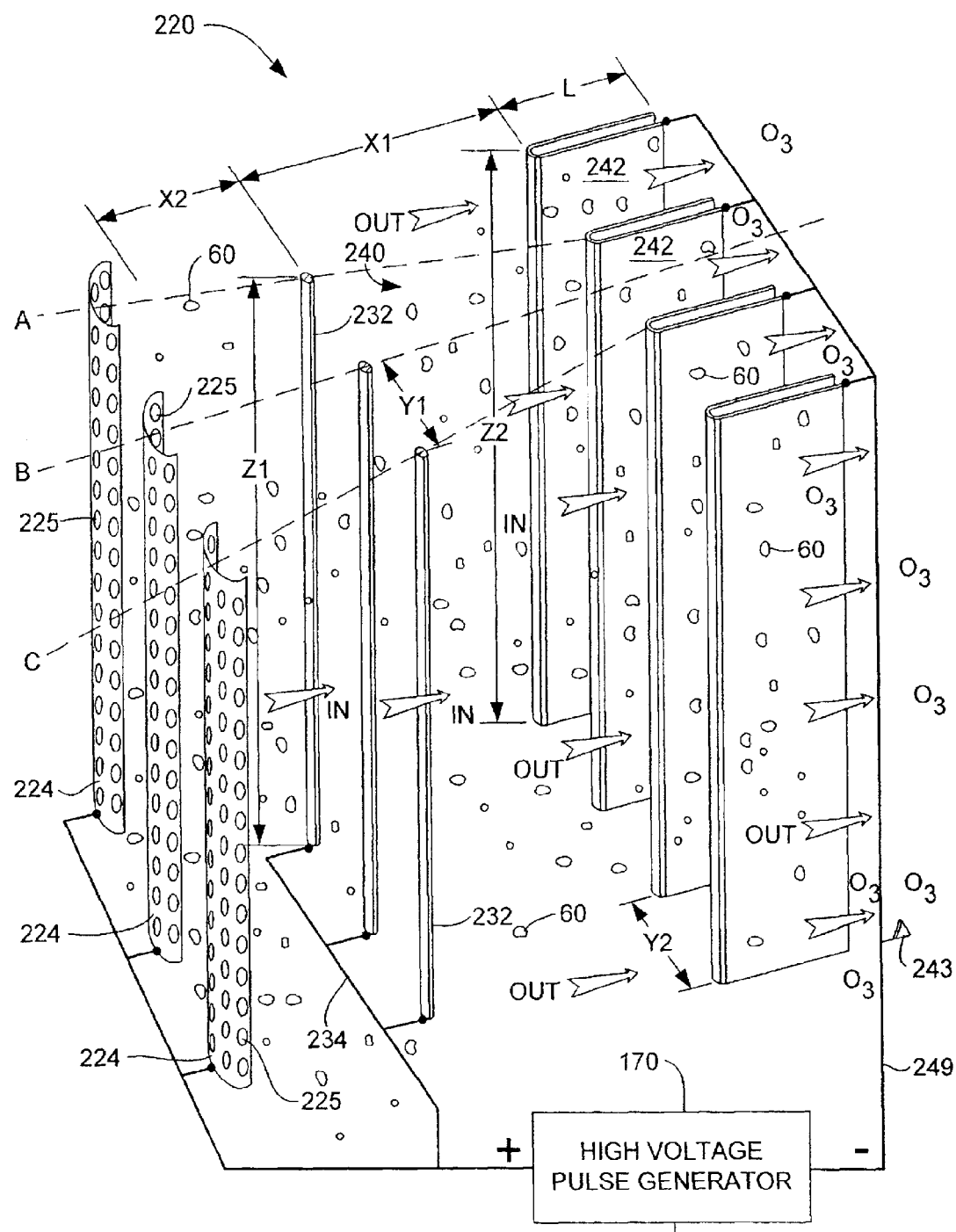

FIG. 12B illustrates that a perforated "U"-shaped or "C"-shaped third focus electrode 224 can be incorporated into the electrode assembly 220 shown in FIG. 8A. Even though only two configurations of the electrode assembly 220 are shown with the perforated "U"-shaped third focus electrode 224, all the embodiments described in FIGS. 8A–15C may incorporate the perforated "U"-shaped third focus electrode 224. It is also within the scope of the invention to have multiple perforated "U"-shaped third focus electrodes 224 upstream of each first electrode 232. Further in other embodiments the "U"-shaped third focus electrode 224 can be made of a screen or a mesh.

Figure 12C:
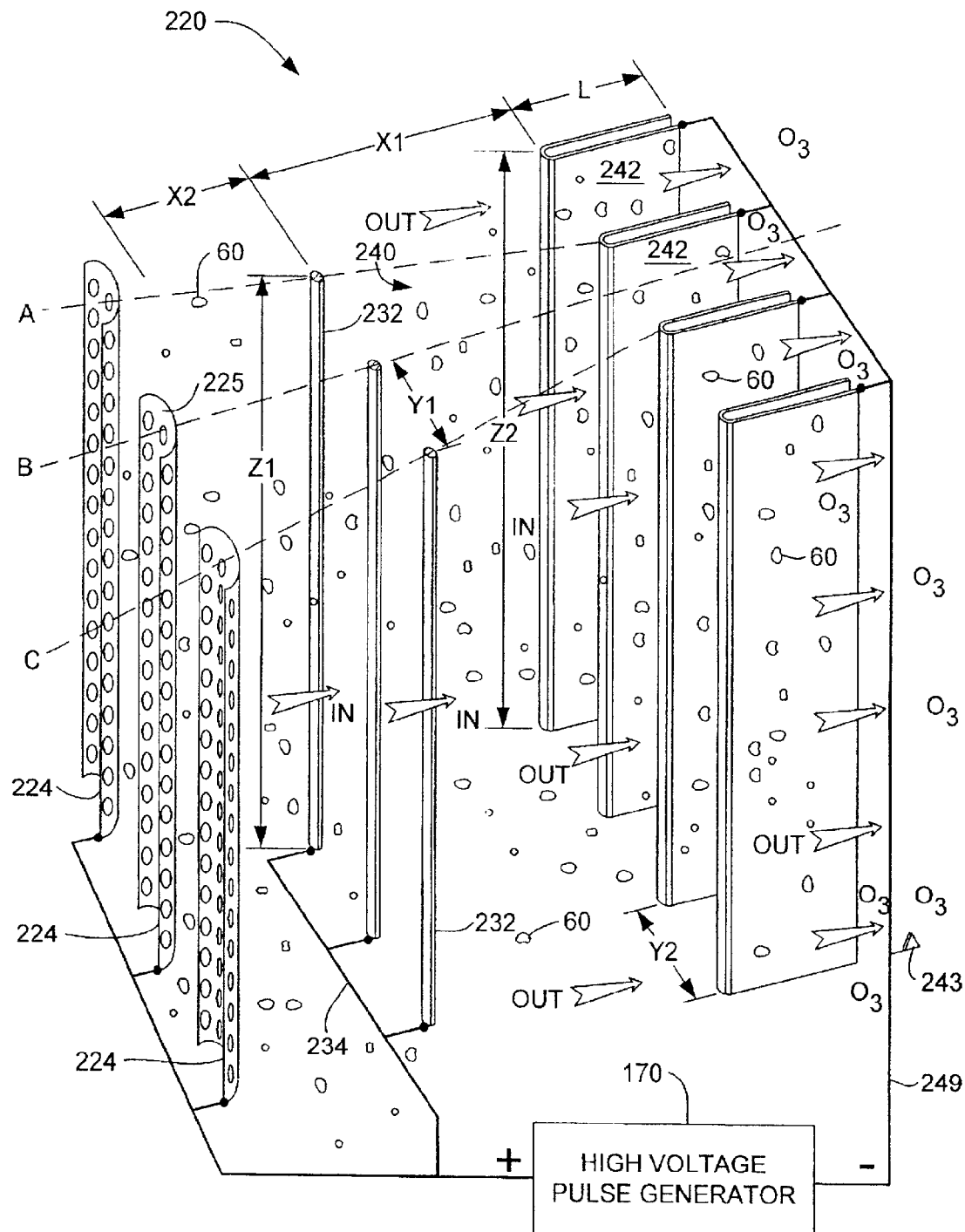

FIG. 12C illustrates third focus electrodes 224 similar to those depicted in FIG. 12B, except that the third focus electrodes 224 are rotated by 180° to preset a convex surface facing to the first electrodes 232 in order to focus and direct the field of ions and airflow from the first electrode 232 toward the second array of electrodes 240. These third focus electrodes 224 shown in FIGS. 12A–12C are located along extension lines A, B, C similar to previously described embodiments.

Figure 13A:
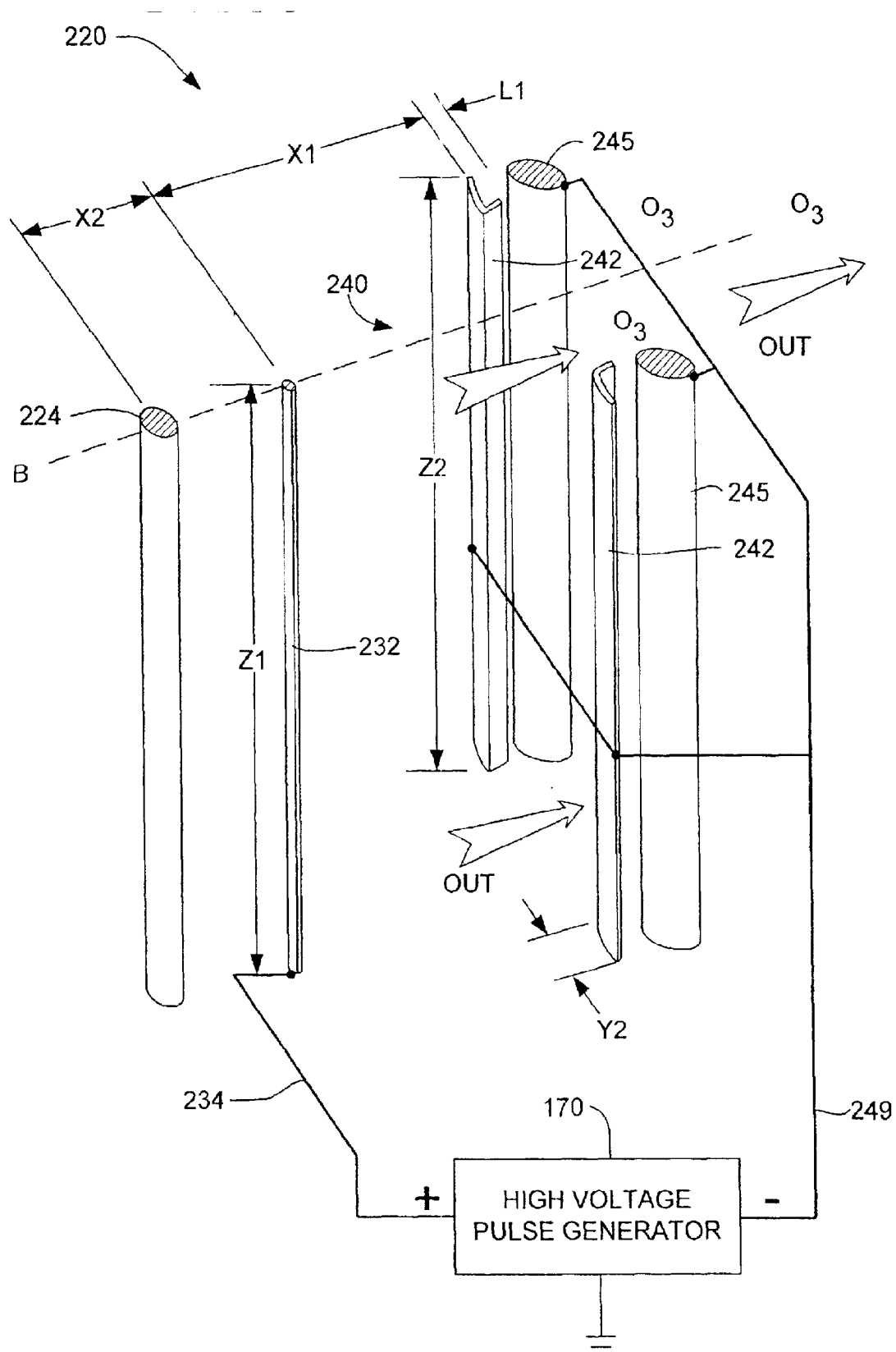
FIGS. 13A–13C.
Figure 13B:
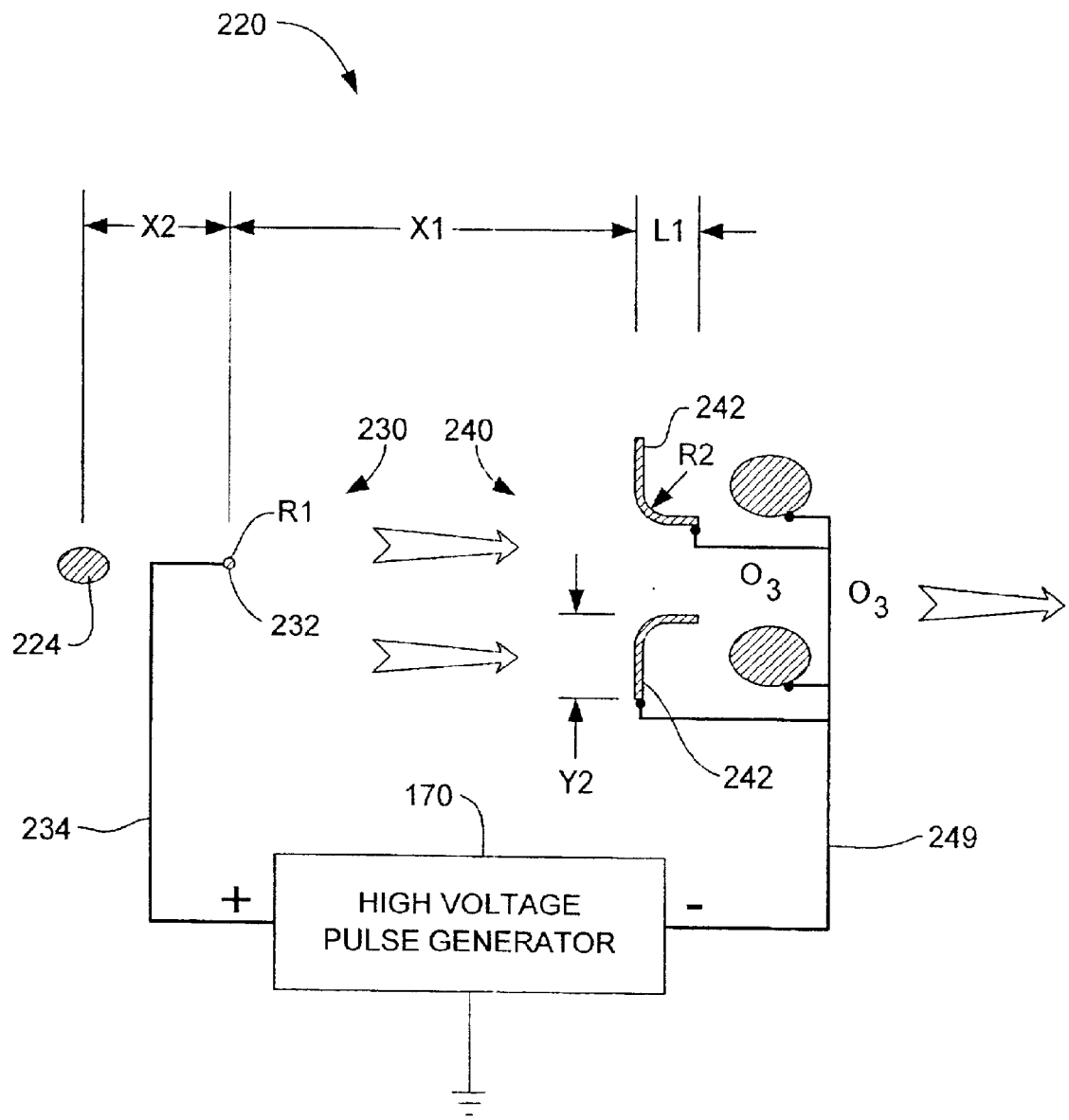
Figure 13C:
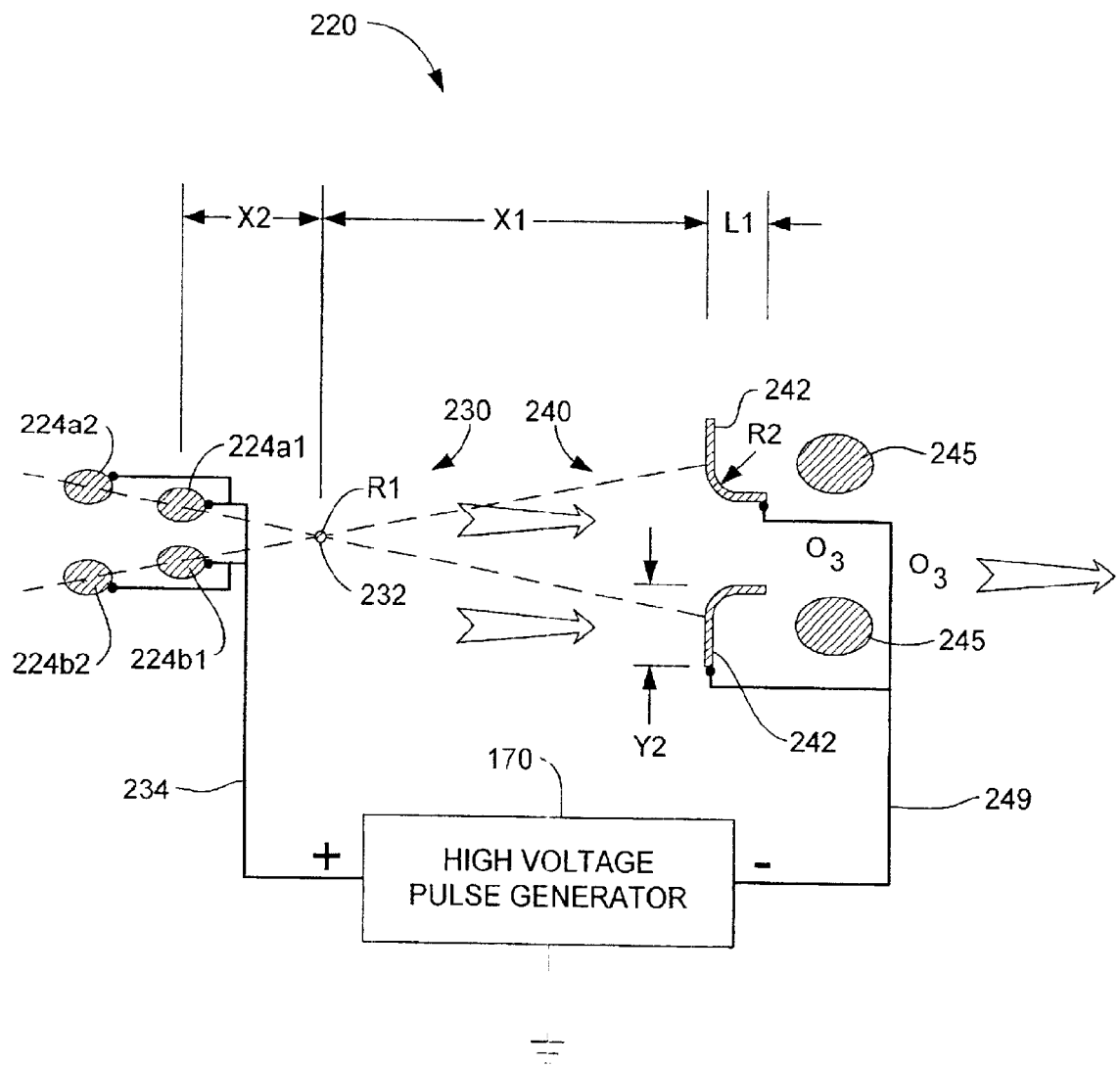

Electrode Assembly with a Downstream Trailing Electrode: FIGS. 13A–13C

FIGS. 13A–13C illustrate an electrode assembly 220 having an array of trailing electrodes 245 added to an electrode assembly 220 similar to that shown in FIG. 11A. It is understood that an alternative embodiment similar to FIG. 13A may include a trailing electrode or electrodes without any focus electrodes and be within the spirit and scope of the invention.

Referring now to FIGS. 13A–13B, each trailing electrode 245 is located downstream of the second array of electrodes 240. Preferably, the trailing electrodes 245 are located downstream from each second electrode 242 by at least three times the radius R2 (see FIG. 13B). Further, the trailing electrodes 245 are preferably directly downstream of each second electrode 242 so as not to interfere with the flow of air. Also, the trailing electrode 245 is aerodynamically smooth, for example, circular, elliptical, or teardrops shaped in cross-section so as not to unduly interfere with the smoothness of the airflow thereby. In a preferred embodiment, the trailing electrodes 245 are electrically connected to the same outlet of the high voltage generator 170 as the second array of electrodes 240. As shown in FIG. 13A, the second electrodes 242 and the trailing electrodes 245 have a negative electrical charge. This arrangement can introduce more negative charges into the air stream. Alternatively, the trailing electrodes 245 can have a floating potential if they are not electrically connected to the second electrode 242 or the high voltage generator 170. The trailing electrodes 245 can also be grounded in other embodiments.

When the trailing electrodes 245 are electrically connected to the high voltage generator 170, the positively charged particles within the airflow are also attracted to, and collect on, the trailing electrodes 245. In an electrode assembly 220 with no trailing electrode 245, most of the particles will collect on the surface area of the second electrodes 242. However, some particles will pass through the unit 200 without being collected by the second electrodes 242. Thus, the trailing electrodes 245 serve as a second surface area to collect the positively charged particles. The trailing electrodes 245, having the same polarity as the second electrodes 242, also deflect charged particles toward the second electrodes 242.

The trailing electrodes 245 preferably also emit a small amount of negative ions into the airflow. The negative ions emitted by the trailing electrode 245 attempt to neutralize the positive ions emitted by the first electrodes 232. If the positive ions emitted by the first electrodes 232 are not neutralized before the airflow reaches the outlet 260, the outlet fins 212 may become electrically charged, and particles within the airflow may tend to stick to the fins 212. If this occurs, the particles collected by the fins 212 will eventually block or minimize the airflow exiting the unit 200.

FIG. 13C illustrates another embodiment of the electrode assembly 200, having trailing electrodes 245 added to an embodiment similar to that shown in FIG. 11C. The trailing electrodes 245 are located downstream of the second array 240 similar to the previously described embodiments above. It is within the scope of the present invention to electrically connect the trailing electrodes 245 to the high voltage generator 170. The trailing electrodes 245 emit negative ions to neutralize the positive ions emitted by the first electrode 232. As shown in FIG. 13C, all of the third focus electrodes 224 are electrically connected to the high voltage generator 170. In a preferred embodiment, only the third focus electrodes 224a1, 224b1 are electrically connected to the high voltage generator 170, and the third focus electrodes 224a2, 224b2 have a floating potential.

Figure 14A:
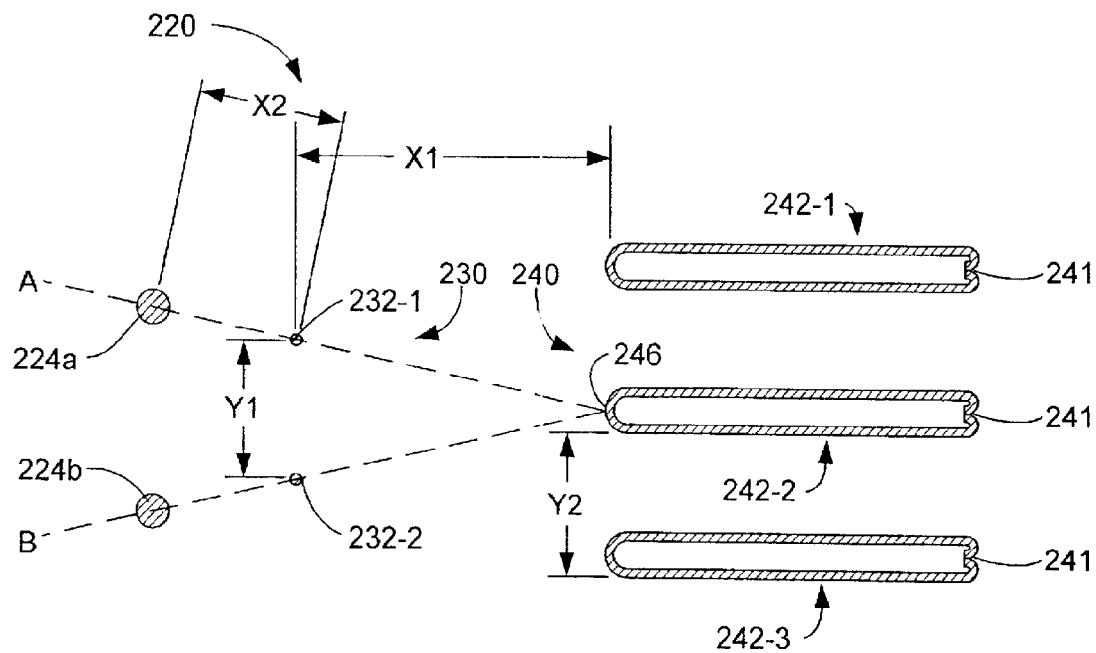
FIGS. 14A–14F.

Electrode Assemblies with Various Combinations of Focus Electrodes, Trailing Electrodes and Enhanced Second Electrodes with Protective Ends:
FIGS. 14A–14D FIG. 14A illustrates an electrode assembly 220 that includes a first array of electrodes 230 having two wire-shaped electrodes 232-1, 232-2 (generally referred to as "electrode 232") and a second array of electrodes 240 having three "U"-shaped electrodes 2421, 242-2, 242-3 (generally referred to as "electrode 242"). Upstream from each first electrode 232, at a distance X2, is a third focus electrode 224. Each third focus electrode 224a, 224b is at an angle with respect to a first electrode 232. For example, the third focus electrode 224a is preferably along a line extending from the middle of the nose 246 of the innermost second electrode 242-2 through the center of the first electrode 232-1, as shown by extension line A. The third focus electrode 224a is in-line and symmetrically aligned with the first electrode 232-1 along extension line A. Similarly, the third focus electrode 224b is located along a line extending from middle of the nose 246 of the second electrode 242-2 through the center of the first electrode 232-2, as shown by extension line B. The third focus electrode 224b is in-line and symmetrically aligned with the first electrode 232-2 along extension line B. As previously described, the diameter of each third focus electrode 224 is preferably at least fifteen times greater than the diameter of the first electrode 232. As shown in FIG. 14A, and similar to the embodiment shown in FIG. 9B, each second electrode preferably has a protective end 241. Similar to previous embodiments, the third focus electrodes 224 are preferably electrically connected to the high voltage generator 170. It is within the spirit and scope of the invention to not electrically connect the third focus electrodes 224 with the high voltage generator 170.

Figure 14B:
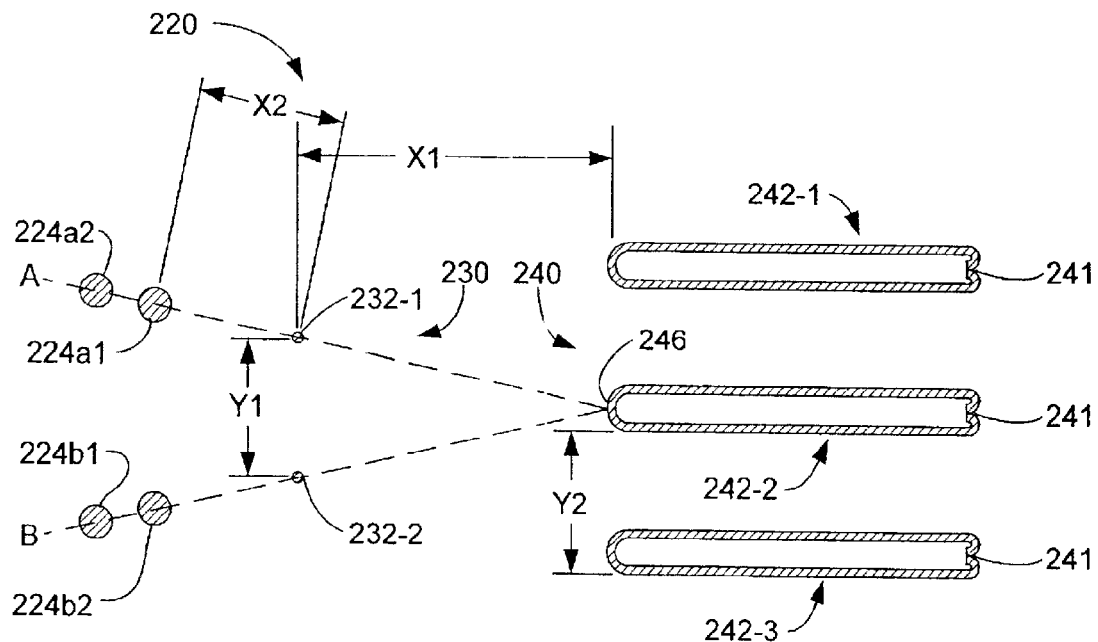

FIG. 14B illustrates that multiple third focus electrodes 224 maybe be located upstream of each first emitter electrode 232. For example, the third focus electrode 224a2 is in-line and symmetrically aligned with the third focus electrode 224a1 along extension line A. Similarly, the third focus electrode 224b2 is in-line and symmetrically aligned with the third focus electrode 242b1 along extension line B. It is within the scope of the present invention to electrically connect all, or none of, the third focus electrodes 224 to the high-voltage generator 170. In a preferred embodiment, only the third focus electrodes 224a1, 224b1 are electrically connected to the high voltage generator 170, while the third focus electrodes 224a2, 224b2 have a floating potential.

Figure 14C:
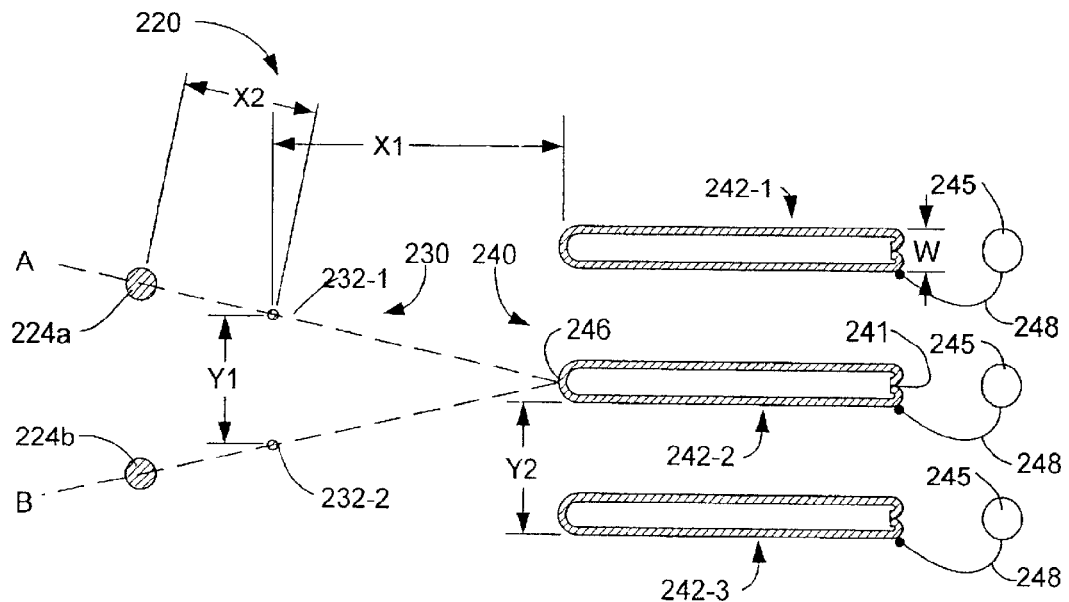

FIG. 14C illustrates that the electrode assembly 220 shown in FIG. 14A may also include a trailing electrode 245 downstream of each second electrode 242. Each trailing electrode 245 is in-line with the second electrode 242 to minimize the interference with the airflow passing the second electrode 242. Each trailing electrode 245 is preferably located a distance downstream of each second electrode 242 equal to at least three times the width W of the second electrode 242. It is within the scope of the present invention to locate the trailing electrode 245 at other distances downstream of the second electrode 242. The diameter of the trailing electrode 245 is preferably no greater than the width W of the second electrode 242 to limit the interference of the airflow coming off the second electrode 242.

Another aspect of the trailing electrode 245 is to direct the air trailing off the second electrode 242 to provide a more laminar flow of air exiting the outlet 260. Yet another aspect of the trailing electrode 245, as previously mentioned above, is to neutralize the positive ions generated by the first array 230 and collect particles within the airflow. As shown in FIG. 14C, each trailing electrode 245 is electrically connected to a second electrode 242 by a conductor 248. Similar to previous embodiments, the trailing electrode 245 has the same polarity as the second electrode 242, and serves as a collecting surface, similar to the second electrode 242, to attract the oppositely charged particles in the airflow. Alternatively, the trailing electrode may be connected to a ground or having a floating potential.

Figure 14D:
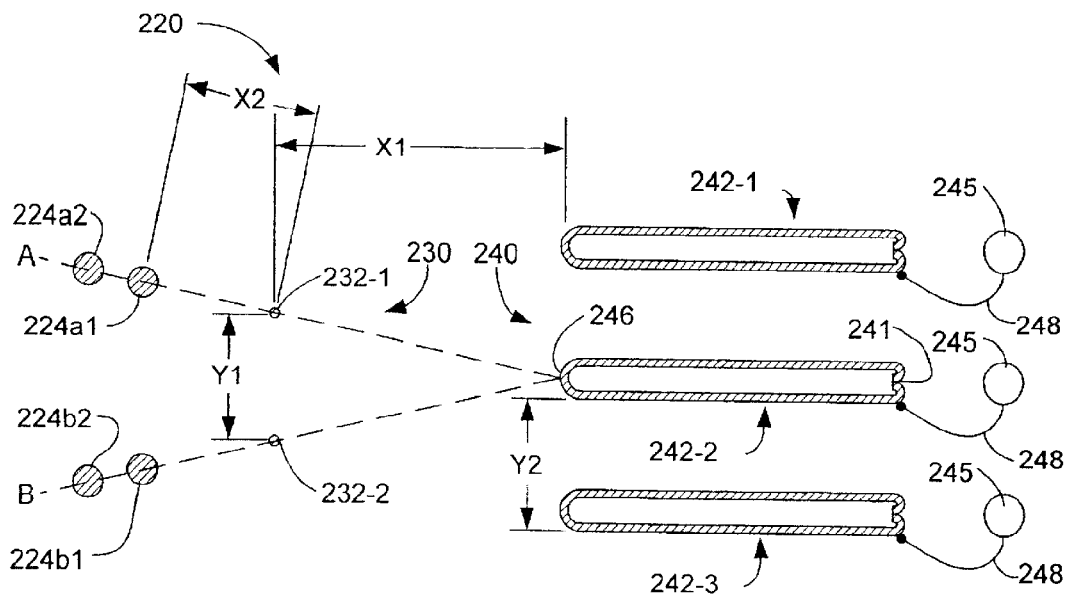

FIG. 14D illustrates that a pair of third focus electrodes 224 maybe be located upstream of each first electrode 232. For example, the third focus electrode 224a2 is upstream of the third focus electrode 224a1 so that the third focus electrodes 224a1, 224a2 are in-line and symmetrically aligned with each other along extension line A. Similarly, the third focus electrode 224b2 is in line and symmetrically aligned with the third focus electrode 224b1 along extension line B. As previously described, preferably only the third focus electrodes 224a1, 224b1 are electrically connected to the high voltage generator 170, while the third focus electrodes 224a2, 224b2 have a floating potential. It is within the spirit and scope of the present invention to electrically connect all, or none, of the third focus electrodes to the high voltage generator 170.

Figure 14E:
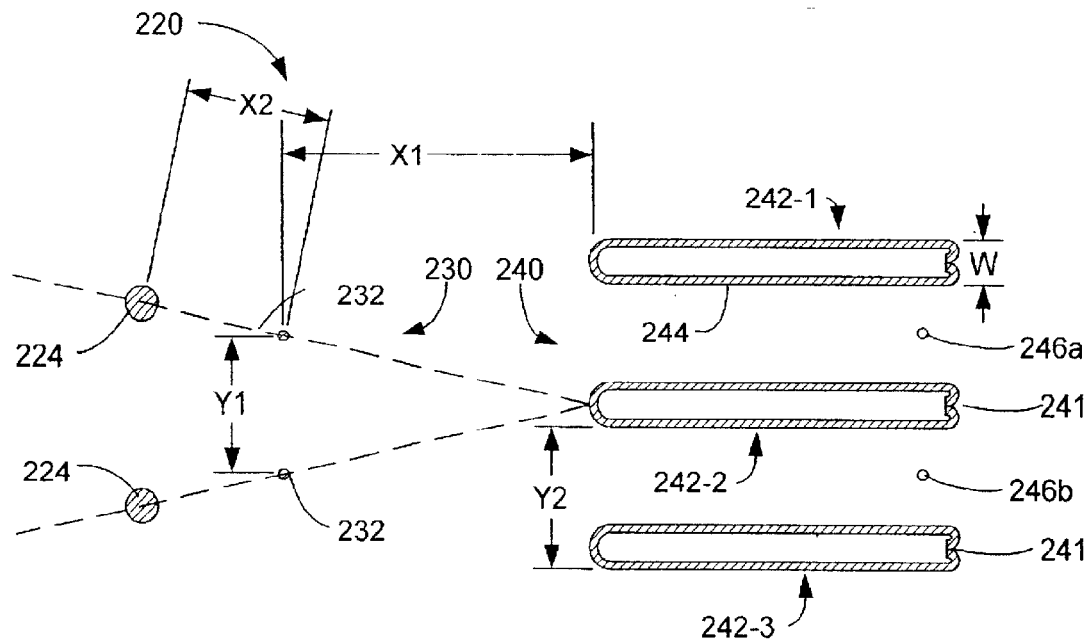
Figure 14F:
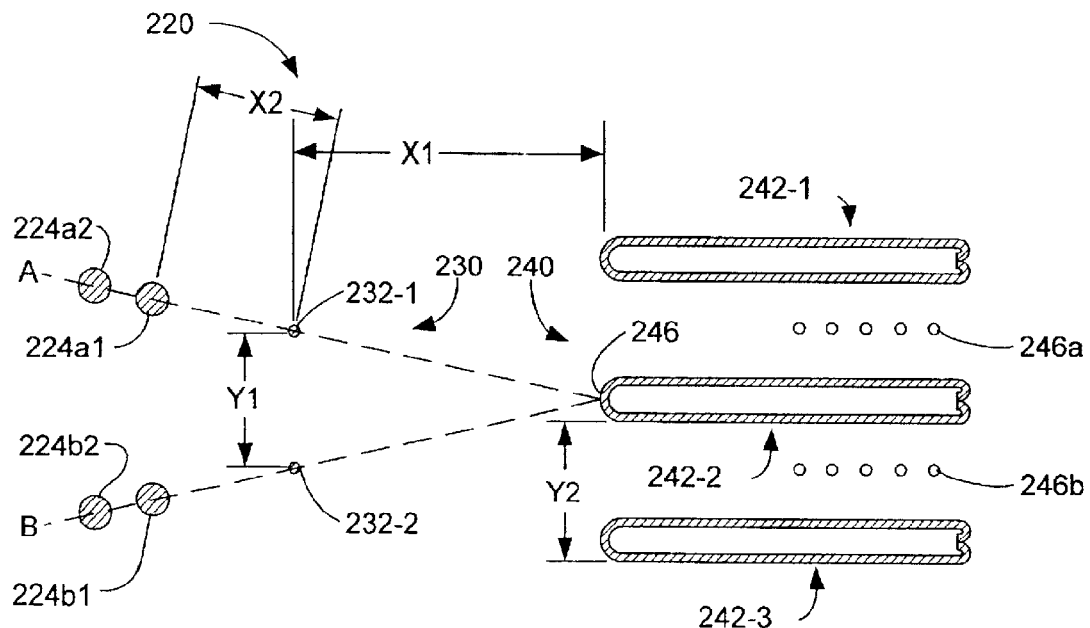

Electrode Assemblies with Second Collector Electrodes Having Interstitial Electrodes:
FIGS. 14E–14F FIG. 14E illustrates another embodiment of the electrode assembly 220 with an interstitial electrode 246. In this embodiment, the interstitial electrode 246 is located midway between the second electrodes 242. For example, the interstitial electrode 246a is located midway between the second electrodes 242-1, 242-2, while the interstitial electrode 246b is located midway between second electrodes 242-2, 242-3. Preferably, the interstitial electrode 246a, 246b are electrically connected to the first electrodes 232, and generate an electrical field with the same positive or negative charge as the first electrodes 232. The interstitial electrode 246 and the first electrode 232 then have the same polarity. Accordingly, particles traveling toward the interstitial electrode 246 will be repelled by the interstitial electrode 246 towards the second electrodes 242. Alternatively, the interstitial electrodes can have a floating potential or be grounded.

It is to be understood that interstitial electrodes 246a, 246b may also be closer to one second collector electrode than to the other. Also, the interstitial electrodes 246a, 246b are preferably located substantially near or at the protective end 241 or ends of the trailing sides 244, as depicted in FIG. 14E. Still further the interstitial electrode can be substantially located along a line between the two trailing portions or ends of the second electrodes. These rear positions are preferred as the interstitial electrodes can cause the positively charged particle to deflect towards the trailing sides 244 along the entire length of the negatively charged second collector electrode 242, in order for the second collector electrode 242 to collect more particles from the airflow.

Still further, the interstitial electrodes 246a, 246b can be located upstream along the trailing side 244 of the second collector electrodes 244. However, the closer the interstitial electrodes 246a, 246b get to the nose 246 of the second electrode 242, generally the less effective interstitial electrodes 246a, 246b are in urging positively charged particles toward the entire length the second electrodes 242. Preferably, the interstitial electrodes 246a, 246b are wire-shaped and smaller or substantially smaller in diameter than the width "W" of the second collector electrodes 242. For example, the interstitial electrodes can have a diameter of, the same as, or on the order of, the diameter of the first electrodes. For example, the interstitial electrodes can have a diameter of one-sixteenth of an inch. Also, the diameter of the interstitial electrodes 246a, 246b is substantially less than the distance between second collector electrodes, as indicated by Y2. Further the interstitial electrode can have a length or diameter in the downstream direction that is substantially less than the length of the second electrode in the downstream direction. The reason for this size of the interstitial electrodes 246a, 246b is so that the interstitial electrodes 246a, 246b have a minimal effect on the airflow rate exiting the device 100 or 200.

FIG. 14F illustrates that the electrode assembly 220 in FIG. 14E can include a pair of third electrodes 224 upstream of each first electrode 232. As previously described, the pair of third electrodes 224 are preferably in-line and symmetrically aligned with each other. For example, the third electrode 224a2 is in-line and symmetrically aligned with the third electrode 224a1 along extension line A. Extension line A preferably extends from the middle of the nose 246 of the second electrode 242-2 through the center of the first electrode 232-1. As previously disclosed, in a preferred embodiment, only the third electrodes 224a1, 224b1 are electrically connected to the high voltage generator 170. In FIG. 14F, a plurality of interstitial electrode 296a and 246b are located between the second electrodes 242. Preferably these interstitial electrodes are in-line and have a potential gradient with an increasing voltage potential on each successive interstitial electrode in the downstream direction in order to urge particles toward the second electrodes. In this situation the voltage on the interstitial electrodes would have the same sign as the voltage on the first electrode 232.

Electrode Assembly with an Enhanced First Emitter Electrode Being Slack:

FIGS. 15A–15C

The previously described embodiments of the electrode assembly 220 include a first array of electrodes 230 having at least one wire or rod shaped electrode 232. It is within the scope of the present invention for the first array of electrodes 230 to contain electrodes consisting of other shapes and configurations.

Figure 15A:
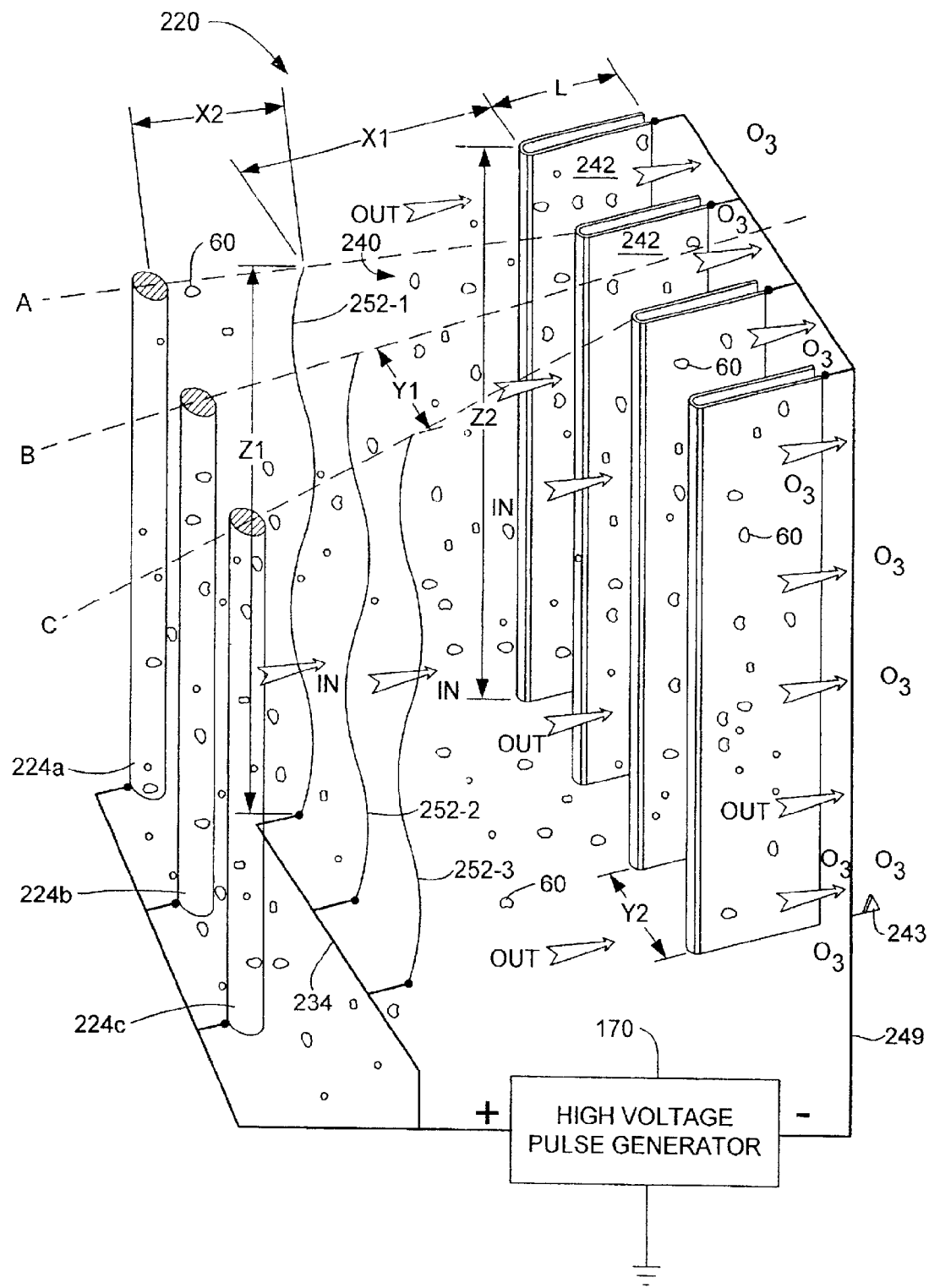
FIGS. 15A–15C.

FIG. 15A illustrates that the first array of electrodes 230 may include curved or slack wire-shaped electrodes 252. The curved wire-shaped electrode 252 is an ion emitting surface and generates an electric field similar to the previously described wire-shaped electrodes 232. In this embodiment, the electrode assembly 220 includes a first array of electrodes 230 having three curved electrodes 252, and a second array of electrodes 240 having four "U"-shaped electrodes 242. Each second electrode 242 is "downstream," and each third focus electrode 224 is "upstream," to the curved wire-shaped electrodes 252 similar to the embodiment shown in FIG. 9A. The electrical properties and characteristics of the second electrodes 242 and third focus electrode 224 are similar to the previously described embodiment shown in FIG. 9A. It is to be understood that an alternative embodiment of FIG. 15A can exclude the focus electrodes and be within the spirit and scope of the invention.

As shown in FIG. 15A, positive ions are generated and emitted by the first electrode 252. In general, the quantity of negative ions generated and emitted by the first electrode is proportional to the surface area of the first electrode. The height Z1 of the first electrode 252 is equal to the height Z1 of the previously disclosed wire-shaped electrode 232. However, the total length of the electrode 252 is greater than the total length of the electrode 232. By way of example only, and in a preferred embodiment, if the electrode 252 was straightened out, the curved or slack wire electrode 252 is 15–30% longer than the rod or wire-shaped electrode 232. The curved electrode 252 is allowed to be slack to achieve the shorter height Z1. When a wire is held slack, the wire may form a curved shape similar to the first electrode 252 shown in FIG. 15A. The greater total length of the curved electrode 252 translates to a larger surface area than the wire-shaped electrode 232. Thus, the electrode 252 will generate and emit more ions than the electrode 232. Ions emitted by the first electrode array attach to the particulate matter within the airflow. The charged particulate matter is attracted to, and collected by, the oppositely charged second collector electrodes 242. Since the electrodes 252 generate and emit more ions than the previously described rod or wire shaped electrodes 232, more particulate matter will be removed from the airflow.

Figure 15B:
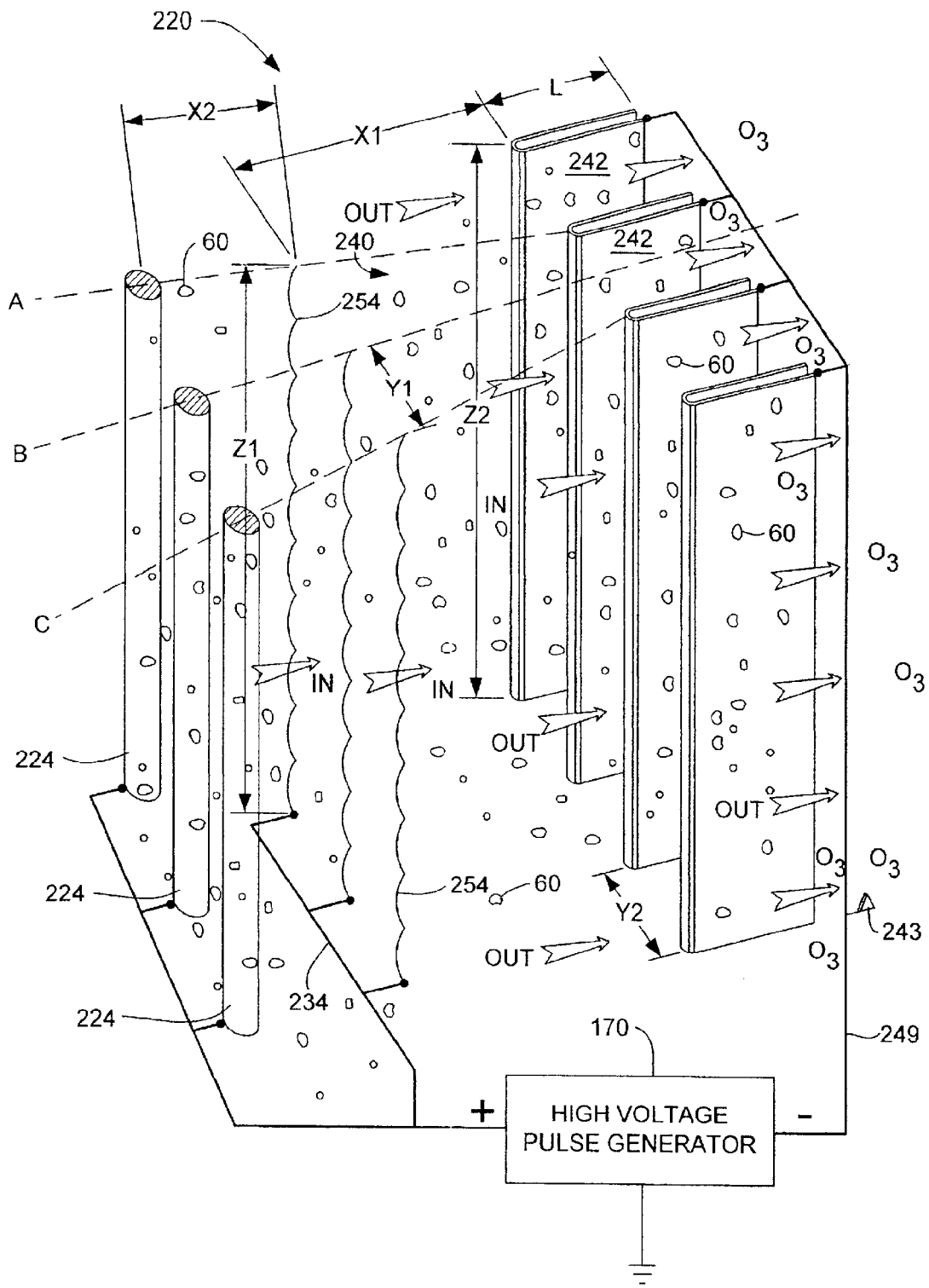

FIG. 15B illustrates that the first array of electrodes 230 may include flat coil wire-shaped electrodes 254. Each flat coil wire-shaped electrode 254 also has a larger surface area than the previously disclosed wire-shaped electrode 232. By way of example only, and in a preferred embodiment, if the electrode 254 was straightened out, the electrode 254 will have a total length that is preferably 10% longer than the rod shaped electrode 232. Since the height of the electrode 254 remains at Z1, the electrode 254 has a "kinked" configuration as shown in FIG. 15B. This greater length translates to a larger surface area of the electrode 254 than the surface area of the electrode 232. Accordingly, the electrode 254 will generate and emit a greater number of ions than electrode 232. It is to be understood that an alternative embodiment of FIG. 15B can exclude the focus electrodes and be within the spirit and scope of the invention.

Figure 15C:
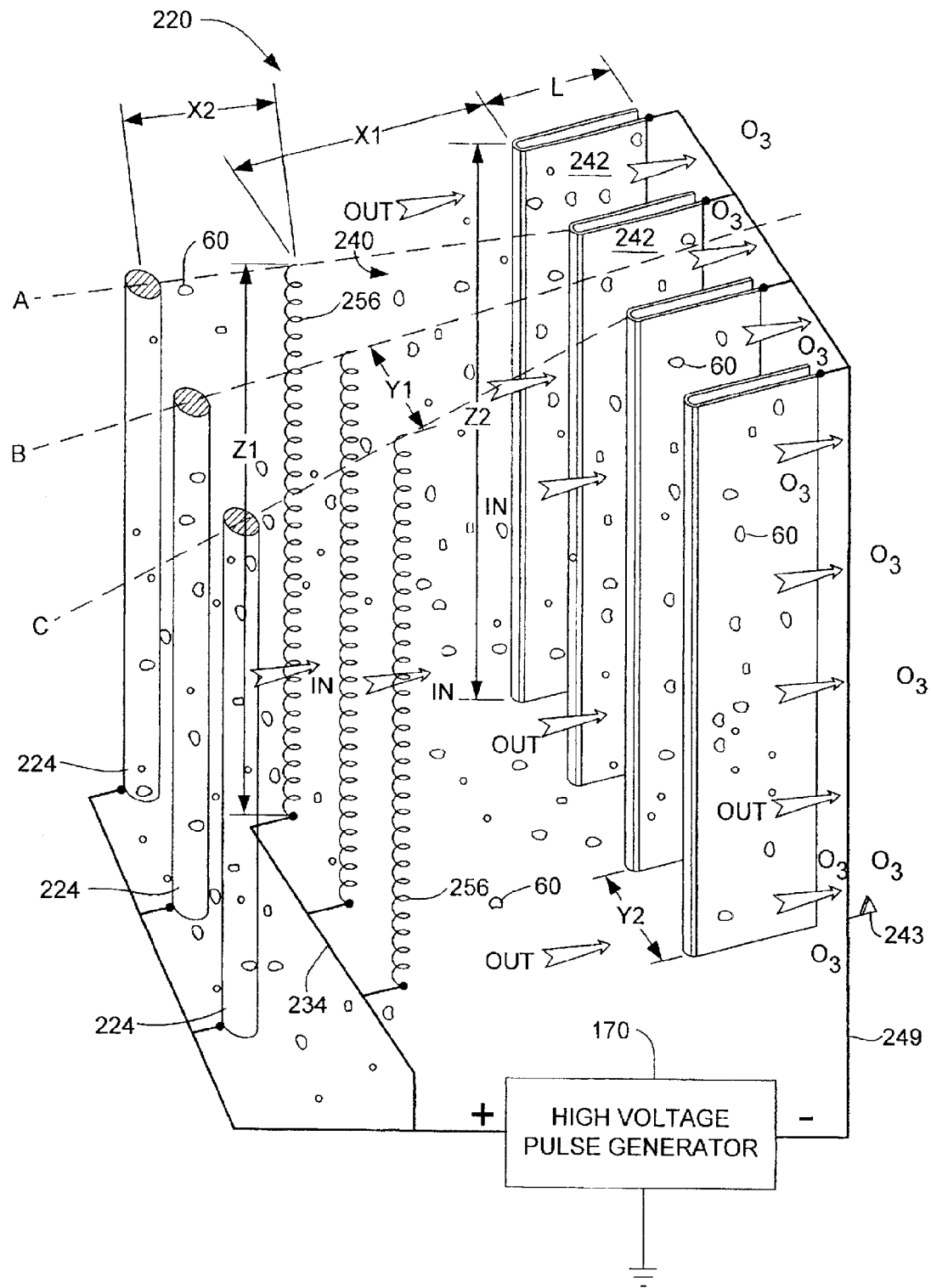

FIG. 15C illustrates that the first array of electrodes 230 may also include coiled wire-shaped electrodes 256. Again, the height Z1 of the electrodes 256 are similar to the height Z1 of the previously described rod shaped electrodes 232. However, the total length of each electrode 256 is greater than the total length of the rod-shaped electrodes 232. By way of example only, and in a preferred embodiment, if the coiled electrode 256 was straightened out, each electrode 256 will have a total length two to three times longer than the wire-shaped electrodes 232. Thus, the electrodes 256 have a larger surface area than the electrodes 232, and generate and emit more ions than the first electrodes 232.The diameter of the wire that is coiled to produce the electrode 256 is similar to the diameter of the electrode 232. The diameter of the electrode 256 itself is preferably 1–3 mm, but can be smaller in accordance with the diameter of first emitter electrode 232. The diameter of the electrode 256 shall remain small enough so that the electrode 256 has a high emissivity and is an ion emitting surface. It is to be understood that an alternative embodiment of FIG. 15C can exclude the focus electrodes and be within the spirit and scope of the invention.

The electrodes 252, 254 and 256 shown in FIGS. 15A–15C maybe incorporated into any of the electrode assembly 220 configurations previously disclosed in this application.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Modifications and variations may be made to the disclosed embodiments without departing from the subject and spirit of the invention as defined by the following claims. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. An air conditioner device, comprising:
   a free-standing vertically elongated housing;
   a first plurality of vertically elongated louvers formed in said housing and defining a first air vent;
   a second plurality of vertically elongated louvers formed in a removable panel and defining a second air vent, said panel adapted to be secured to said housing;

an ion generator positioned in said housing that creates an electro-kinetic airflow between said air vents;

a vertically elongated germicidal lamp positioned in said housing between said air vents; and first and second vertically elongated walls adjacent said germicidal lamp, said first wall located between said first air vent and said lamp to prevent a user from looking through said first air vent and directly viewing UV radiation emitted from said lamp, said second wall located between said second air vent and said lamp to prevent a user from looking through said second air vent and directly viewing UV radiation emitter from said lamp;

wherein said second wall is attached to said removable panel so that access is provided to said germicidal lamp when said panel is removed from said housing; and wherein said louvers defining said first air vent are generally planar and extend in a direction generally parallel to one another, and said louvers defining said second air vent are generally planar and extend in a direction generally parallel to one another, so as to not significantly impede air entering said housing and exiting said housing through said air vents.

2. The device of claim 1, wherein said wall that is attached to said removable panel has a concave surface facing said lamp.

3. The device of claim 2, wherein said wall that is not attached to said removable panel has a convex surface facing said lamp.

4. The device of claim 1, further comprising
a safety mechanism that cuts-off power to at least said lamp when said removable panel is removed from said housing.

5. The device of claim 4, wherein said safety mechanism allows power to be provided to at least said lamp when said removable panel is secured to said housing.

6. The device of claim 4, wherein said safety mechanism includes:

a switch having a first position and a second position; and a tab projecting from said removable panel and adapted to interface with said switch such that said switch is in said first position when said removable panel is secured to said housing, and said switch is in a second position when said removable panel is removed from said housing;

wherein said switch allows power to be provided to at least said lamp when said switch is in said first position; and wherein said switch cuts-off power to at least said lamp when said switch is in said second position.

7. The device of claim 6, further comprising:
a recess within which said switch is positioned;

wherein said tab fits within said recess and engages said switch when said panel is secured to said housing, thereby causing said switch to be in said first position; and wherein said tab disengages from said switch when said panel is removed from said housing, thereby causing said switch to be in said second position.

8. An air conditioner device, comprising:
a free-standing housing defining an interior between an inlet and an outlet;

a removable panel, securable to said housing, and within which is defined said inlet, said panel including a first side that faces said interior of said housing and a second side that faces away from said housing when said panel is secured to said housing;

an ion generator positioned within said interior of said housing;

a germicidal lamp positioned within said interior of said housing; and a wall attached to said first side of said removable panel, said wall arranged to prevent a user from directly looking through said inlet and directly viewing UV radiation emitted from said lamp when said panel is secured to said housing;

wherein said lamp is accessible to a user when said removable panel and said attached wall are removed from said housing;

wherein said inlet is defined by a plurality of louvers that are generally planar and extend in a direction generally parallel to one another so as to not significantly impede air entering said housing through said inlet; and wherein said outlet is defined by a plurality of louvers that are generally planar and extend in a direction generally parallel to one another, so as to not significantly impede air exiting said housing through said outlet.

9. The device of claim 8, wherein said wall that is attached to said removable panel has a concave surface facing said lamp.

10. The device of claim 8, further comprising a second wall positioned within said interior of said housing, said second wall to prevent a user from looking through said outlet and directly viewing UV radiation emitted from said lamp.

11. The device of claim 10, wherein said second wall has a convex surface facing said lamp.

12. The device of claim 8, further comprising:
a safety mechanism that cuts-off power to at least said lamp when said removable panel is removed from said housing.

13. The device of claim 12, wherein said safety mechanism allows power to be provided to at least said lamp when said removable panel is secured to said housing.

14. The device of claim 13, wherein said safety mechanism includes:

a tab extending from a first side of said removable panel;

a recess within which said tab fits when said removable panel is secured to said housing; and a switch, within said recess, said switch depressed by said tab when said removable panel is secured to said housing;

wherein said switch cuts-off power to at least said lamp when said tab does not depress said switch; and wherein said switch allows power to be provided to at least said lamp when said tab depresses said switch.

15. The device of claim 8, wherein said ion generator produces an airflow from said inlet to said outlet when powered.

16. The device of claim 8, further comprising:
a safety mechanism that cuts-off power to said lamp and said ion generator when said removable panel is removed from said housing.

17. The device of claim 16, wherein said safety mechanism allows power to be provided to said lamp and said ion generator when said removable panel is secured to said housing.

18. The device of claim 17, wherein said safety mechanism includes:
   a tab extending from a first side of said removable panel;
   a recess within which said tab fits when said removable panel is secured to said housing; and
   a switch, within said recess, said switch depressed by said tab when said removable panel is secured to said housing;
   wherein said switch cuts-off power to said lamp and said ion generator when said tab does not depress said switch; and
   wherein said switch allows power to be provided to said lamp and said ion generator when said tab depresses said switch.

19. The device of claim 17, wherein said safety mechanism includes a switch that cuts-off power to said lamp and said ion generator when said removable panel is removed from said housing.

20. An air conditioner device, comprising:
   a free-standing housing defining an interior between an inlet and an outlet;
   a removable panel, adapted to be secured to said housing, and within which is defined said inlet, said panel including a first side that faces said interior of said housing and a second side that faces away from said housing when said panel is secured to said housing;
   an ion generator positioned within said interior of said housing;
   a germicidal lamp positioned within said interior of said housing such that a user looking through said inlet or said outlet cannot directly view UV radiation emitted from said lamp; and
   a safety mechanism that cuts-off power to at least said lamp when said removable panel is removed from said housing;
   wherein said lamp is accessible to a user when said removable panel is removed from said housing;
   wherein said inlet is defined by a plurality of louvers that are generally planar and extend in a direction generally parallel to one another so as to not significantly impede air entering said housing through said inlet; and
   wherein said outlet is defined by a plurality of louvers that are generally planar and extend in a direction generally parallel to one another, so as to not significantly impede air exiting said housing through said outlet.

21. The device of claim 20, wherein said safety mechanism allows power to be provided to at least said lamp when said removable panel is secured to said housing.

22. The device of claim 21, wherein said safety mechanism includes a switch that cuts-off power to at least said lamp when said removable panel is removed from said housing.

23. The device of claim 20, wherein said safety mechanism comprises:
   a tab extending from a first side of said removable panel;
   a recess within which said tab fits when said removable panel is secured to said housing; and
   a switch, within said recess, said switch depressed by said tab when said removable panel is secured to said housing;
   wherein said switch cuts-off power to at least said lamp when said tab does not depress said switch; and
   wherein said switch allows power to be provided to at least said lamp when said tab depresses said switch.

24. The device of claim 20, wherein said ion generator produces an airflow from said inlet to said outlet when powered.

25. The device of claim 20, further comprising:
   a safety mechanism that cuts-off power to said lamp and said ion generator when said removable panel is removed from said housing.

26. The device of claim 25, wherein said safety mechanism allows power to be provided to said lamp and said ion generator when said removable panel is secured to said housing.

27. The device of claim 26, wherein said safety mechanism comprises:
   a tab extending from a first side of said removable panel;
   a recess within which said tab fits when said removable panel is secured to said housing; and
   a switch, within said recess, said switch depressed by said tab when said removable panel is secured to said housing;
   wherein said switch cuts-off power to said lamp and said ion generator when said tab does not depress said switch; and
   wherein said switch allows power to be provided to said lamp and said ion generator when said tab depresses said switch.

28. An air conditioner device, comprising:
   a free-standing housing defining an interior between a first air vent and a second air vent;
   a removable panel, securable to said housing, and within which is defined said second air vent, said panel including a first side that faces said interior of said housing and a second side that faces away from said housing when said panel is secured to said housing;
   an ion generator positioned within said interior of said housing;
   a germicidal lamp positioned in said housing between said first and second air vents; and
   a vertically elongated wall adjacent said germicidal lamp, said wall arranged to prevent a user from looking through said second air vent and directly viewing UV radiation emitted from said lamp;
   wherein access is provided to said germicidal lamp when said panel and said wall are removed from said housing; and
   wherein said first air vent is defined by a plurality of louvers that are generally planar and extend in a direction generally parallel to one another, and said second air vent is defined by a plurality of louvers that are generally planar and extend in a direction generally parallel to one another, so as to not significantly impede air entering and exiting said housing through said first air vent and said second air vent.

29. The device of claim 28, wherein said wall is attached to said removable panel, and thereby removed from said housing when said panel is removed from said housing.

30. The device of claim 29, wherein said wall is integrally formed with said removable panel.

31. The device of claim 28, further comprising a second wall positioned within said interior of said housing, said second wall to prevent a user from looking through said first air vent and directly viewing UV radiation emitted from said lamp.

32. An air conditioner device, comprising:
   a free-standing housing defining an interior between a pair of air vents;

a removable panel securable to said housing, and within which is defined one of said air vents, said panel including a first side that faces said interior of said housing and a second side that faces away from said housing when said panel is secured to said housing;

an ion generator positioned within said interior of said housing;

a germicidal lamp positioned within said interior of said housing such that a user looking through said air vents cannot directly view UV radiation emitted from said lamp; and a safety mechanism that cuts-off power to at least said lamp when said removable panel is removed from said housing;

wherein said lamp is accessible to a user when said removable panel is removed from said housing; and wherein said pair of air vents are each defined by a respective plurality of louvers that they are generally planar and extend in a direction generally parallel to one another so as to not significantly impede air entering and exiting said housing through said air vents.

33. An air conditioner device, comprising:

a free-standing housing defining an interior between a first air vent and second air vent;

a removable panel, securable to said housing, and within which is defined one of said air vents, said panel including a first side that faces said interior of said housing and a second side that faces away from said housing when said panel is secured to said housing;

an ion generator positioned within said interior of said housing;

a germicidal lamp positioned within said interior of said housing; and a wall attached to said first side of said removable panel, said wall arranged to prevent a user from directly looking through said one of said air vents defined in said removable panel and directly viewing UV radiation emitted from said lamp when said panel is secured to said housing;

wherein said lamp is accessible to a user when said removable panel and said attached wall are removed from said housing.

34. The device of claim 33, wherein:

said first air vent includes a plurality of louvers that are generally planar and extend in a direction generally parallel to one another so as to not significantly impede air flowing through said first air vent; and said second air vent includes a plurality of louvers that are generally planar and extend in a direction generally parallel to one another, so as to not significantly impede air flowing through said second air vent.

35. The device of claim 33, wherein said wall has a concave surface facing said lamp and a convex surface facing said air vent.

36. The device of claim 33, further comprising:

a safety mechanism that cuts-off power to at least said lamp when said removable panel is removed from said housing.

37. The device of claim 33, wherein said wall is integrally formed with said removable panel.

38. An air conditioner device, comprising:

a free-standing housing defining an interior and an air vent that allows air to enter said interior of said housing;

a removable panel securable to said housing, and within which is defined said air vent, said panel including a first side that faces said interior of said housing and a second side that faces away from said housing when said panel is secured to said housing;

an ion generator positioned within said interior of said housing;

a germicidal lamp positioned within said interior of said housing; and a wall attached to said first side of said removable panel and arranged to prevent a user from looking through said air vent and directly viewing UV radiation emitted from said lamp;

wherein said lamp is accessible to a user when said removable panel and said wall attached thereto are removed from said housing.

39. The device of claim 38, wherein said air vent includes a plurality of louvers that are generally planar and extend in a direction generally parallel to one another so as to not significantly impede air flowing through said air vent.

40. The device of claim 38, wherein said wall has a concave surface facing said lamp and a convex surface facing said air vent.

41. The device of claim 38, further comprising;

a safety mechanism that cuts-off power to at least said lamp when said removable panel is removed from said housing.

42. The device of claim 38, wherein said wall is integrally formed with said removable panel.

* * * * *